United States Patent
Matsumoto et al.

(10) Patent No.: US 9,459,221 B2
(45) Date of Patent: Oct. 4, 2016

(54) ELECTRONIC DEVICE, INFORMATION PROCESSING APPARATUS, INFORMATION PROCESSING METHOD, AND PROGRAM

(71) Applicant: Panasonic Corporation, Osaka (JP)

(72) Inventors: Akinori Matsumoto, Osaka (JP); Koji Morikawa, Kyoto (JP); Jeffry Bonar Fernando, Osaka (JP); Katsuyoshi Yamagami, Osaka (JP); Jun Ozawa, Nara (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 257 days.

(21) Appl. No.: 14/338,535

(22) Filed: Jul. 23, 2014

(65) Prior Publication Data

US 2014/0333332 A1    Nov. 13, 2014

Related U.S. Application Data

(63) Continuation of application No. PCT/JP2013/005346, filed on Sep. 10, 2013.

(30) Foreign Application Priority Data

Sep. 10, 2012   (JP) ................................ 2012-198233

(51) Int. Cl.
*G01N 27/04* (2006.01)
*A61B 5/00* (2006.01)
(Continued)

(52) U.S. Cl.
CPC ............ *G01N 27/04* (2013.01); *A61B 5/0402* (2013.01); *A61B 5/0404* (2013.01); *A61B 5/05* (2013.01); *A61B 5/053* (2013.01); *A61B 5/6898* (2013.01); *G06F 3/01* (2013.01)

(58) Field of Classification Search
CPC ................................ G01N 27/04; G06F 3/01
See application file for complete search history.

(56) References Cited

U.S. PATENT DOCUMENTS

| 6,188,925 B1 | 2/2001 | Kawanishi et al. |
| 2007/0018809 A1 | 1/2007 | Reiter et al. |

(Continued)

FOREIGN PATENT DOCUMENTS

| JP | 2002-056382 A | 2/2002 |
| JP | 2004-078634 A | 3/2004 |

(Continued)

OTHER PUBLICATIONS

International Search Report for corresponding International Application No. PCT/JP2013/005346 mailed Dec. 17, 2013.

*Primary Examiner* — Christ Mahoney
(74) *Attorney, Agent, or Firm* — Renner, Otto, Boisselle & Sklar, LLP

(57) ABSTRACT

An exemplary electronic device is in a housing to be gripped by both hands, and measures the potentials of first and second fingers of respectively different hands. The device includes: a first electrode group provided in a position to come in contact with the first finger, including a first main electrode and at least one first auxiliary electrode provided in a position away from the first main electrode; a second electrode group provided in a position to come in contact with the second finger, including a second main electrode and at least one second auxiliary electrode provided in a position away from the second main electrode; a biological signal processor for, from potential values measured at the first and second electrode groups, determining respective contact states concerning the first and second fingers; and a transmission circuit for presenting information concerning a finger contact state based on a result of determination.

16 Claims, 52 Drawing Sheets

| | PRESENCE/ABSENCE OF OUTPUT SIGNAL | | | | | DIRECTION OF FINGER MISPLACEMENT |
|---|---|---|---|---|---|---|
| | LEFT HAND | | | RIGHT HAND | | |
| | Ch1 | Ch2 | Ch3 | Ch4 | Ch5 | |
| FIRST STATE | NO | NO | NO | NO | NO | — |
| SECOND STATE | NO | NO | YES | YES | YES | RIGHT (+P) |
| THIRD STATE | YES | NO | YES | YES | YES | RIGHT (+P) |
| FOURTH STATE | YES | YES | YES | YES | YES | NO MISPLACEMENT |

(51) Int. Cl.
*A61B 5/0402* (2006.01)
*A61B 5/0404* (2006.01)
*A61B 5/05* (2006.01)
*G06F 3/01* (2006.01)
*A61B 5/053* (2006.01)

(56) References Cited

U.S. PATENT DOCUMENTS

| | | | |
|---|---|---|---|
| 2007/0149886 A1 | 6/2007 | Kohls | |
| 2007/0149888 A1 | 6/2007 | Kohls et al. | |
| 2008/0306363 A1* | 12/2008 | Chaiken | A61B 5/0059 600/310 |
| 2012/0071734 A1 | 3/2012 | Shimuta et al. | |
| 2012/0253206 A1 | 10/2012 | Fukuda et al. | |
| 2014/0316227 A1* | 10/2014 | Rake | B62D 1/046 600/323 |
| 2015/0066238 A1* | 3/2015 | Todd | B60K 28/063 701/1 |
| 2015/0228176 A1* | 8/2015 | Sholder | G08B 21/02 340/539.12 |

FOREIGN PATENT DOCUMENTS

| | | |
|---|---|---|
| JP | 2005-096519 A | 4/2005 |
| JP | 2006-212348 A | 8/2006 |
| JP | 2007-508095 T | 4/2007 |
| JP | 2008-149127 A | 7/2008 |
| JP | 2012-029845 A | 2/2012 |
| JP | 2012-210236 A | 11/2012 |
| WO | WO 2010/125705 A1 | 11/2010 |

\* cited by examiner

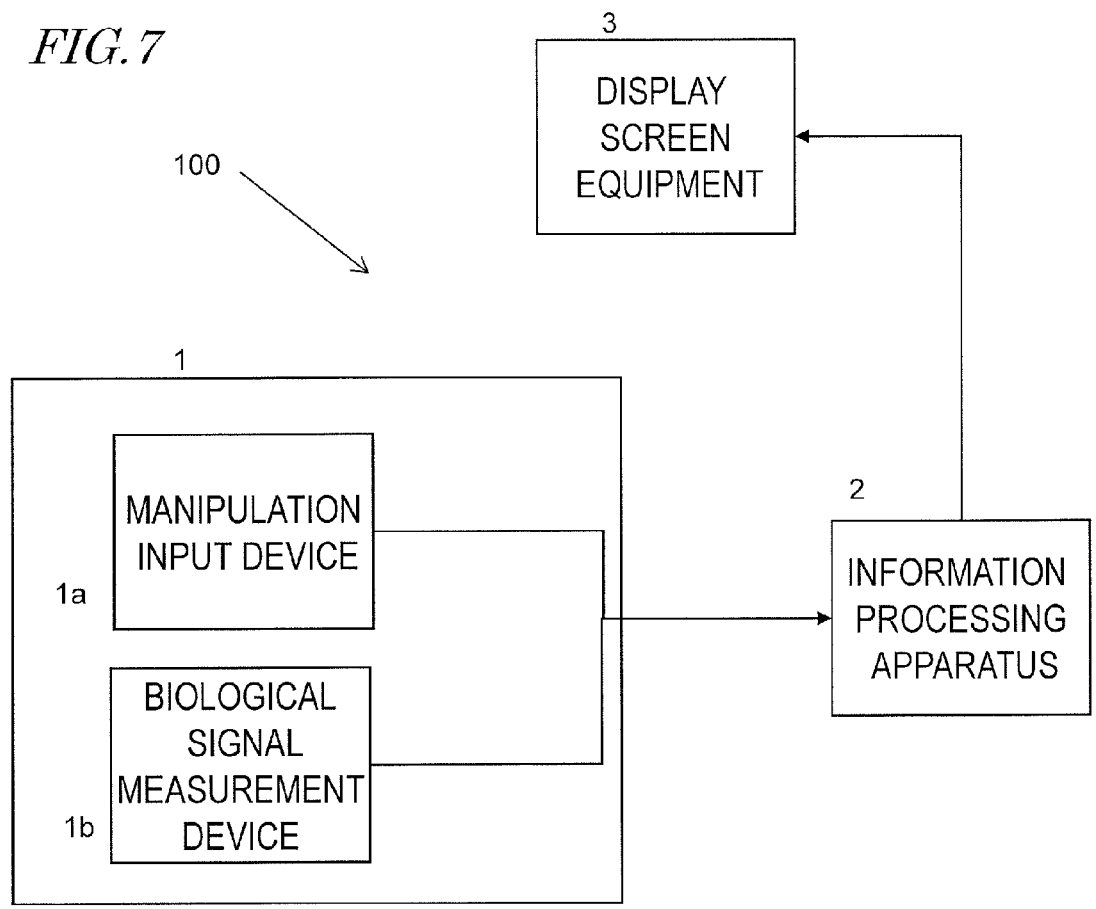

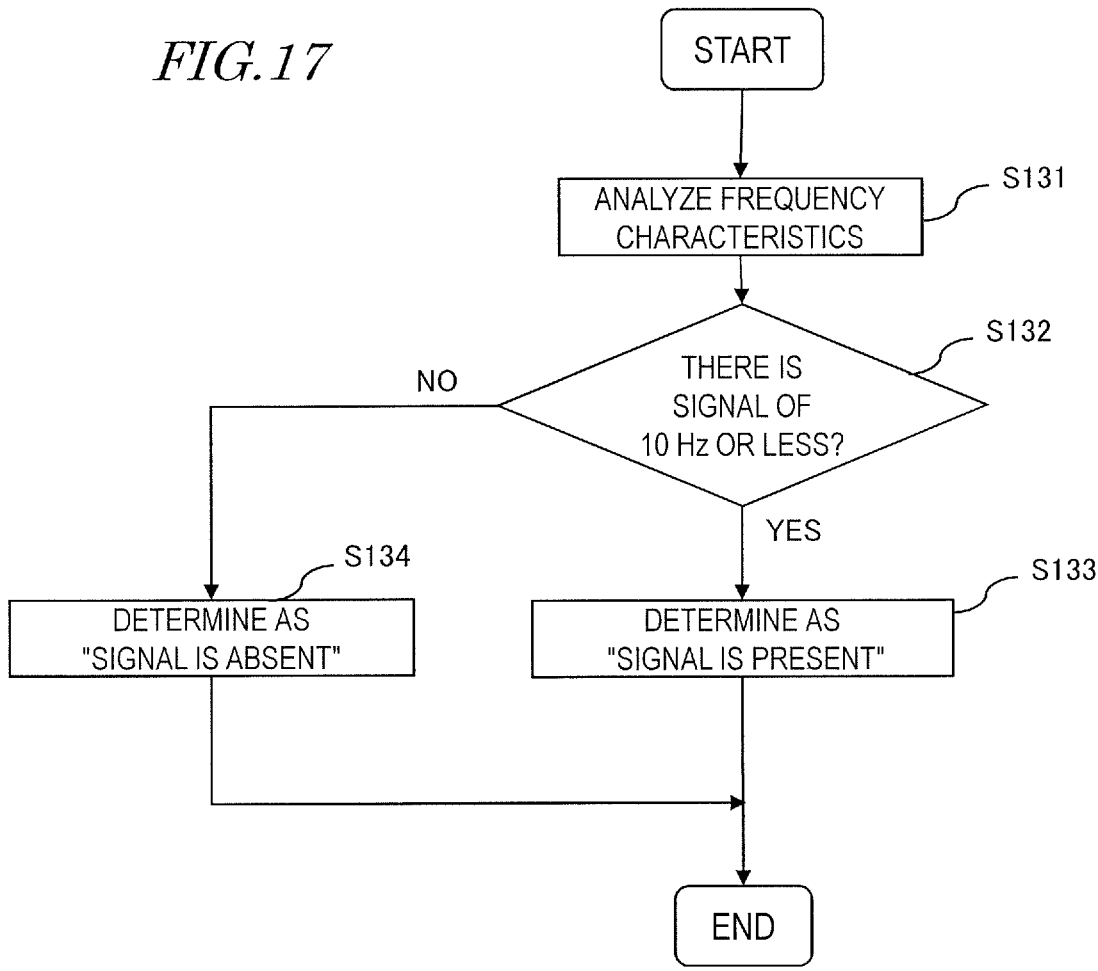

FIG.18

| | PRESENCE/ABSENCE OF OUTPUT SIGNAL | | | | | DIRECTION OF FINGER MISPLACEMENT |
|---|---|---|---|---|---|---|
| | LEFT HAND | | | RIGHT HAND | | |
| | Ch1 | Ch2 | Ch3 | Ch4 | Ch5 | |
| FIRST STATE | NO | NO | NO | NO | NO | — |
| SECOND STATE | NO | NO | YES | YES | YES | RIGHT (+P) |
| THIRD STATE | YES | NO | YES | YES | YES | RIGHT (+P) |
| FOURTH STATE | YES | YES | YES | YES | YES | NO MISPLACEMENT |

Ch1(MAIN ELECTRODE 48a)

Ch2(AUXILIARY ELECTRODE 48b)

Ch3(AUXILIARY ELECTRODE 48c)

Ch4(AUXILIARY ELECTRODE 49b)

Ch5(AUXILIARY ELECTRODE 49c)

Ch1(MAIN ELECTRODE 48a)

Ch2(AUXILIARY ELECTRODE 48b)

Ch3(AUXILIARY ELECTRODE 48c)

Ch4(AUXILIARY ELECTRODE 49b)

Ch5(AUXILIARY ELECTRODE 49c)

FIG.20C
Ch1(MAIN ELECTRODE 48a) 
Ch2(AUXILIARY ELECTRODE 48b) 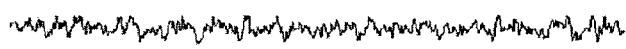
Ch3(AUXILIARY ELECTRODE 48c) 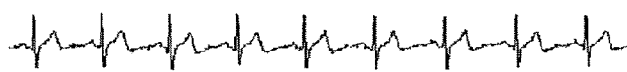
Ch4(AUXILIARY ELECTRODE 49b) 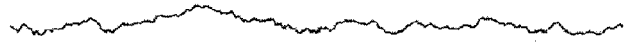
Ch5(AUXILIARY ELECTRODE 49c) 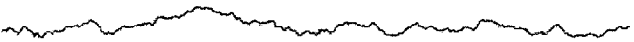
FIG.20D
Ch1(MAIN ELECTRODE 48a) 
Ch2(AUXILIARY ELECTRODE 48b) 
Ch3(AUXILIARY ELECTRODE 48c) 
Ch4(AUXILIARY ELECTRODE 49b) 
Ch5(AUXILIARY ELECTRODE 49c) 

FIG.32

|  | CONTACT IMPEDANCE | | | | | DIRECTION OF FINGER MISPLACEMENT |
|---|---|---|---|---|---|---|
|  | LEFT HAND | | | RIGHT HAND | | |
|  | Ch1 | Ch2 | Ch3 | Ch4 | Ch5 | |
| FIRST STATE | HIGH | HIGH | HIGH | HIGH | HIGH | — |
| SECOND STATE | HIGH | HIGH | LOW | LOW | LOW | RIGHT (+P) |
| THIRD STATE | LOW | HIGH | LOW | LOW | LOW | RIGHT (+P) |
| FOURTH STATE | LOW | LOW | LOW | LOW | LOW | NO MISPLACEMENT |

FIG. 36

| | PRESENCE/ABSENCE OF OUTPUT SIGNAL | | | | | DIRECTION OF FINGER MISPLACEMENT | DEGREE OF FINGER MISPLACEMENT |
|---|---|---|---|---|---|---|---|
| | LEFT HAND | | | RIGHT HAND | | | |
| | Ch1 | Ch2 | Ch3 | Ch4 | Ch5 | | |
| FIRST STATE | YES | NO | NO | NO | NO | NO MISPLACEMENT | NO MISPLACEMENT |
| SECOND STATE | NO | YES | YES | NO | NO | LOWER RIGHT DIRECTION (+Q) | ONE ELECTRODE |
| THIRD STATE | NO | NO | YES | NO | NO | LOWER RIGHT DIRECTION (+Q) | TWO ELECTRODES |

Ch1(MAIN ELECTRODE 48a)

Ch2(AUXILIARY
ELECTRODE 48b)

Ch3(AUXILIARY
ELECTRODE 48c)

Ch4(AUXILIARY
ELECTRODE 49b)

Ch5(AUXILIARY
ELECTRODE 49c)

FIG.43A

|  | Ch1 | Ch2 | Ch3 | Ch4 | Ch5 |
|---|---|---|---|---|---|
| S1 | YES | × | × | × | × |
| S1 | YES | YES | × | × | × |
| S1 | YES | YES | YES | × | × |
| S2 | × | YES | YES | × | × |
| S2 | × | YES | YES | YES | × |
| S3 | × | × | YES | YES | × |
| S3 | × | × | YES | YES | YES |
| S4 | × | × | × | YES | YES |
| S5 | × | × | × | × | YES |

FIG.43B

|  | CHRONOLOGICAL CHANGE IN STATE OF FINGER MISPLACEMENT |
|---|---|
| MOVING IN DIRECTION OF FINGER MISPLACEMENT | S1→S2→S3→S4 |
|  | S1→S2→S3 |
| OSCILLATING FINGER MISPLACEMENT | S1→S2→S1 |
|  | S2→S1→S2→S1 |
| FINGER MISPLACEMENT RESTORED | S4→S3 |
|  | S3→S2 |
| ... | ... |

FIG.46
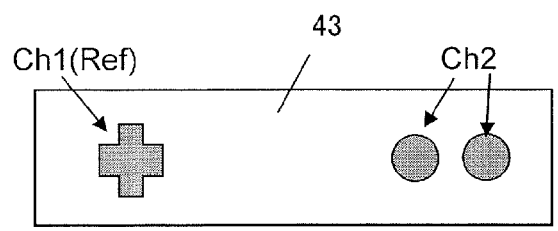
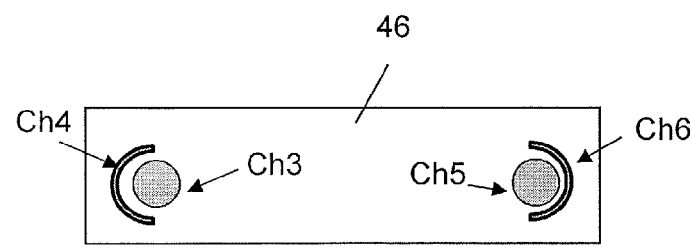
FIG.47
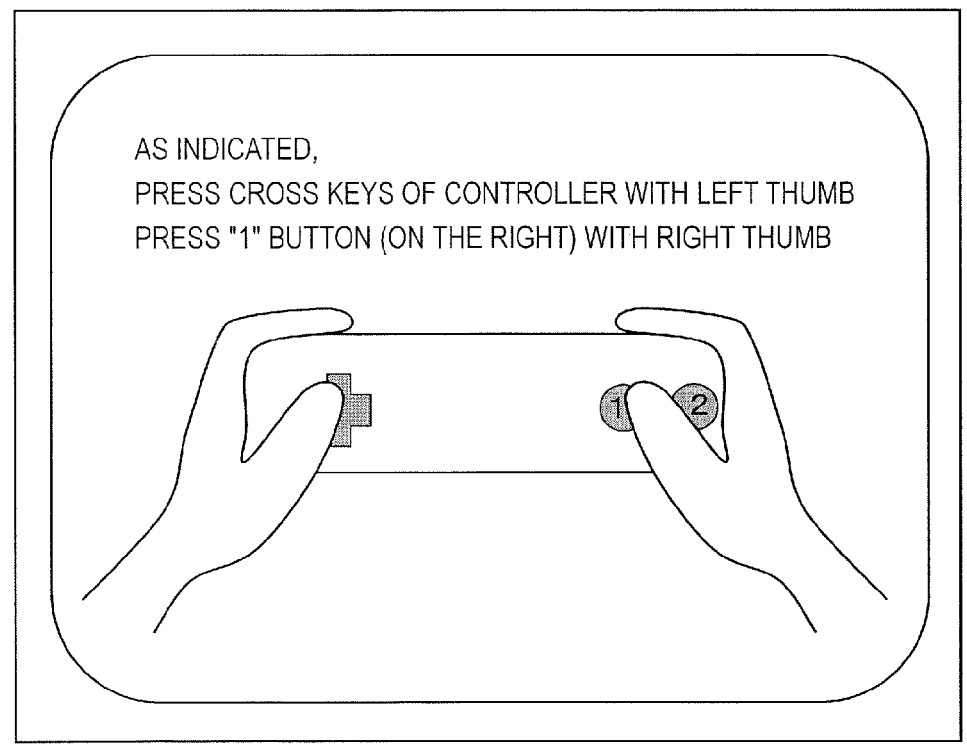

Ch2

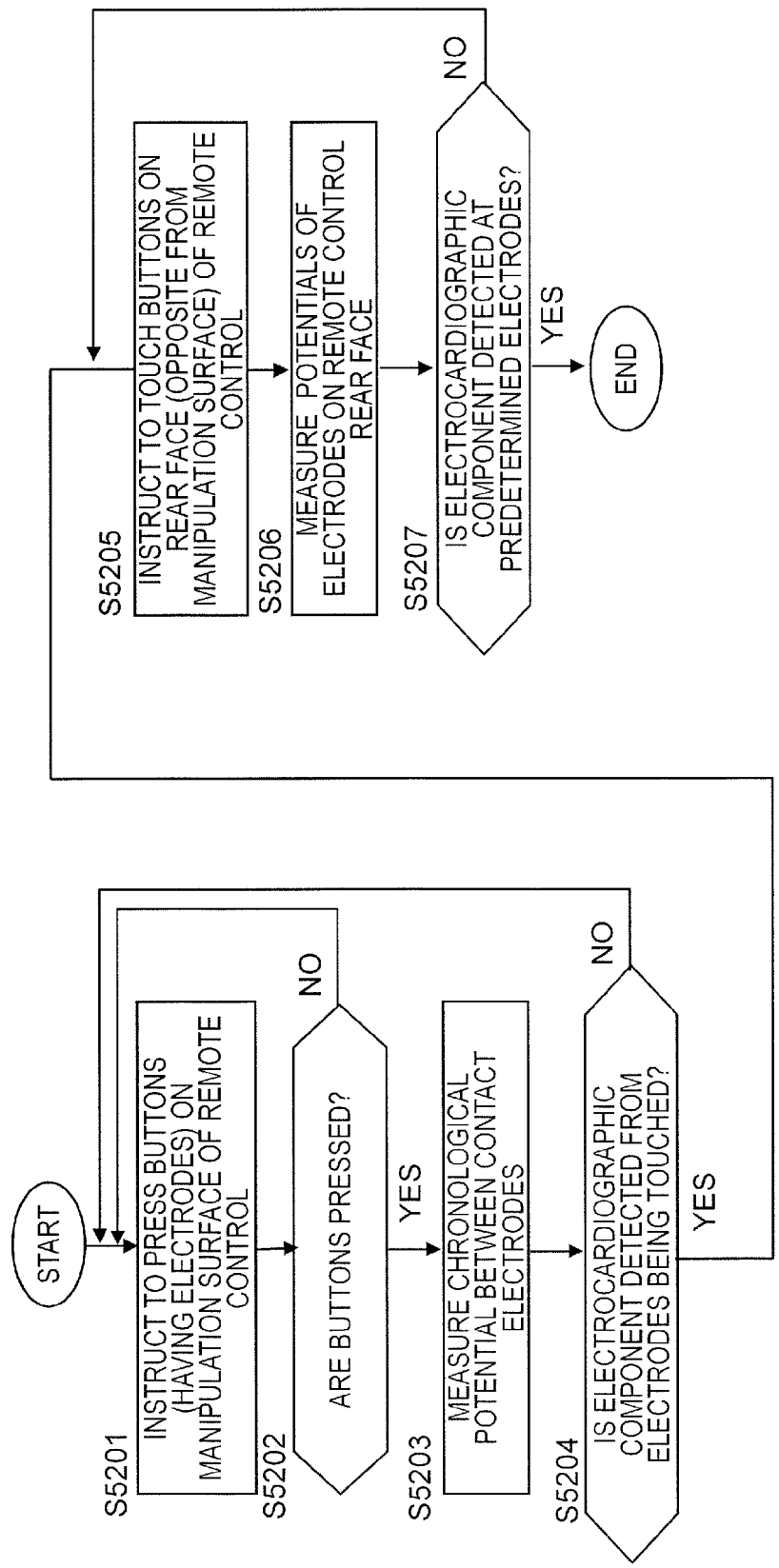

ELECTRONIC DEVICE, INFORMATION PROCESSING APPARATUS, INFORMATION PROCESSING METHOD, AND PROGRAM

This is a continuation of International Application No. PCT/JP2013/005346, with an international filing date of Sep. 10, 2013, which claims priority of Japanese Patent Application No. 2012-198233, filed on Sep. 10, 2013, the contents of which are hereby incorporated by reference.

BACKGROUND

1. Technical Field

The present disclosure relates to an electronic device and an information processing system. More specifically, the present disclosure relates to an information processing system in which a user performs manipulations by using an electronic device as a manipulation input device, e.g., a controller.

2. Description of the Related Art

A user manipulating a game machine may play a game while holding a controller in both hands and manipulating the operation buttons with both hands. In recent years, it is being thought that such a game machine may be provided with a function of measuring a bioelectric potential of a user where, by measuring an electrocardiogram or the like, the health state of the user may be monitored, the psychological state of the user during a game may be estimated, and so on. It is not only game machines that a function of measuring a bioelectric potential is to be provided, but such a function may also be extended to various other devices. Any independent device or group of complex devices including such a device will be referred to as an information processing system in the following.

Conventionally, an information processing system which measures a bioelectric potential of a user via electrodes attached on fingers of one's hands is known (see, for example, Japanese Laid-Open Patent Publication No. 2008-149127).

SUMMARY

In the aforementioned information processing system, a sure contact state is guaranteed because of there being a means of fixing fingers to the electrodes. However, an information processing system lacking such a means of fixture has a problem in that the fingers are not restricted, and that, if the fingers are touching the electrodes at positions which cannot be directly viewed by the user, the fingers may be misplaced from the electrodes so that stable measurement is not possible. This is because fingers that are not restricted may not always rest just right on the electrodes.

One non-limiting, and exemplary embodiment provides a technique to enable more stable bioelectric potential measurements.

In one general aspect, an electronic device according to the present disclosure is an electronic device in a housing to be gripped by a right hand and a left hand of a user for measuring a potential of a first finger and a potential of a second finger of the user, wherein the first finger is a finger of one of the left or right hand, and the second finger is a finger of the other of the left or right hand, the electronic device including: a first electrode group provided in a position to come in contact with the first finger, the first electrode group including a first main electrode and at least one first auxiliary electrode provided at a position away from the first main electrode; a second electrode group provided in a position to come in contact with the second finger, the second electrode group including a second main electrode and at least one second auxiliary electrode provided at a position away from the second main electrode; a biological signal processor for, from a potential value measured at the first electrode group and a potential value measured at the second electrode group, determining respective contact states of the first finger and the second finger; and a transmission circuit for presenting information concerning a finger contact state to the user, based on a result of determination by the biological signal processor.

In accordance with an electronic device as one implementation of the present invention, a direction of misplacement of a finger to rest on an electrode is notified to a user, whereby more stable bioelectric potential measurements are enabled.

These general and specific aspects may be implemented using a system, a method, and a computer program, and any combination of systems, methods, and computer programs.

Additional benefits and advantages of the disclosed embodiments will be apparent from the specification and Figures. The benefits and/or advantages may be individually provided by the various embodiments and features of the specification and drawings disclosure, and need not all be provided in order to obtain one or more of the same.

Figure 5:
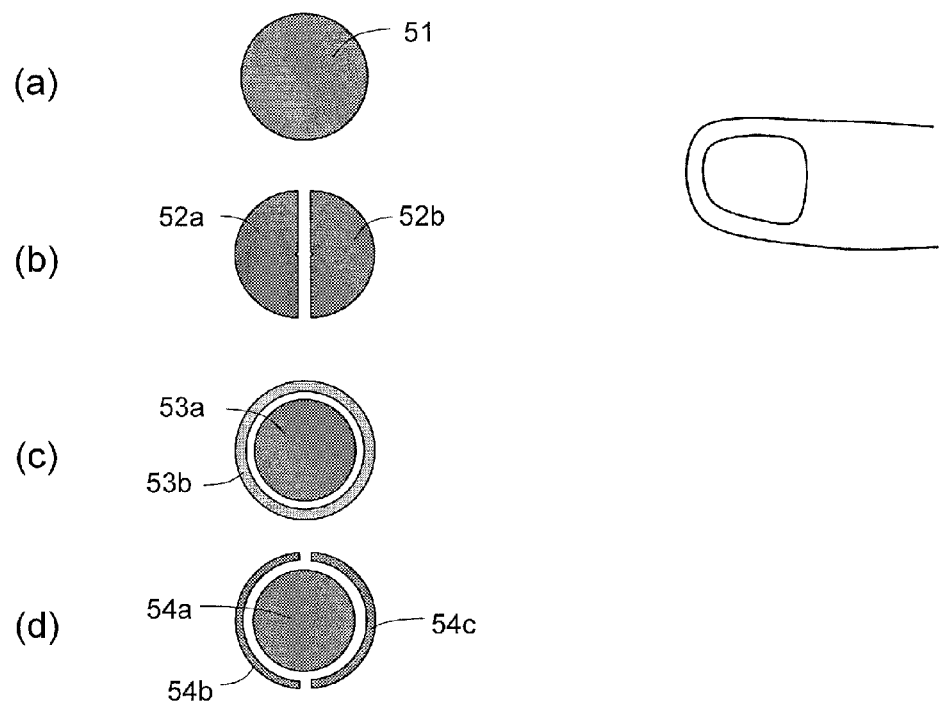

Portions (a) to (d) of FIG. 5 are diagrams showing examples of electrode shapes and numbers of electrodes.

Figure 6A:
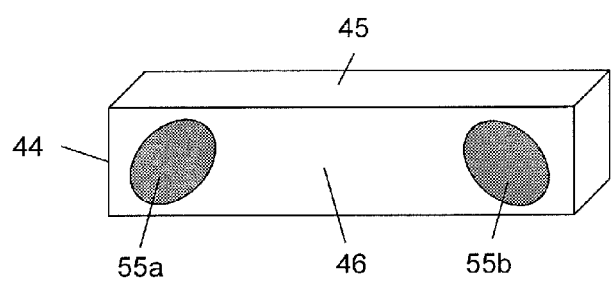
Figure 6B:
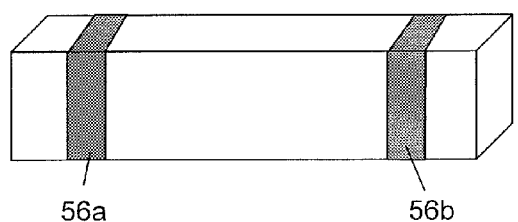
Figure 6C:
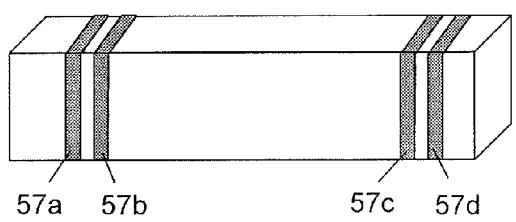

FIGS. 6A to 6C are diagrams showing other examples of electrode shapes.

FIG. 7 is a diagram showing a system construction for the information processing system.

Figure 8:
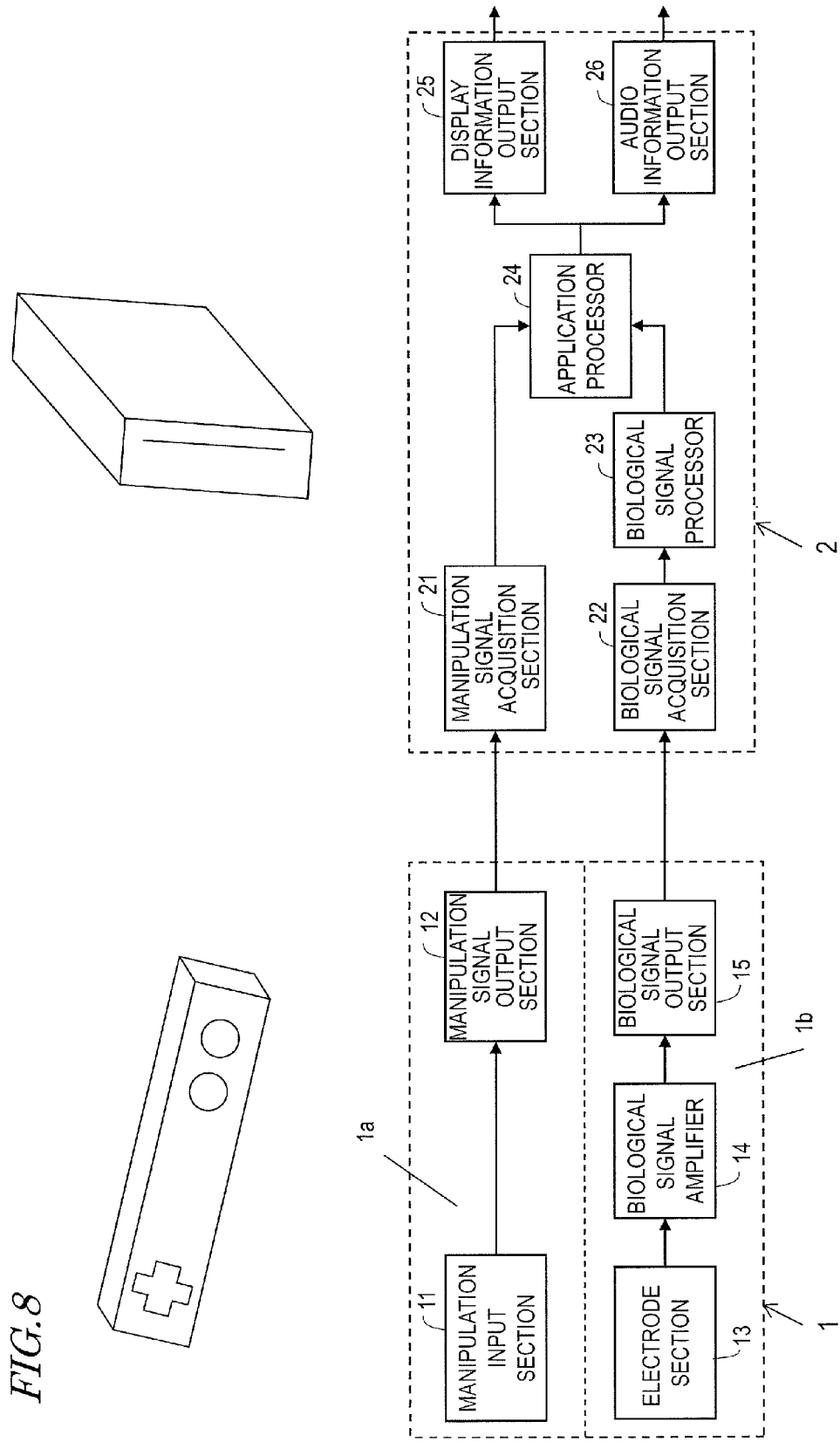

FIG. 8 is a diagram showing the construction of a controller and an information processing apparatus of the information processing system 100.

Figure 9:
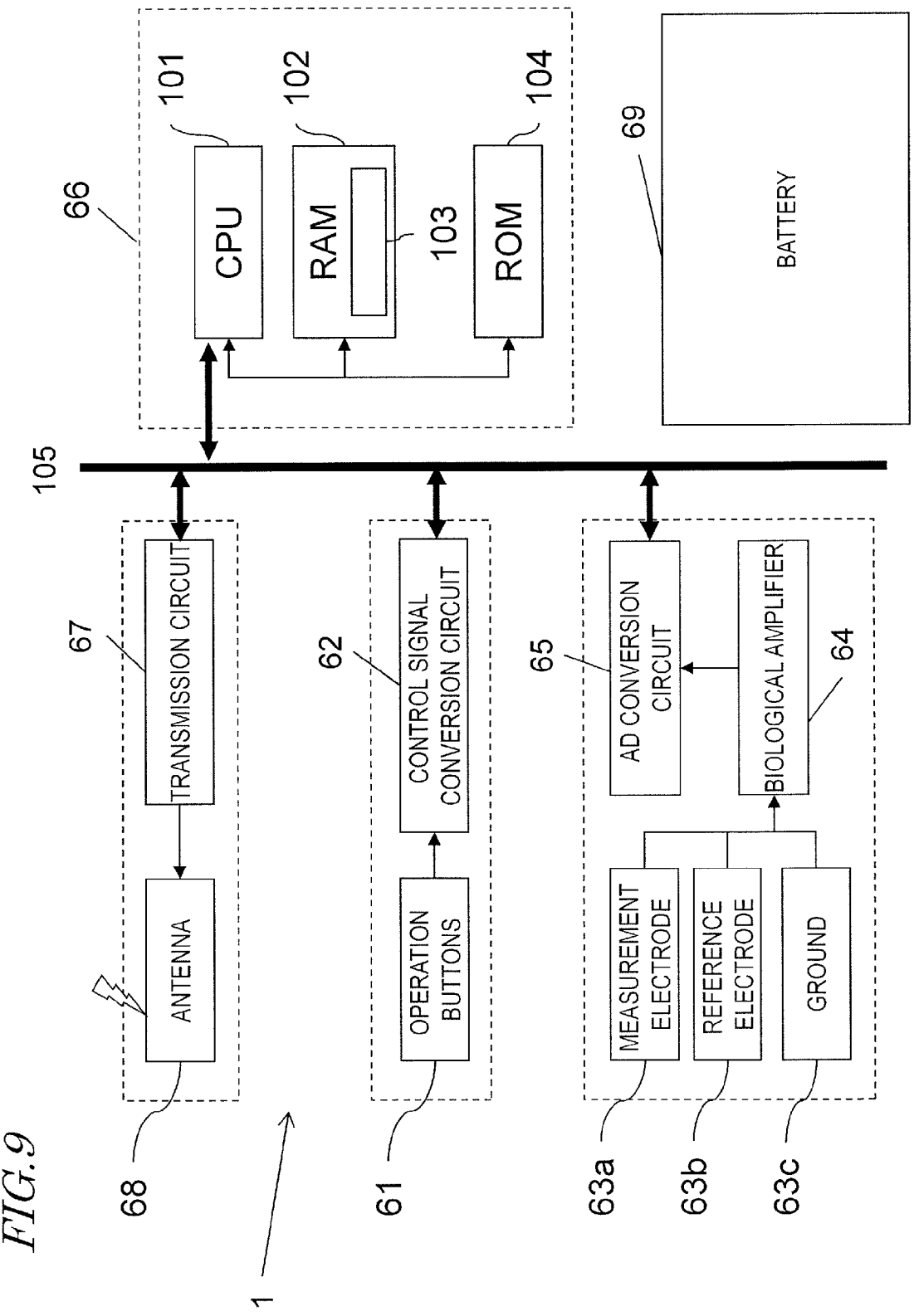

FIG. 9 is a diagram showing the hardware construction of a controller.

Figure 10:
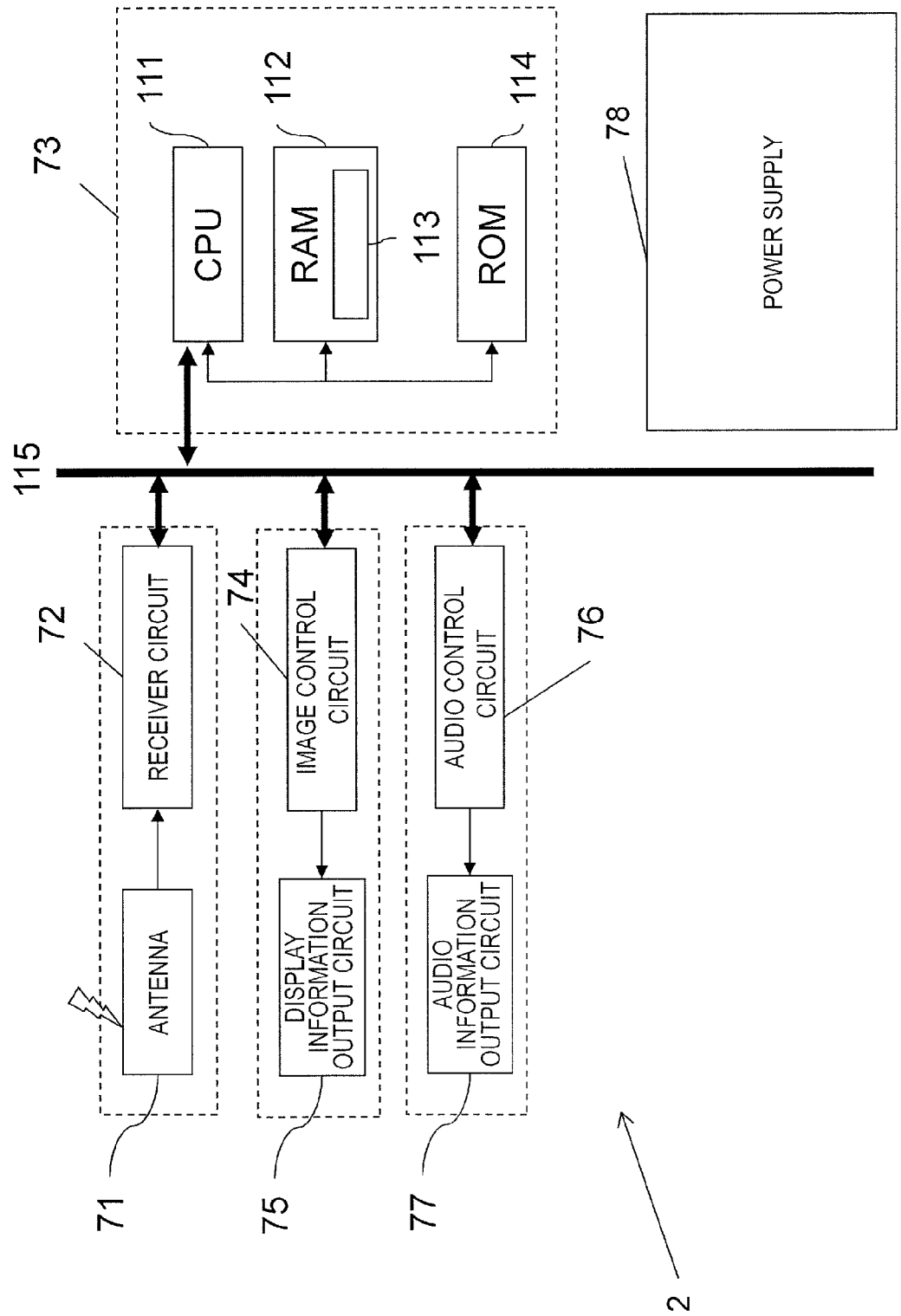

FIG. 10 is a diagram showing a hardware construction for the information processing system.

Figure 11:
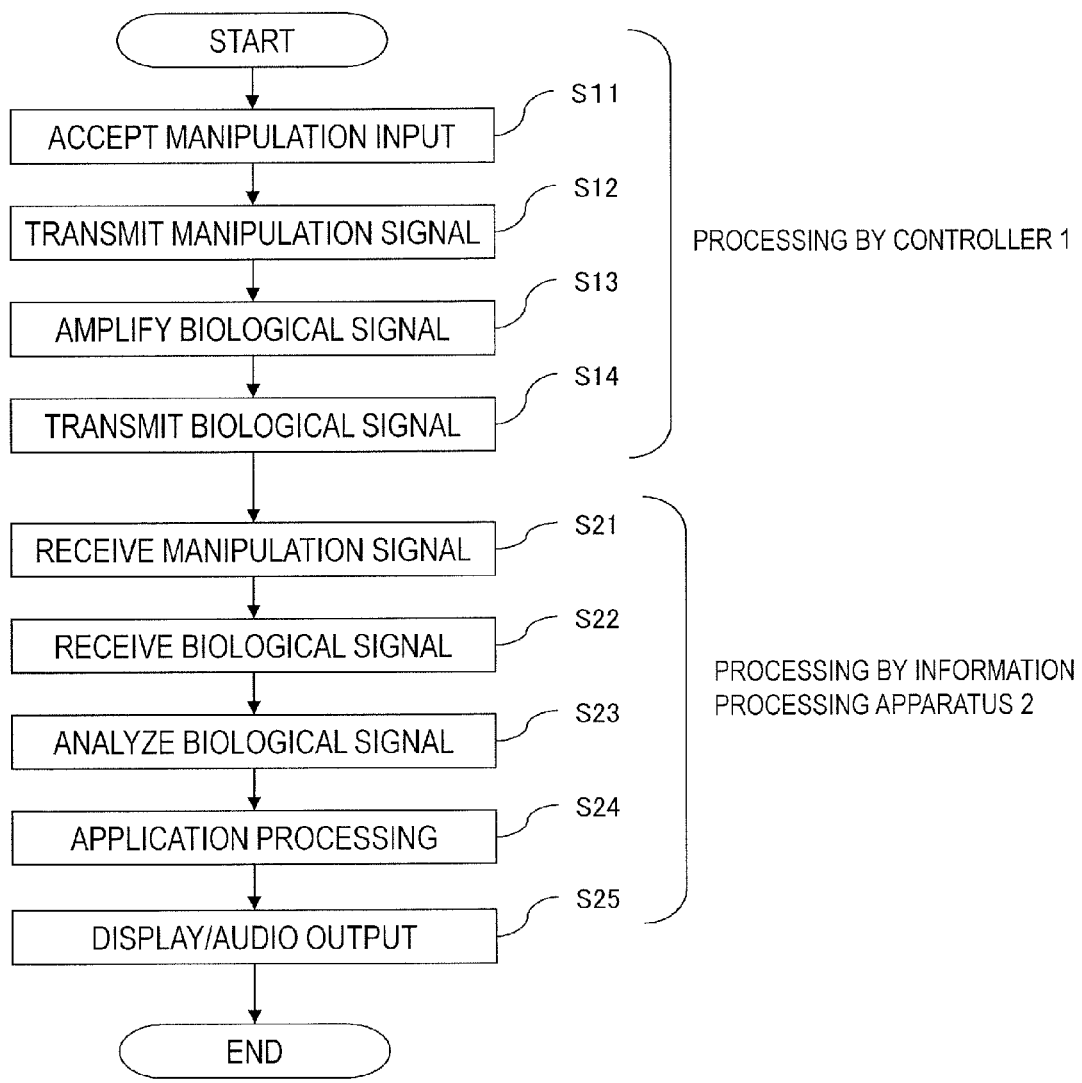

FIG. 11 is a diagram showing a flow of fundamental processes by the information processing system.

Figure 12A:
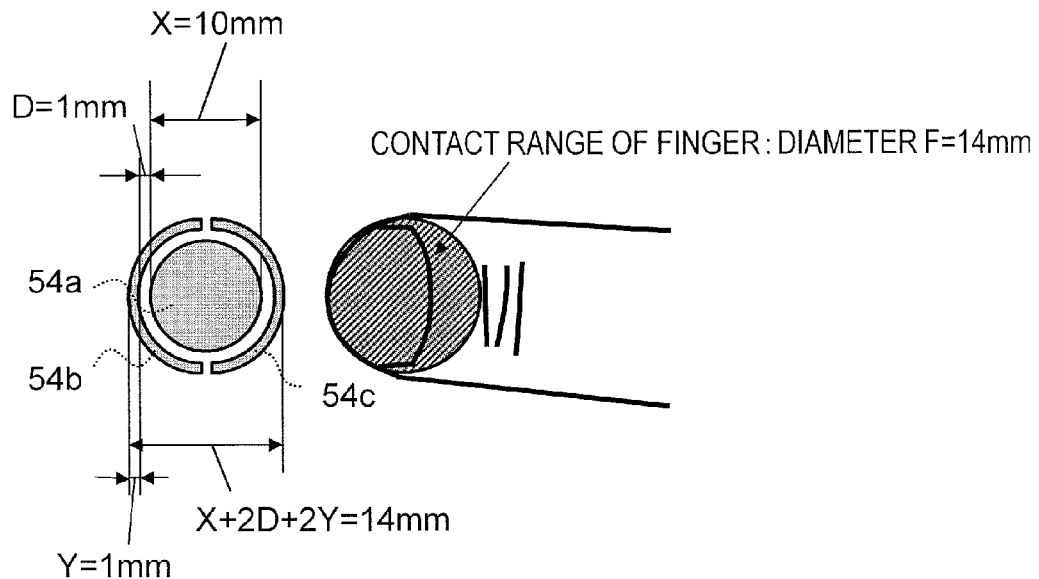
Figure 12B:
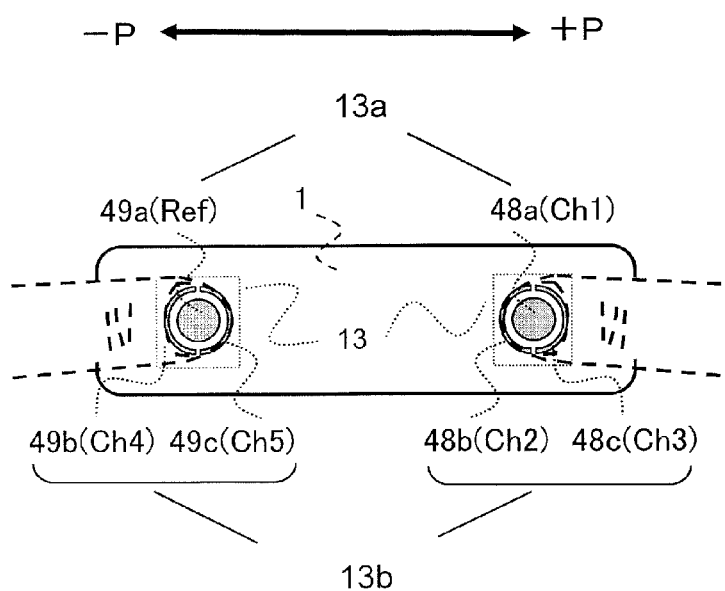

FIGS. 12A and 12B are diagrams showing electrode positioning according to Embodiment 1.

Figure 13:
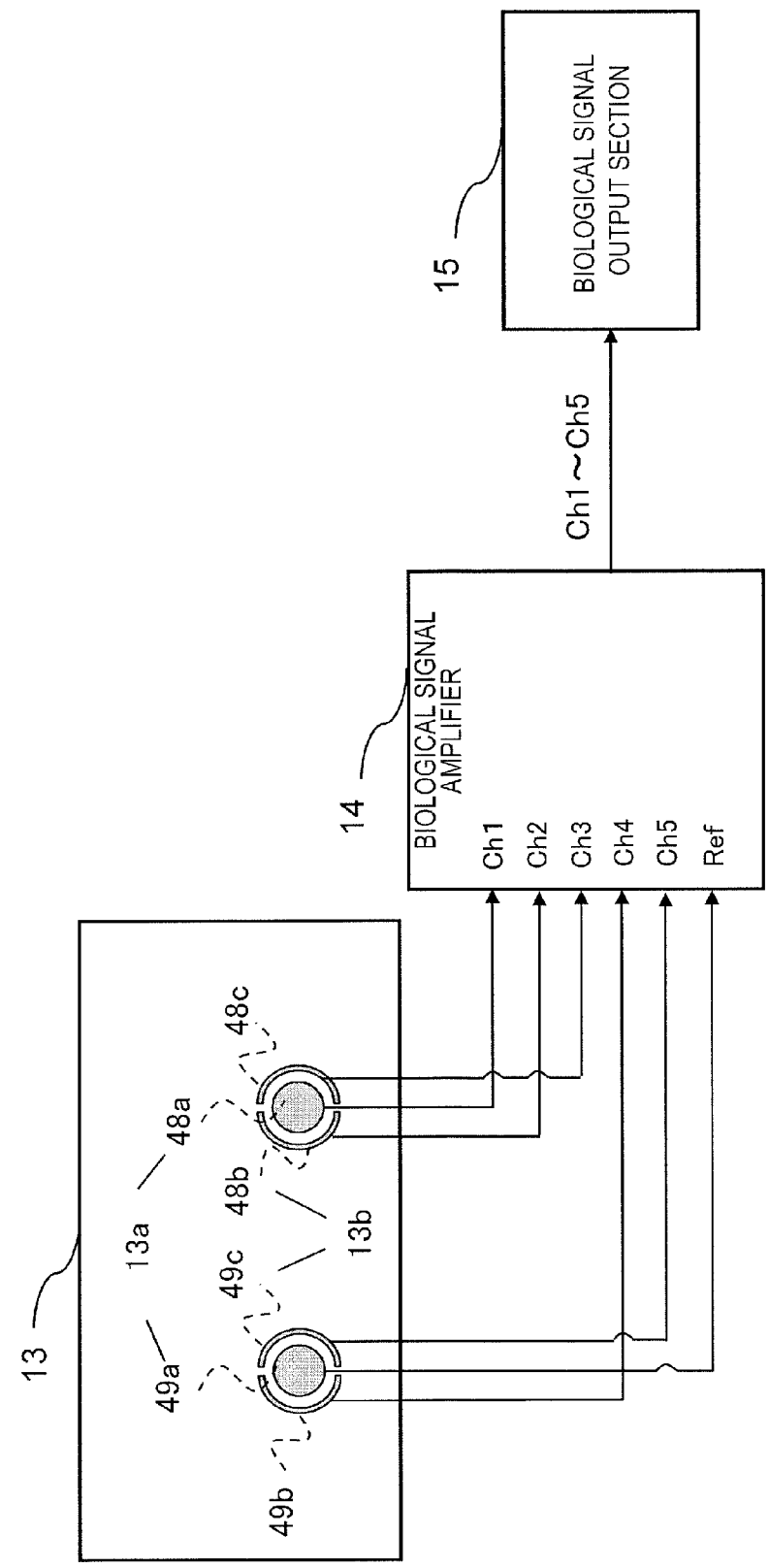

FIG. 13 is a diagram showing connection between an electrode section and a biological signal amplifier according to Embodiment 1.

Figure 14:
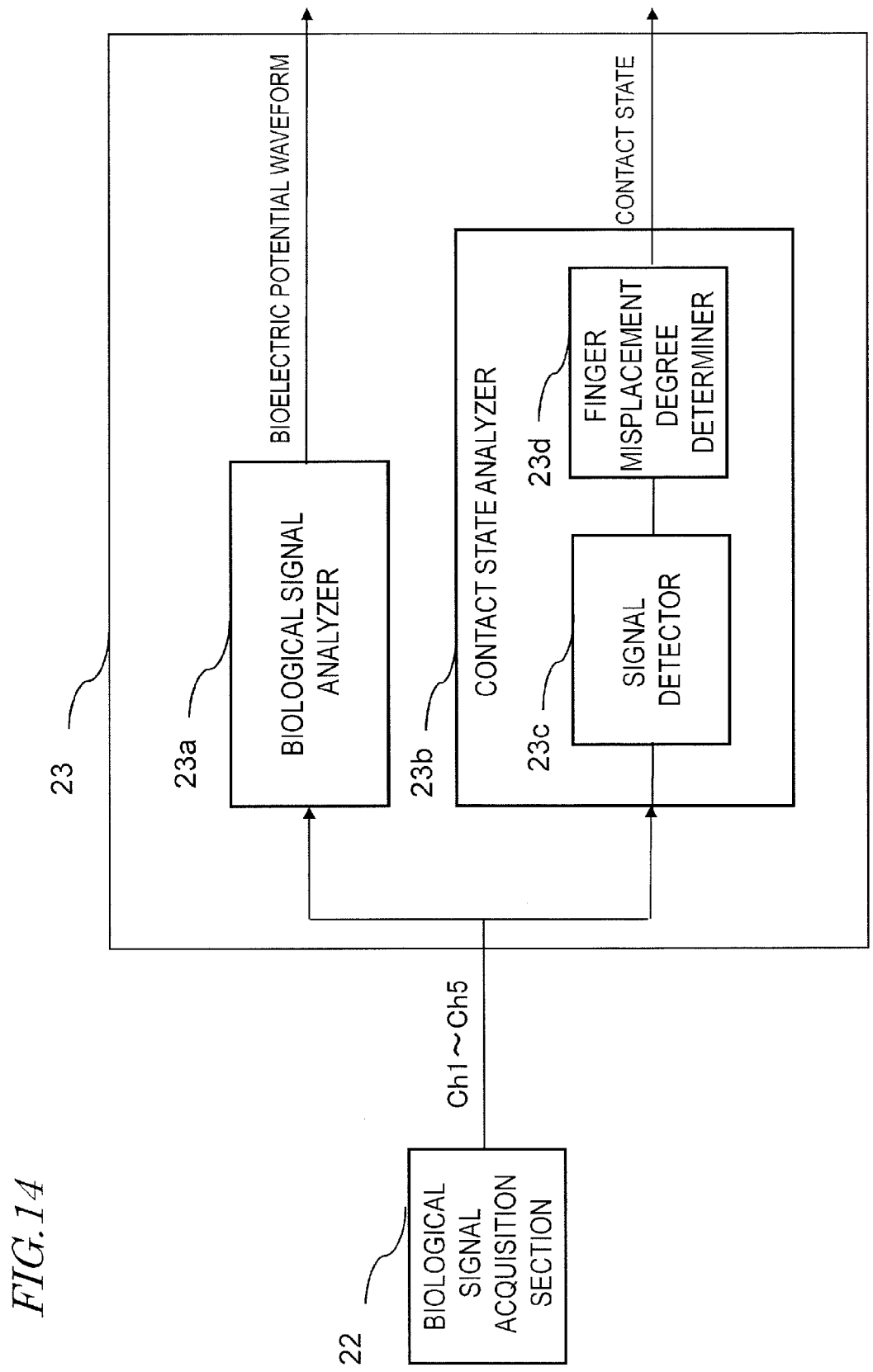

FIG. 14 is a diagram showing the construction of a biological signal processor according to Embodiment 1.

Figure 15:
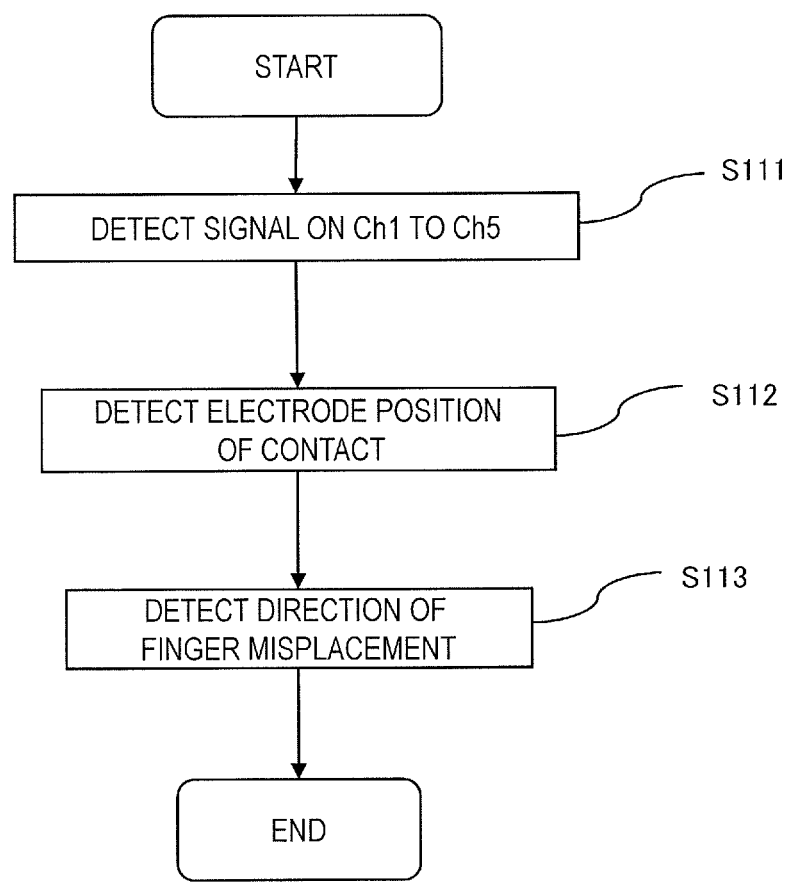

FIG. 15 is a diagram showing a flow of processing by a contact state analyzer according to Embodiment 1.

FIGS. 16A to 16D are diagrams showing states of finger misplacement in Embodiment 1.

FIG. 17 is a diagram showing a flow of processing by a signal detector according to Embodiment 1.

FIG. 18 is a diagram showing a lookup table of signal detection according to Embodiment 1.

Figure 19:
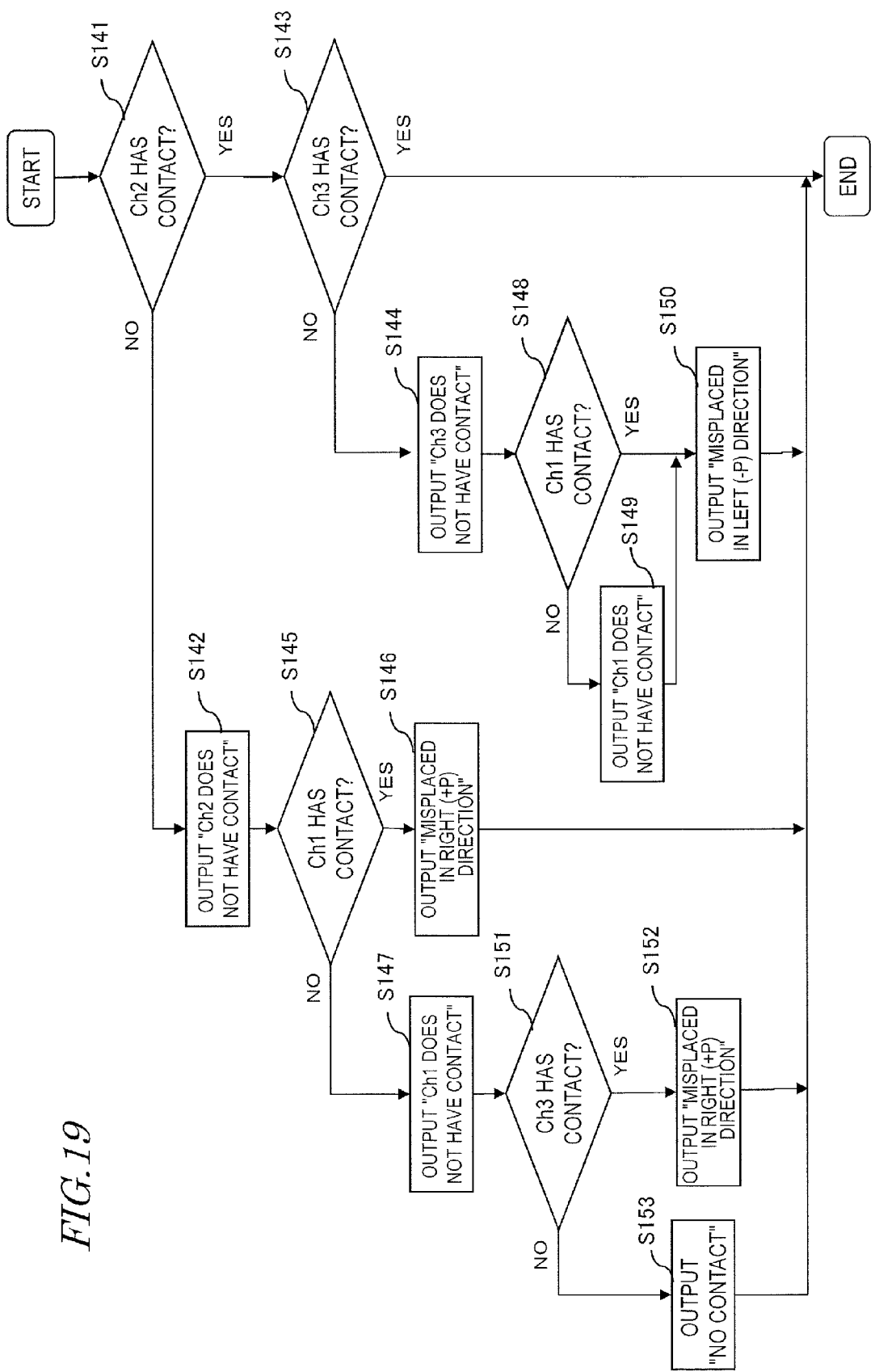

FIG. 19 is a diagram showing a flow of processing by a finger misplacement degree determiner 23d according to Embodiment 1.

Figure 20A:
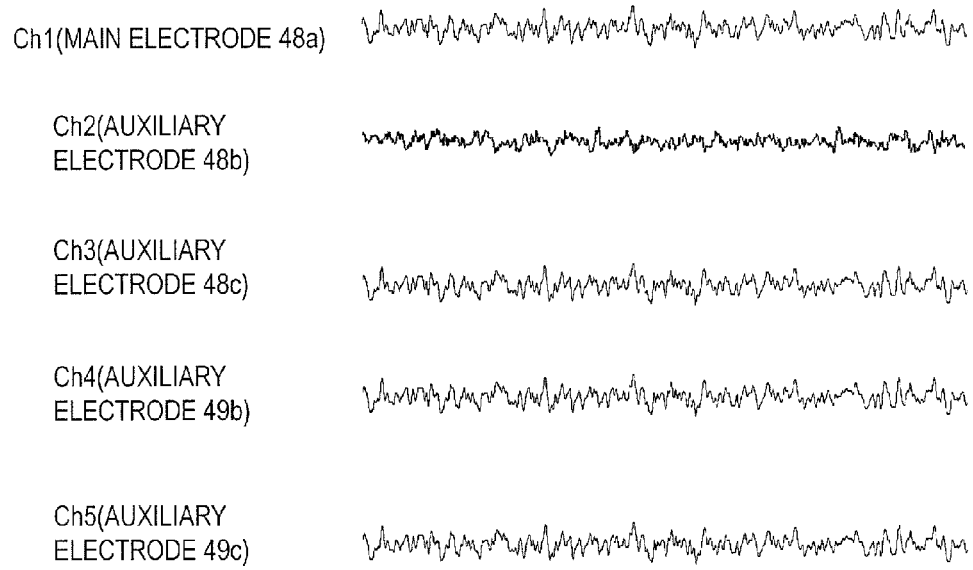

FIG. 20A is a diagram showing exemplary data in a first state of finger misplacement (first state) according to Embodiment 1.

Figure 20B:
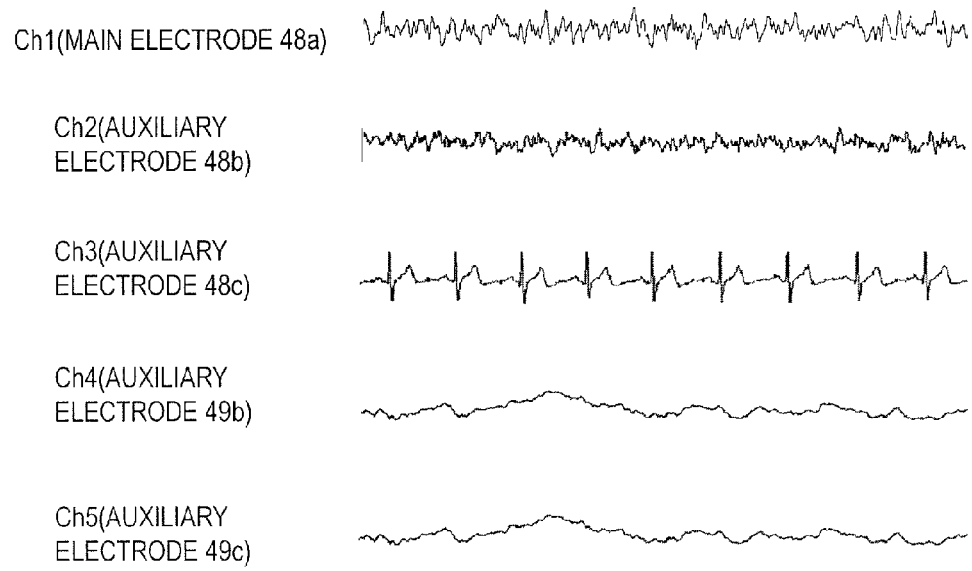

FIG. 20B is a diagram showing exemplary data in a second state of finger misplacement (second state) according to Embodiment 1.

FIG. 20C is a diagram showing exemplary data in a third state of finger misplacement (third state) according to Embodiment 1.

FIG. 20D is a diagram showing exemplary data in a fourth state of finger misplacement (fourth state) according to Embodiment 1.

Figure 21:
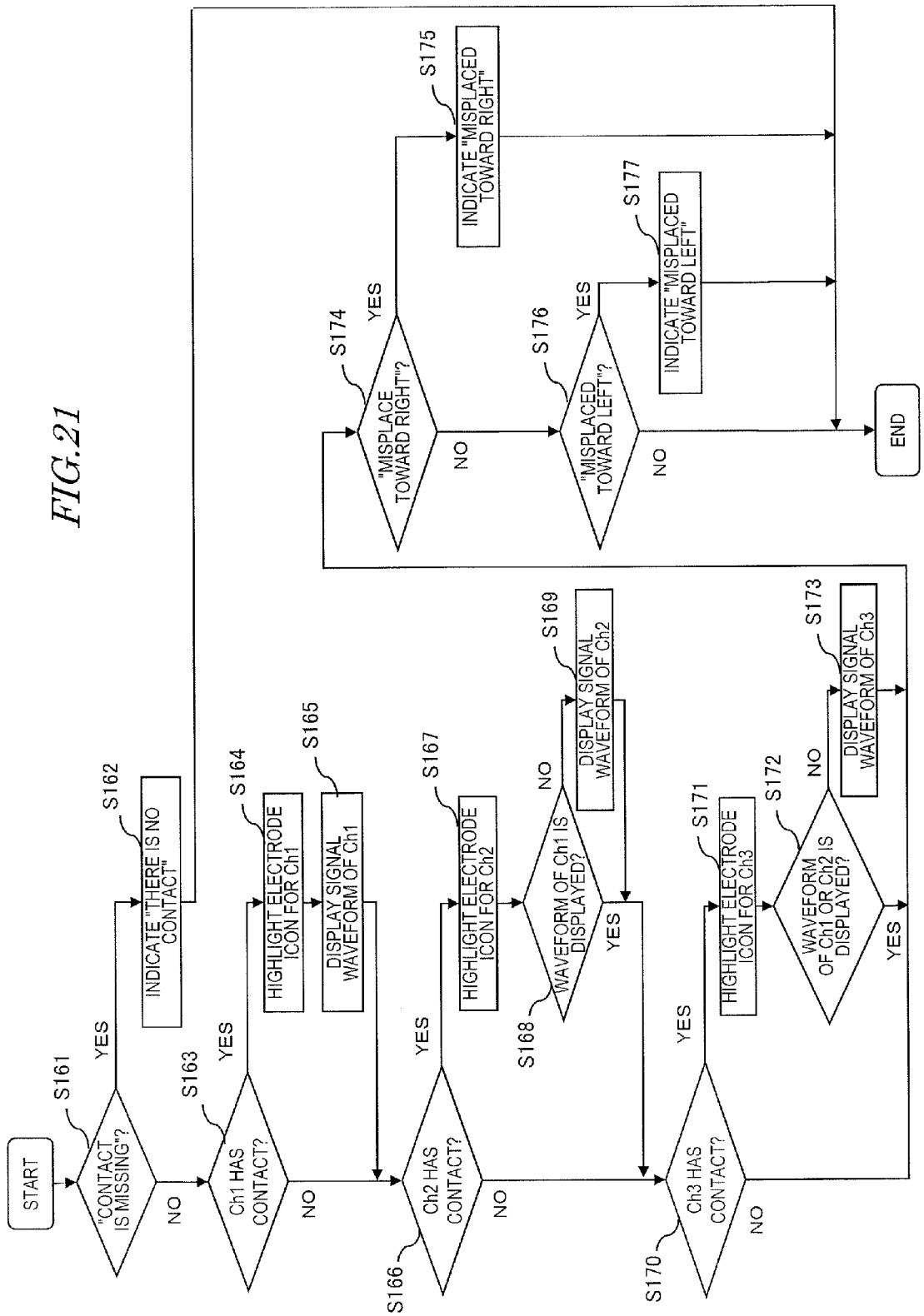

FIG. 21 is a diagram showing a flow of processing by an application processor according to Embodiment 1.

Figure 22:
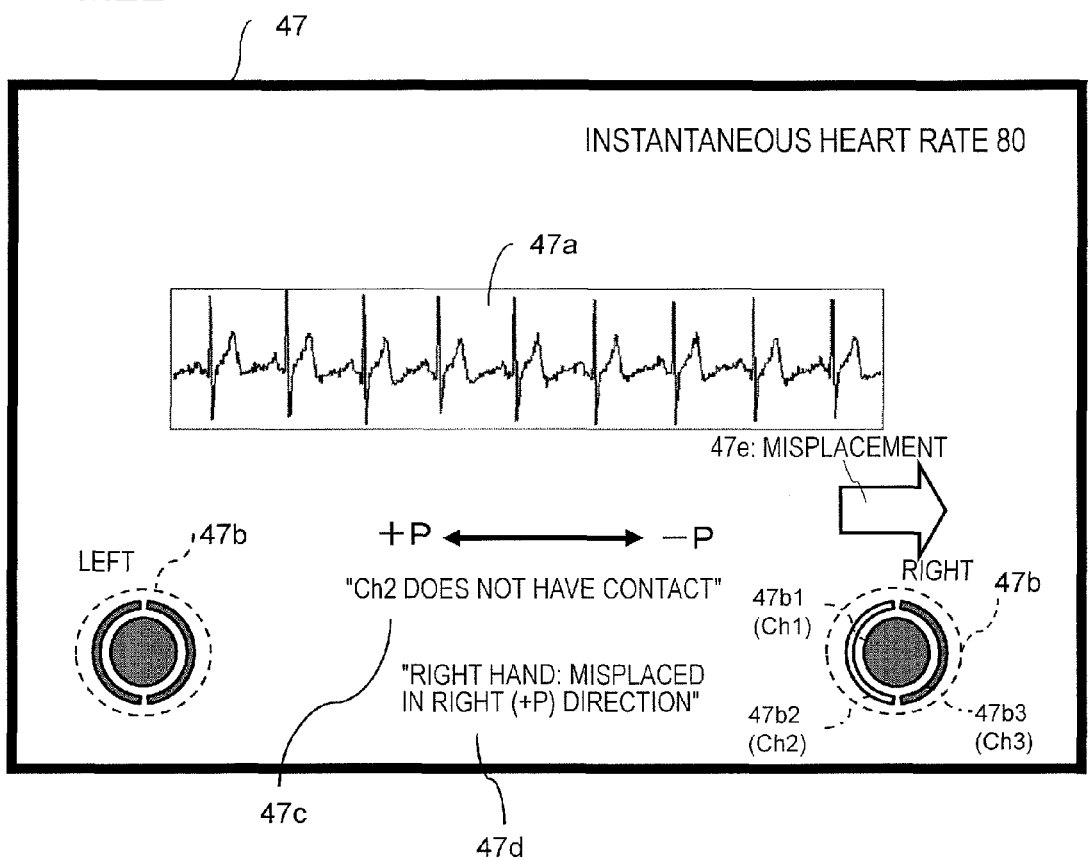

FIG. 22 is a diagram showing a display screen equipment according to Embodiment 1.

Figure 23:
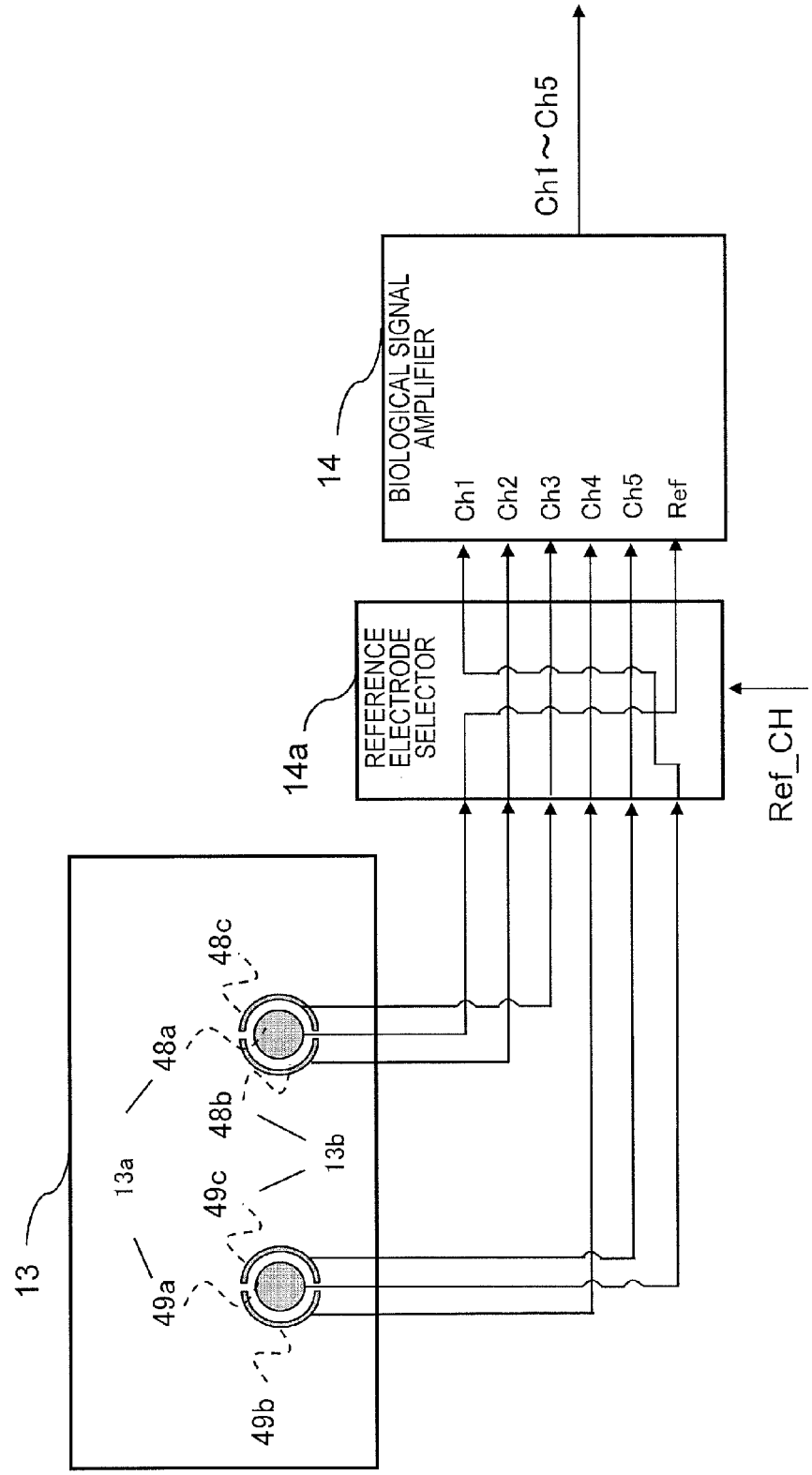

FIG. 23 is a diagram showing the construction of a reference electrode selector according to another example of Embodiment 1.

Figure 24:
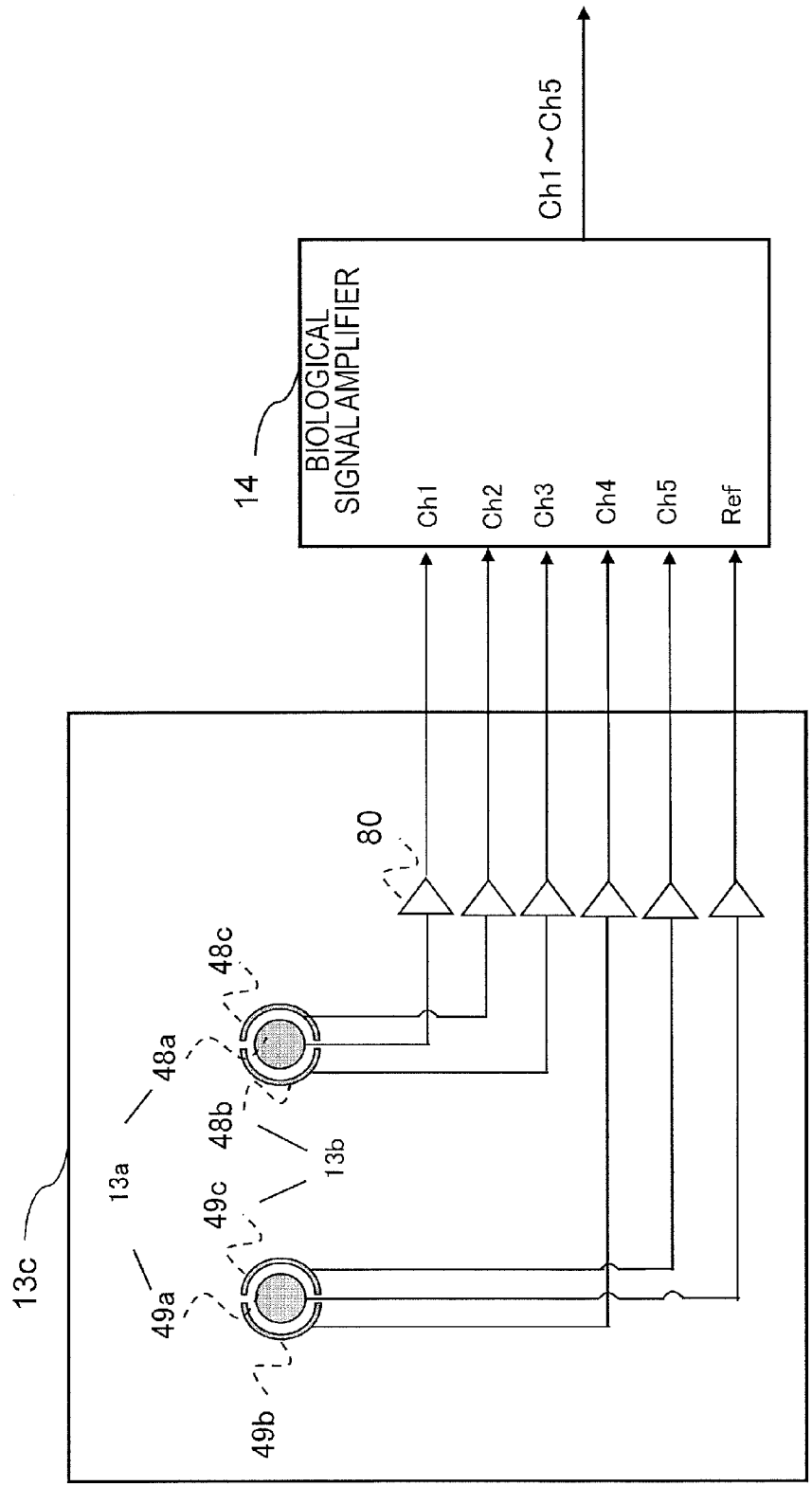

FIG. 24 is a diagram showing the construction of an active electrode section according to another example of Embodiment 1.

Figure 25:
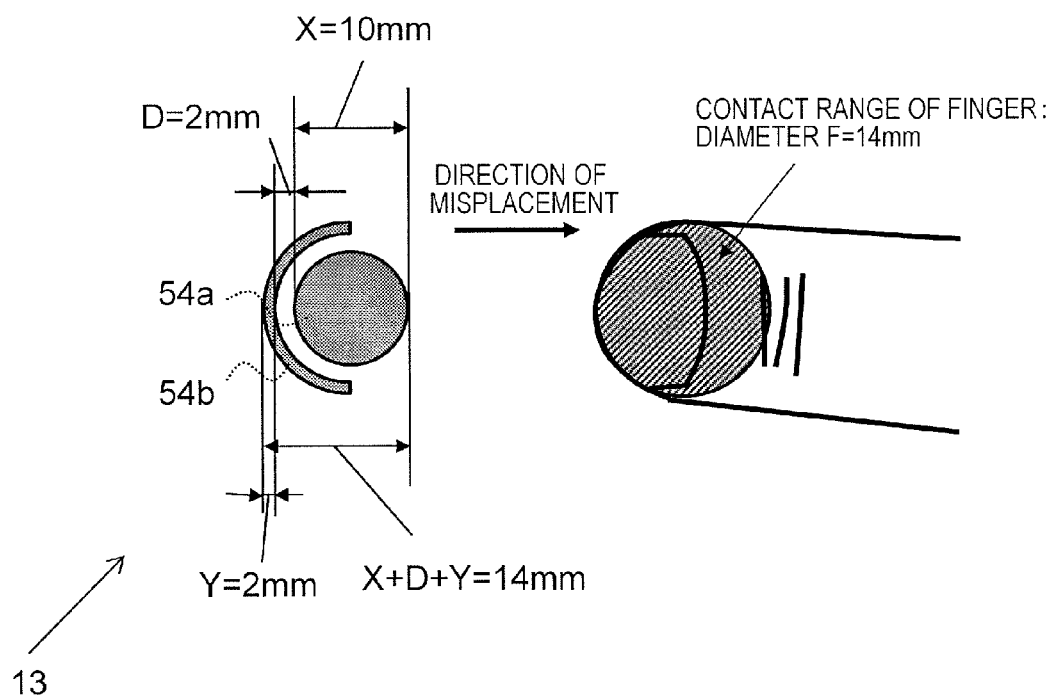

FIG. 25 is a diagram showing electrode positioning according to another example of Embodiment 1.

Figure 26A:
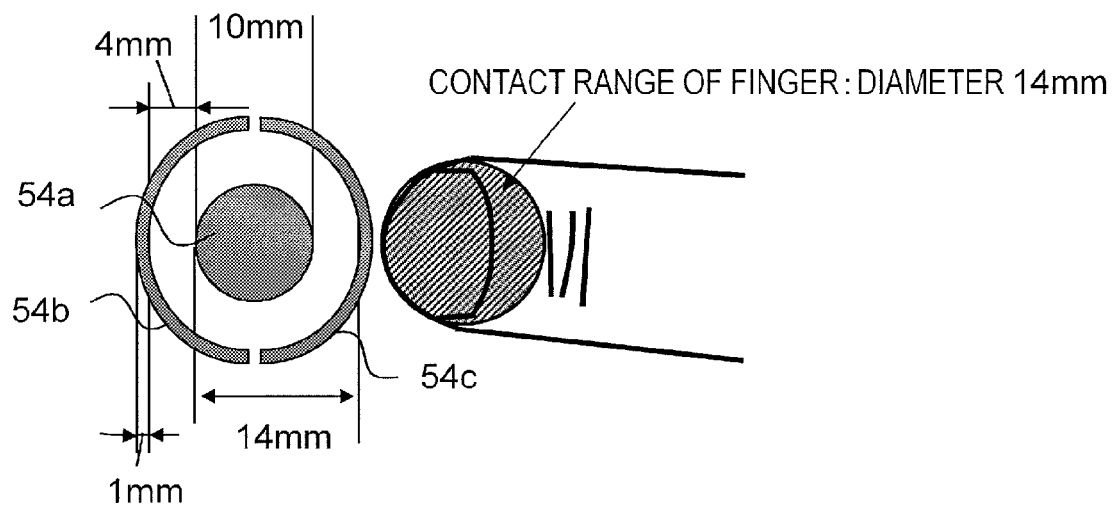
Figure 26B:
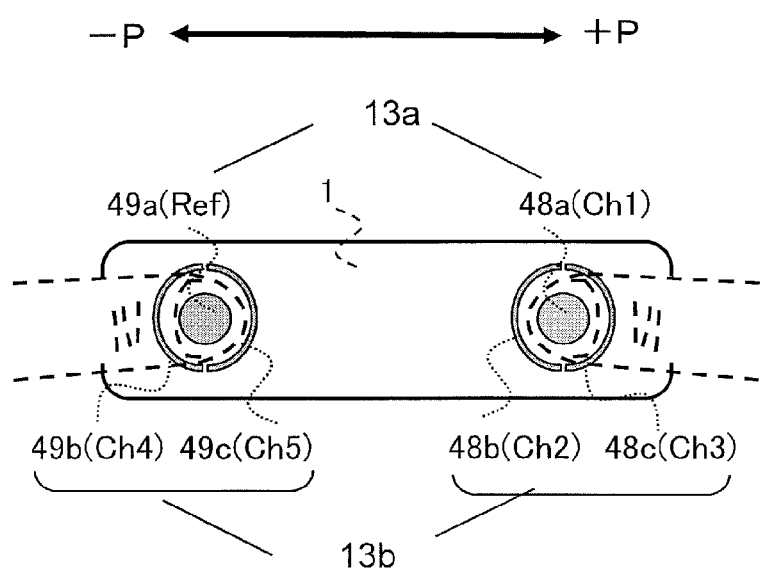

FIGS. 26A and 26B are diagrams showing electrode positioning according to another example of Embodiment 1.

FIGS. 27A to 27D are diagrams showing electrode positioning according to other examples of Embodiment 1.

FIGS. 28A to 28D are diagrams showing electrode positioning according to other examples of Embodiment 1.

FIGS. 29A to 29D are diagrams showing electrode positioning according to other examples of Embodiment 1.

Figure 30:
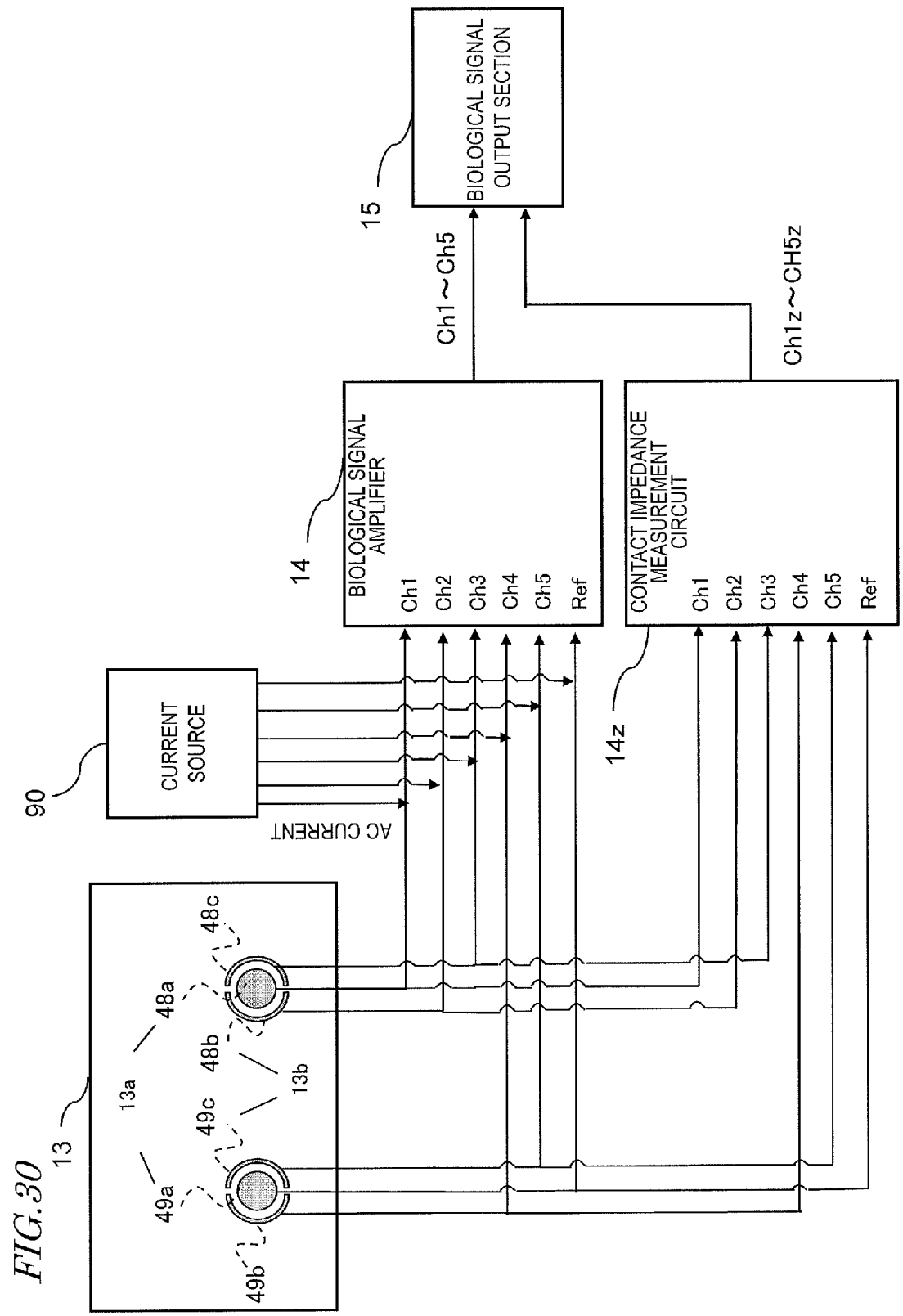

FIG. 30 is a diagram showing connection between an electrode section and a biological signal amplifier according to another example of Embodiment 1.

Figure 31:
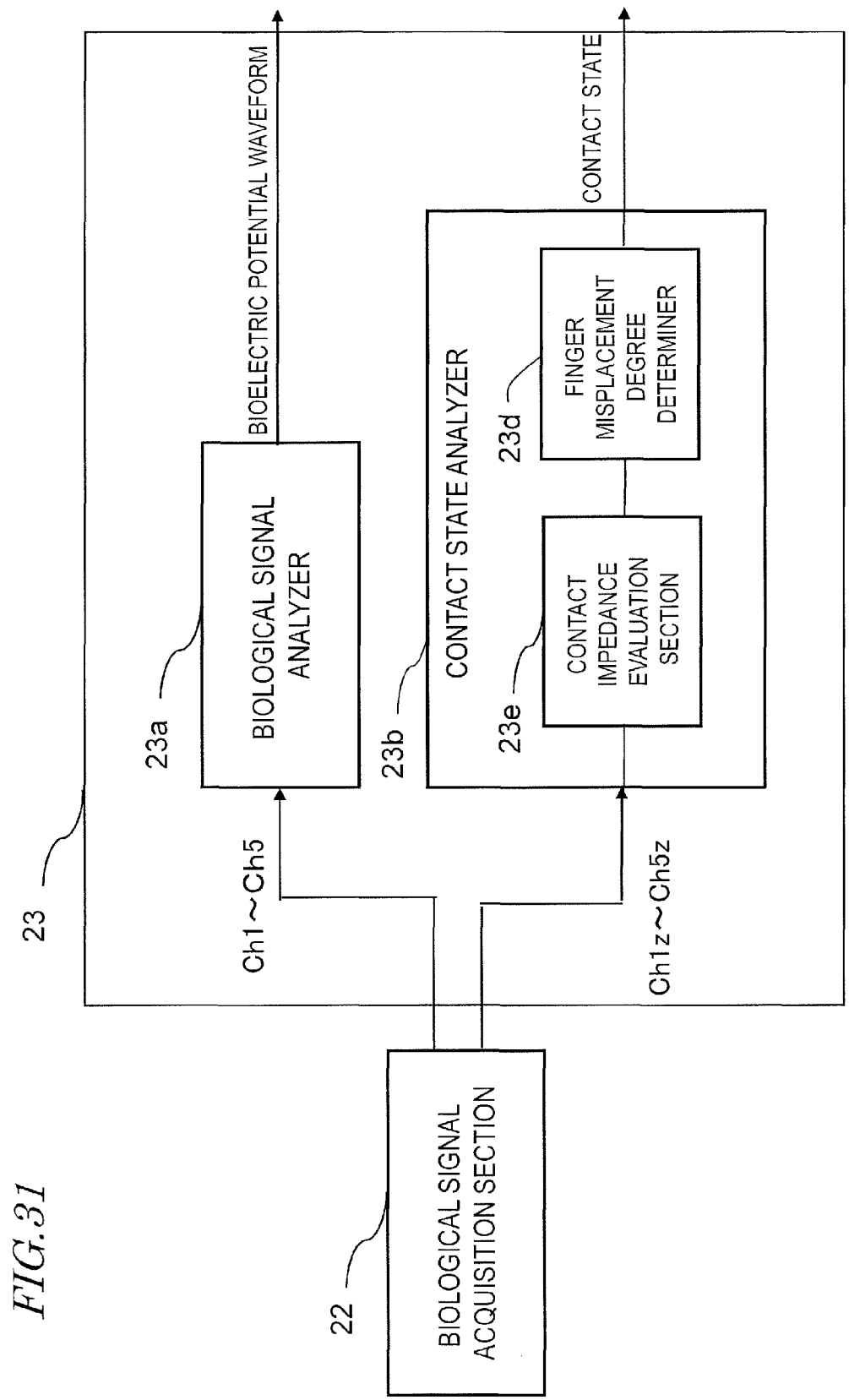

FIG. 31 is a diagram showing the construction of a biological signal processor according to another example of Embodiment 1.

FIG. 32 is a diagram showing a lookup table of contact impedance measurement according to another example of Embodiment 1.

Figure 33A:
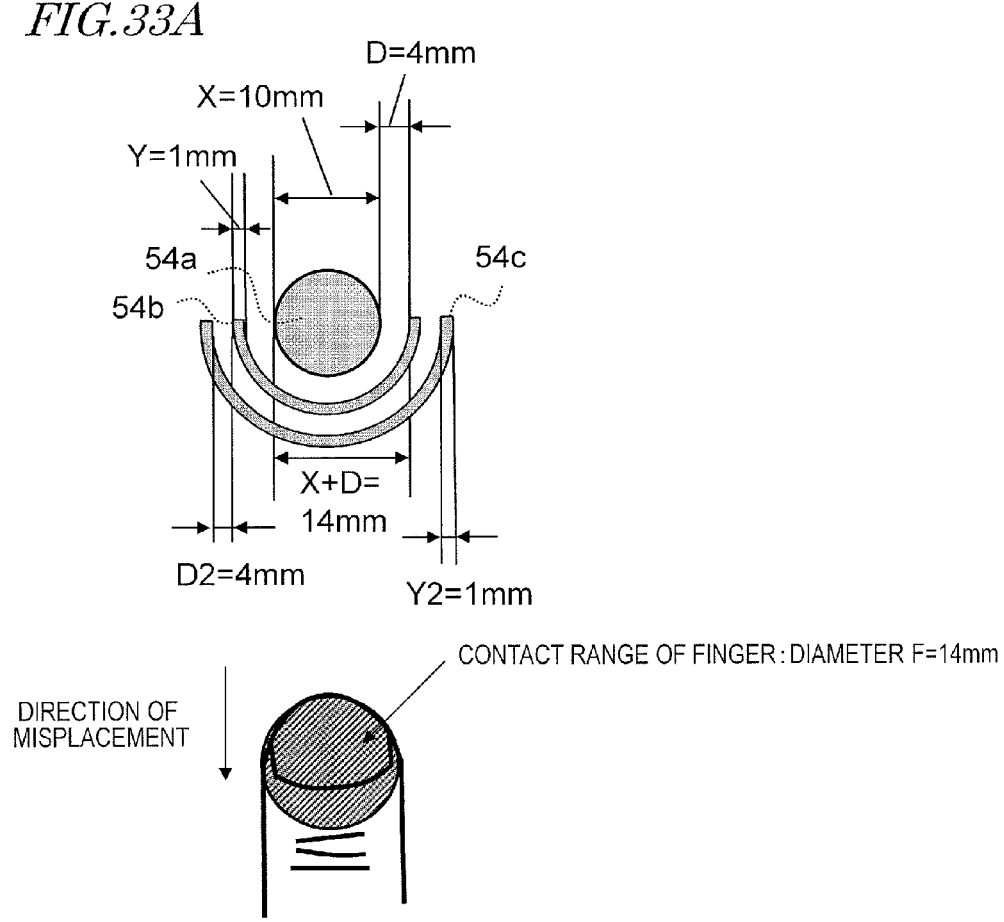
Figure 33B:
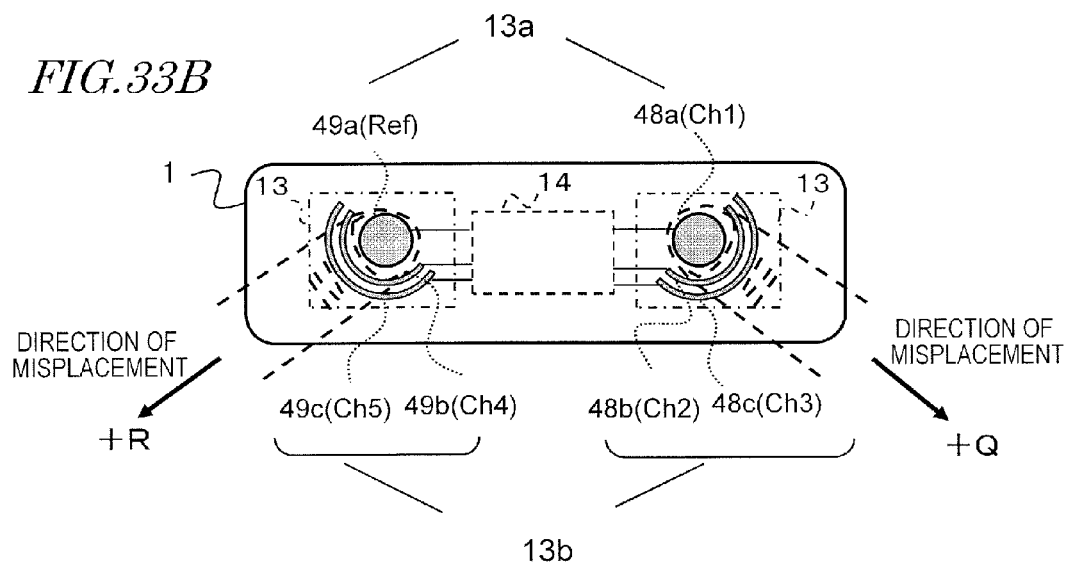

FIGS. 33A and 33B are diagrams showing electrode positioning according to Embodiment 2.

Figure 34:
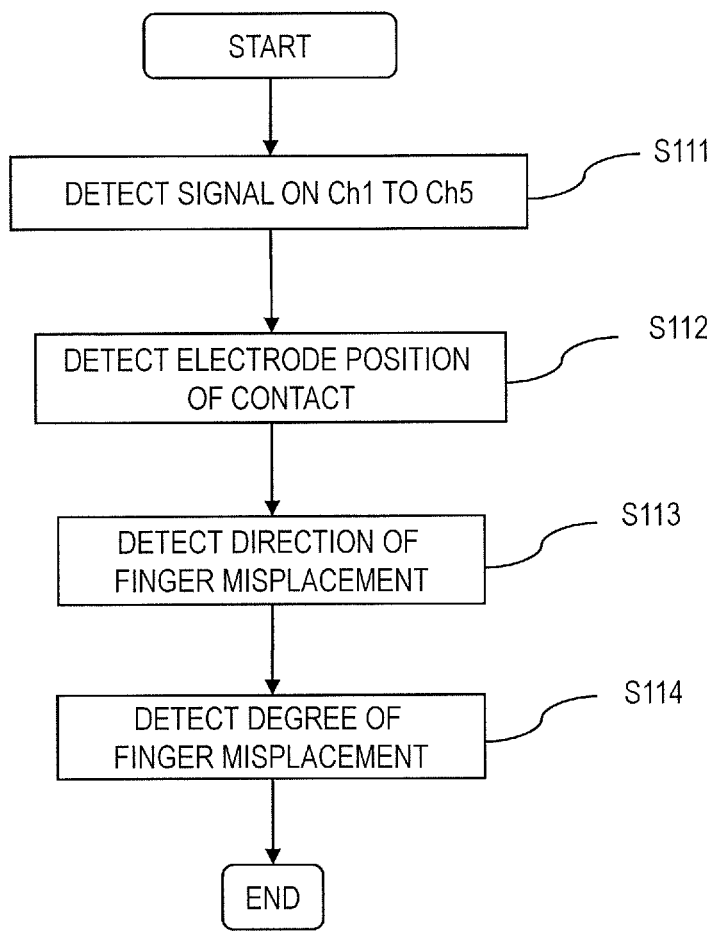

FIG. 34 is a diagram showing a contact state analyzer according to Embodiment 2.

Figure 35A:
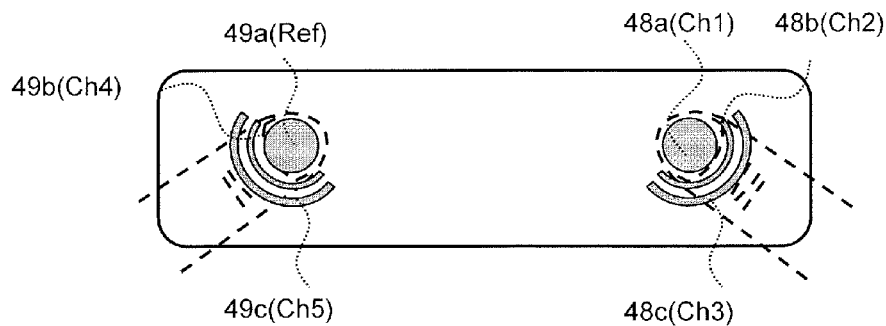
Figure 35B:
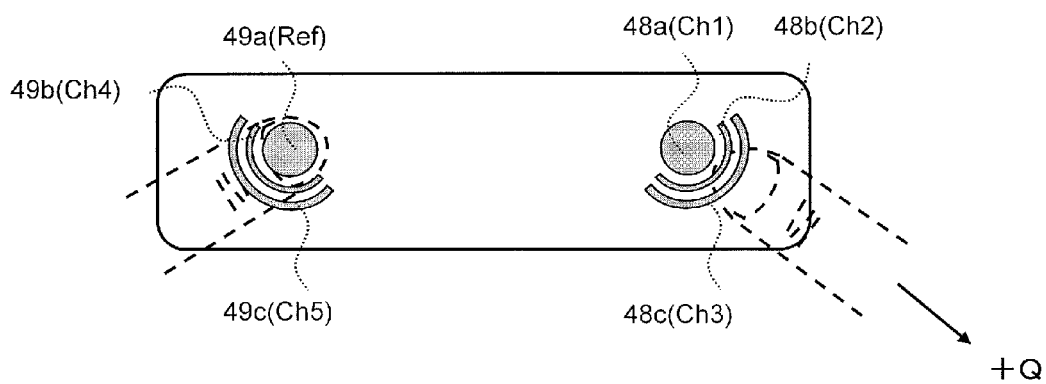
Figure 35C:
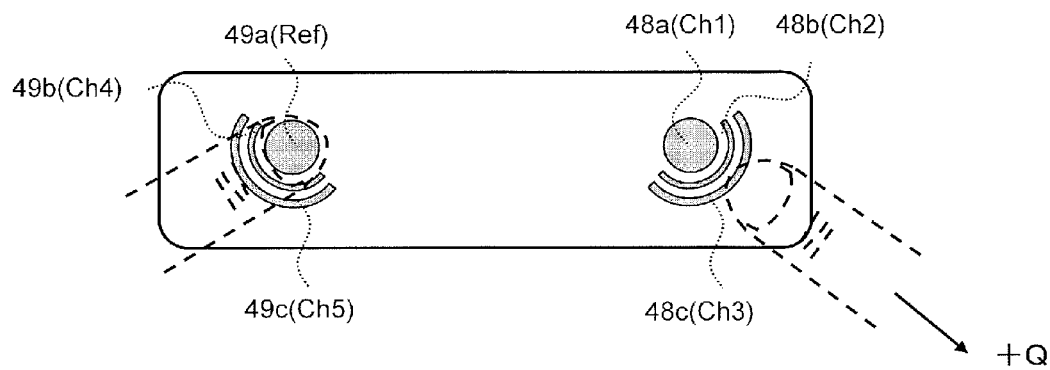

FIGS. 35A to 35C are diagrams showing exemplary states of finger misplacement in Embodiment 2.

FIG. 36 is a diagram showing a lookup table of signal detection and states of finger misplacement according to Embodiment 2.

Figure 37:
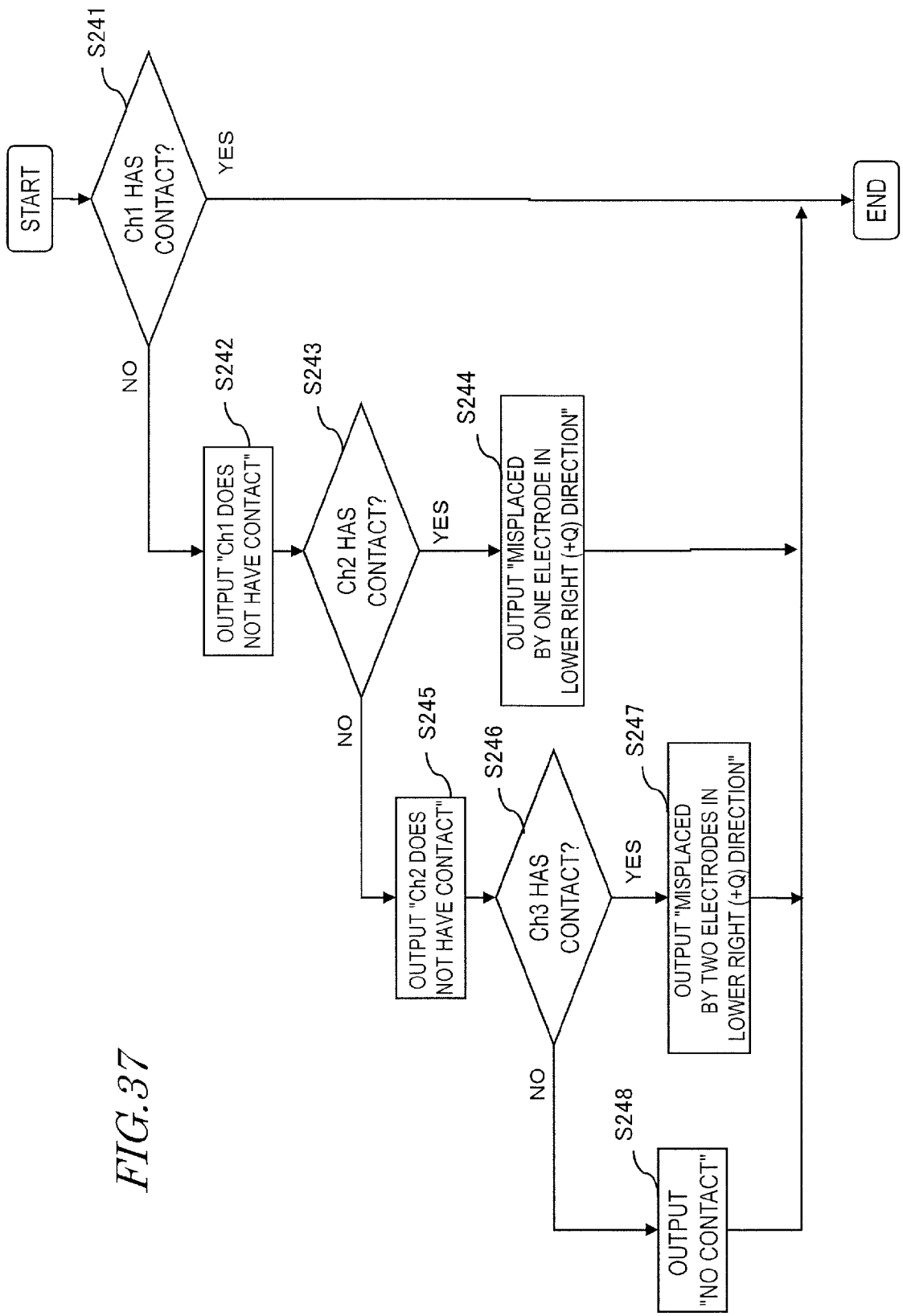

FIG. 37 is a diagram showing a flow of processing by a finger misplacement degree determiner 23d according to Embodiment 2.

Figure 38A:
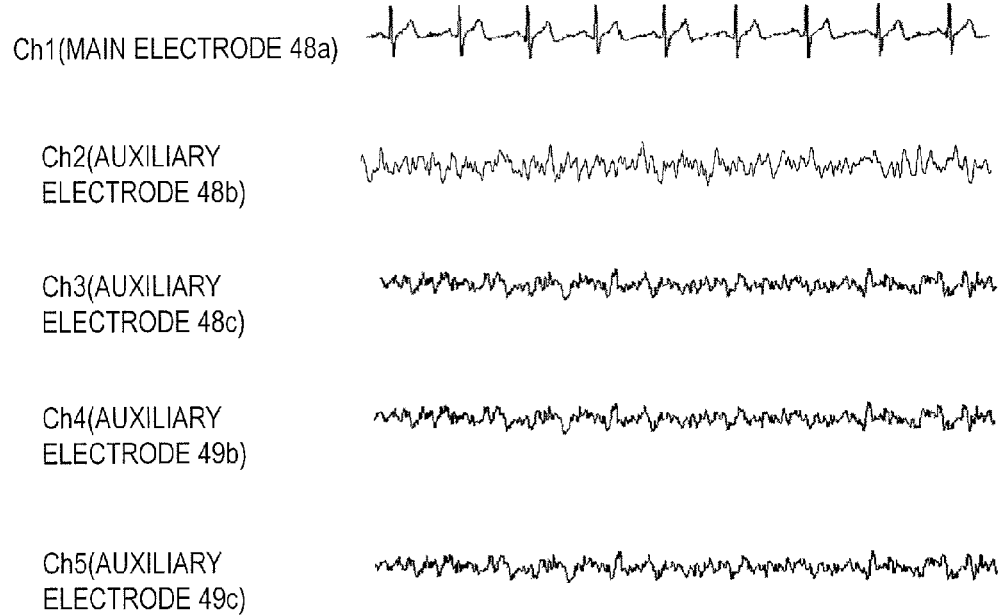

FIG. 38A is a diagram showing exemplary data in a first state of finger misplacement (first state) according to Embodiment 2.

Figure 38B:
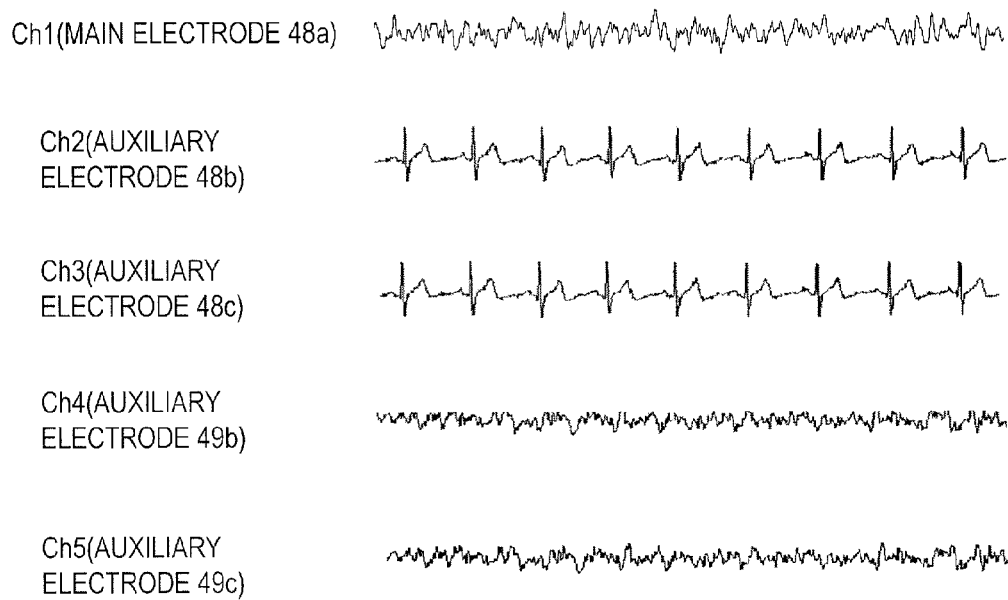

FIG. 38B is a diagram showing exemplary data in a second state of finger misplacement (second state) according to Embodiment 2.

Figure 38C:
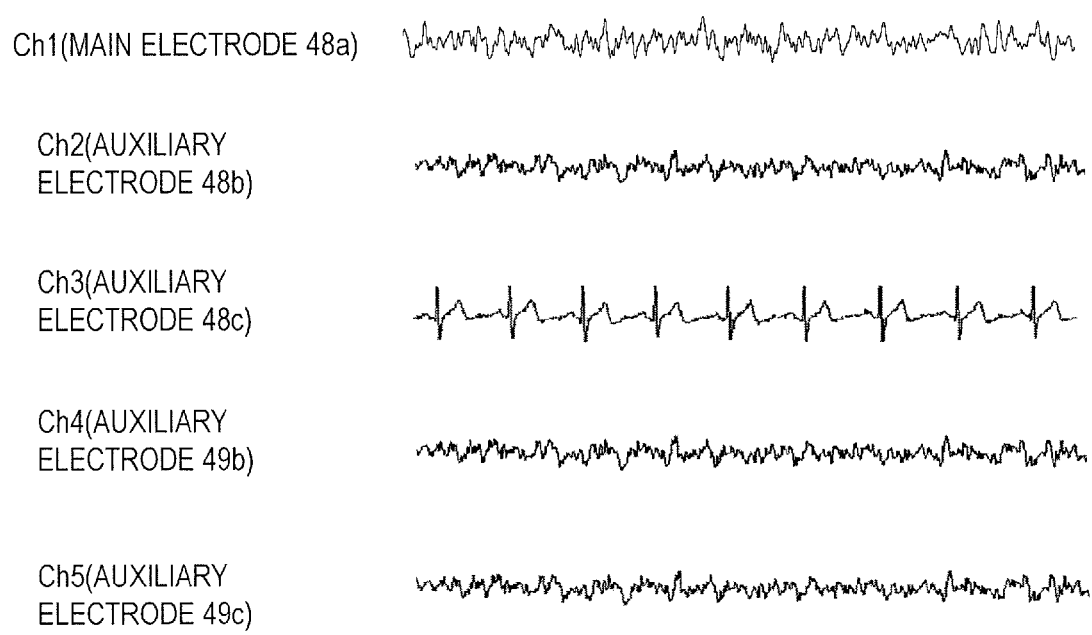

FIG. 38C is a diagram showing exemplary data in a third state of finger misplacement (third state) according to Embodiment 2.

Figure 39:
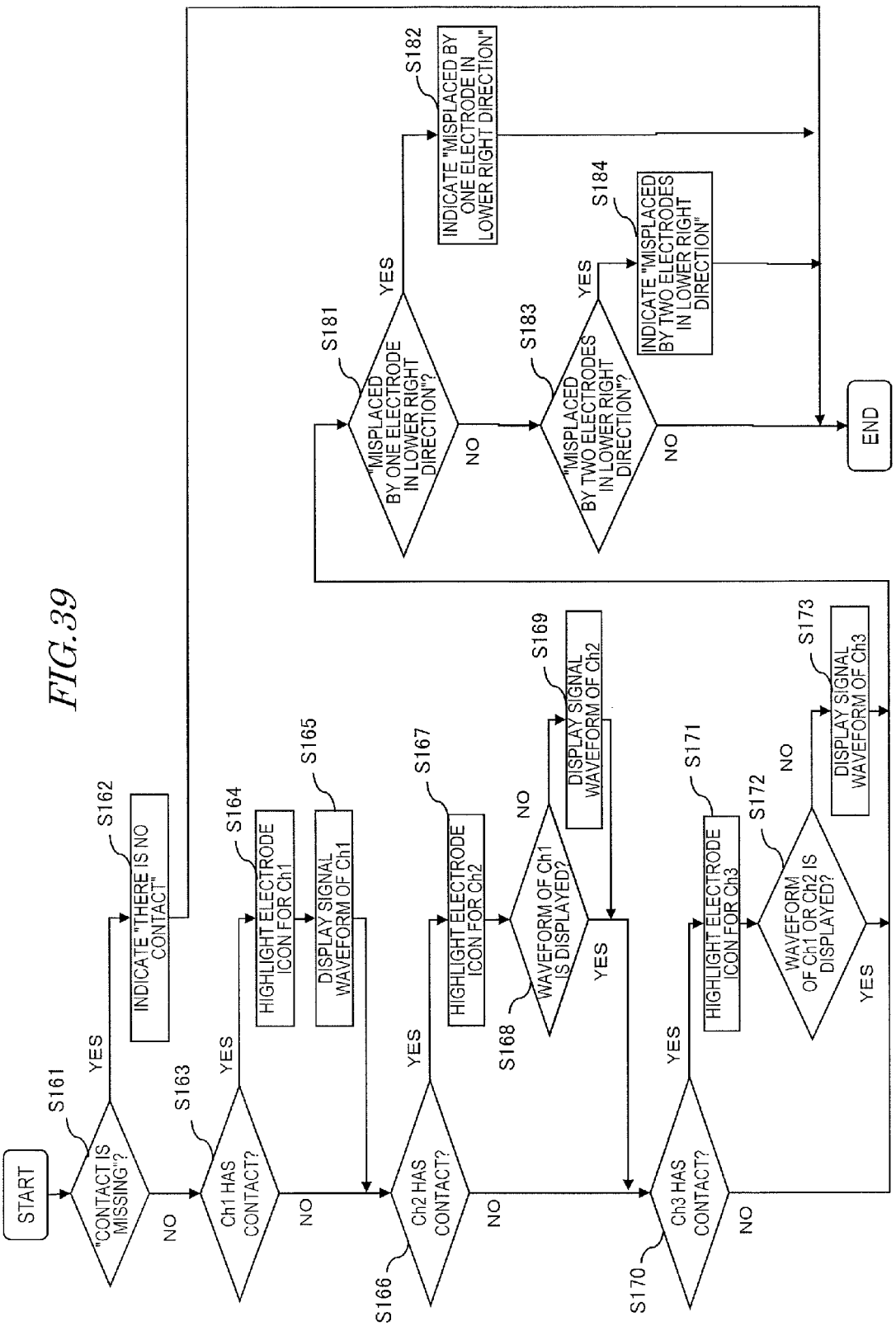

FIG. 39 is a diagram showing a flow of processing by an application processor according to Embodiment 2.

Figure 40:
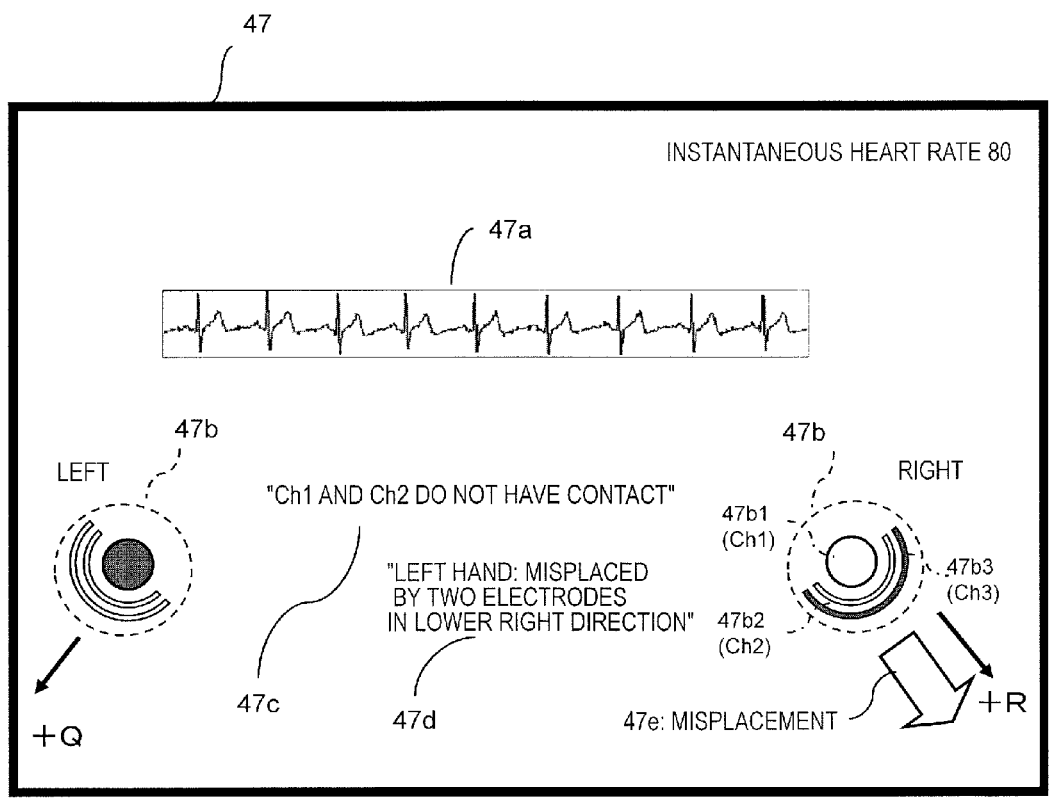

FIG. 40 is a diagram showing a display screen according to Embodiment 2.

Figure 41:
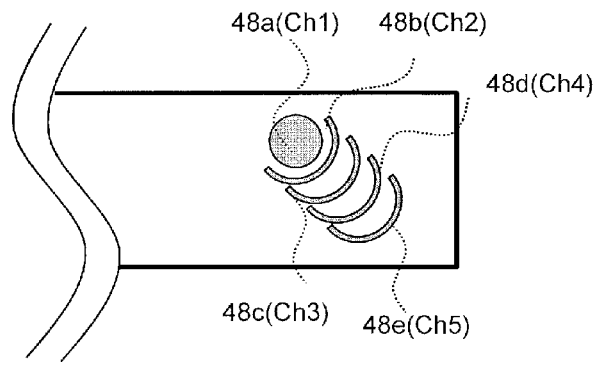

FIG. 41 is a diagram showing electrode positioning according to a variant of Embodiment 2.

Figure 42:
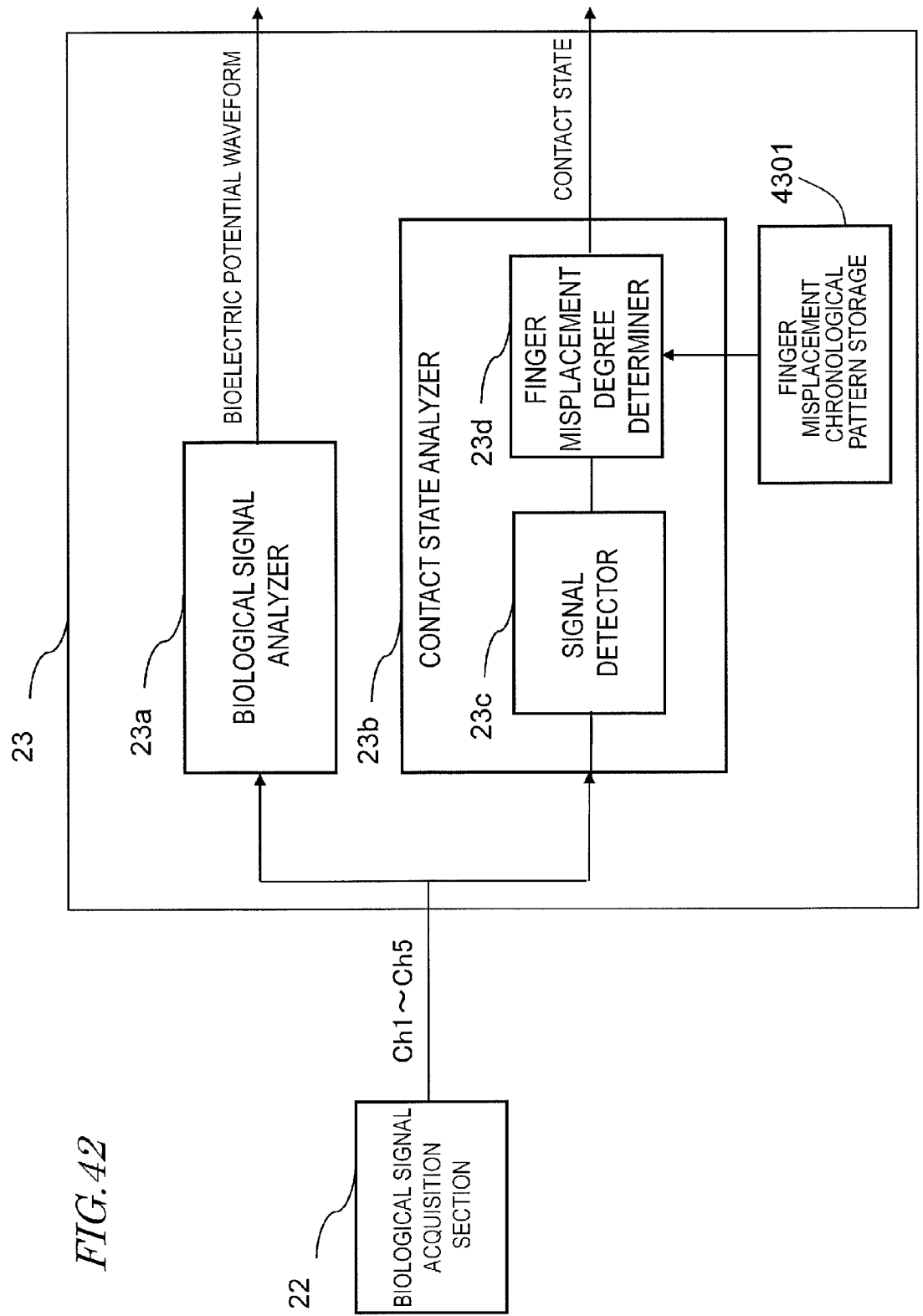

FIG. 42 is a diagram showing a system construction according to a variant of Embodiment 2.

FIGS. 43A and 43B are diagrams showing what is stored in a finger misplacement chronological pattern storing section according to a variant of Embodiment 2.

Figure 44A:
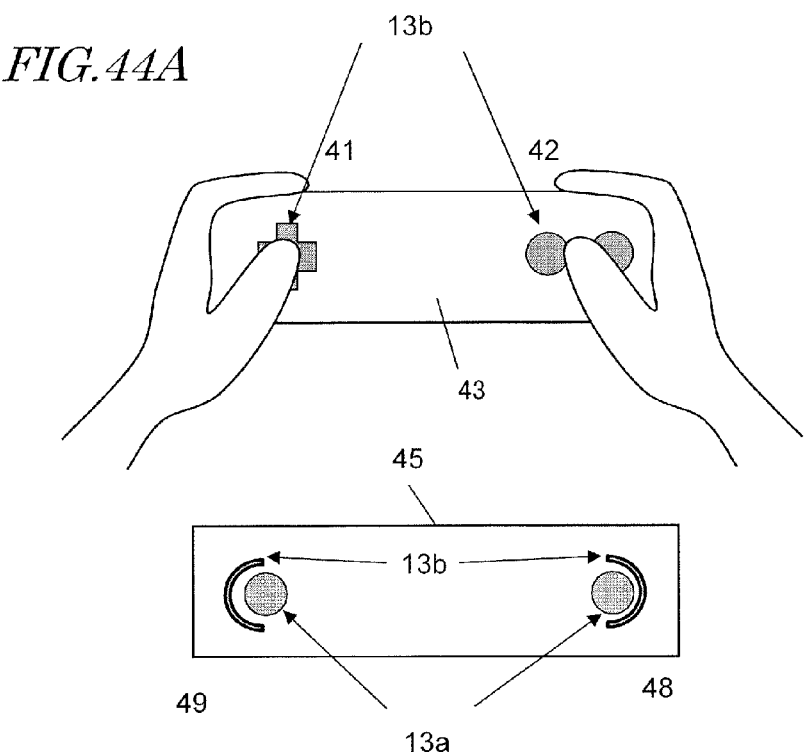
Figure 44B:
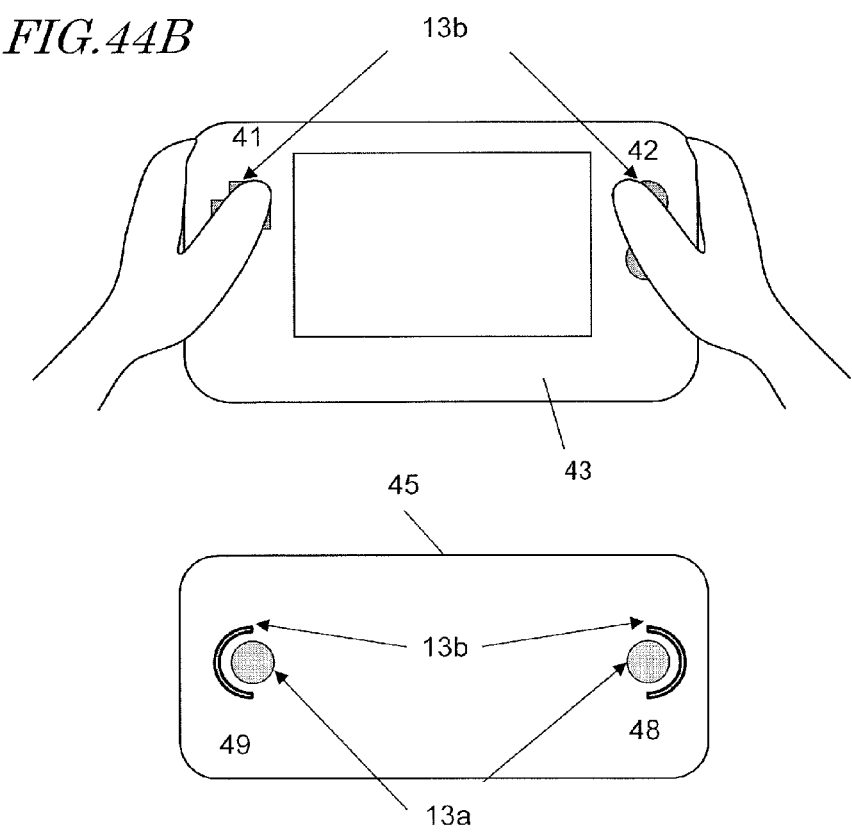

FIGS. 44A and 44B are diagrams showing electrode positioning according to Embodiment 3.

Figure 45:
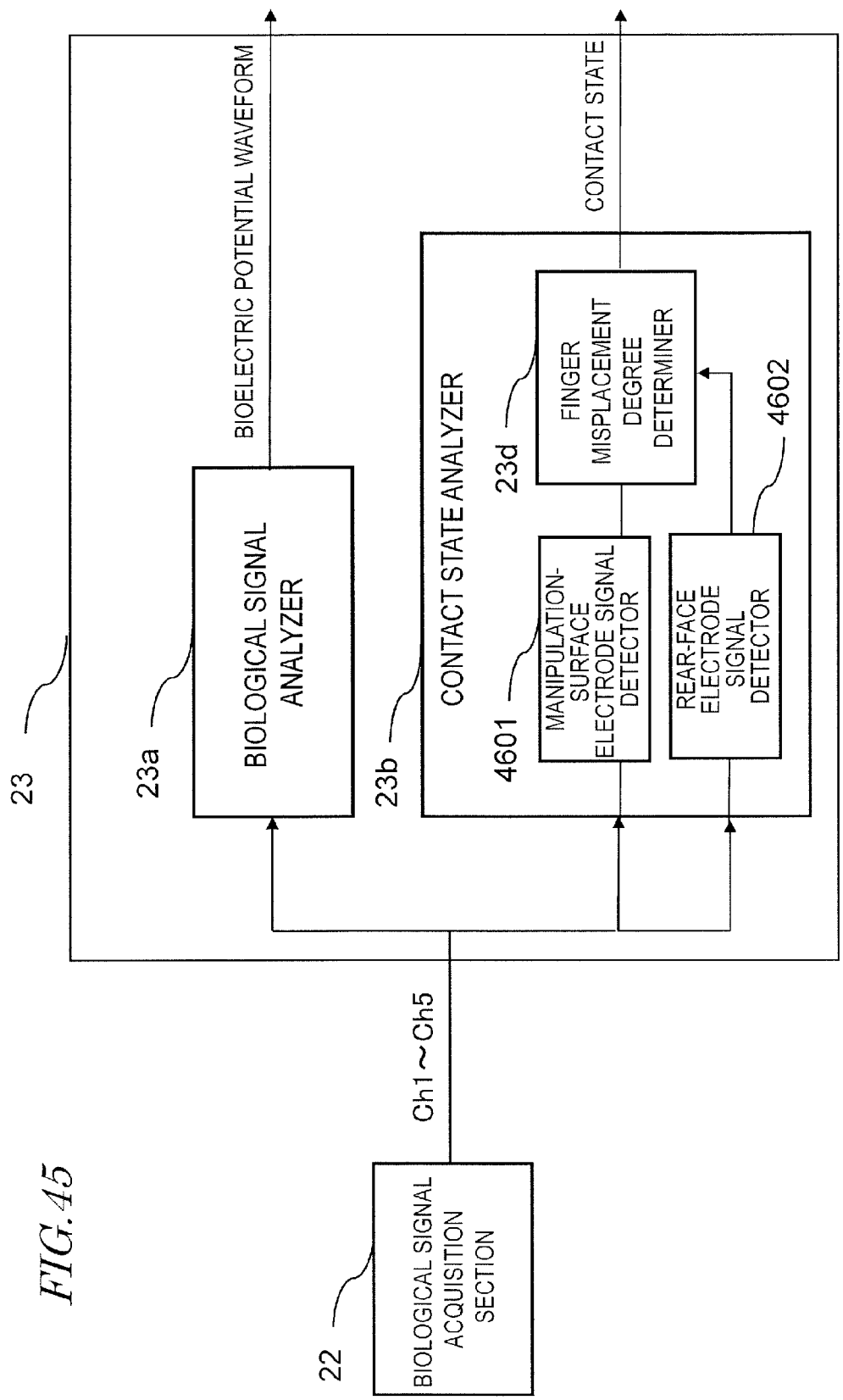

FIG. 45 is a diagram showing the construction of a biological signal processor according to Embodiment 3.

FIG. 46 is a diagram showing electrode positioning according to Embodiment 3.

FIG. 47 is a diagram showing a displayed image according to Embodiment 3.

Figure 48:
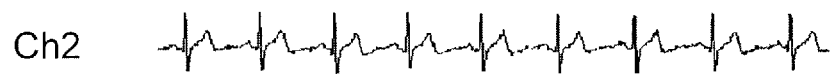

FIG. 48 is a diagram showing exemplary data according to Embodiment 3.

Figure 49:
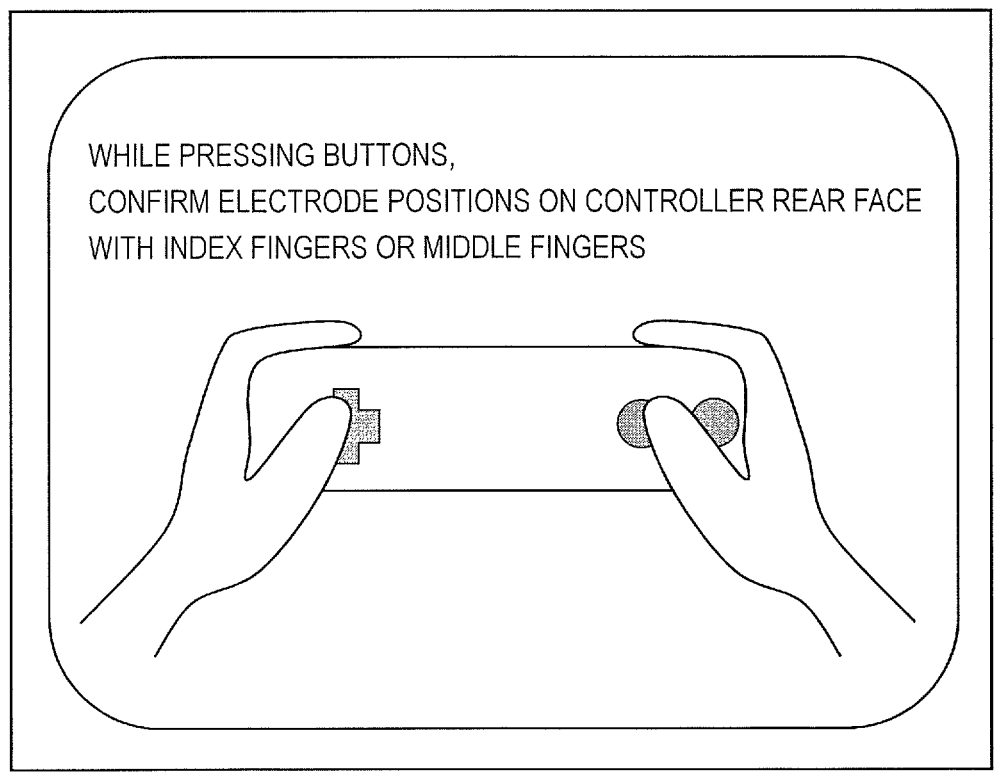

FIG. 49 is a diagram showing a displayed image according to Embodiment 3.

Figure 50A:
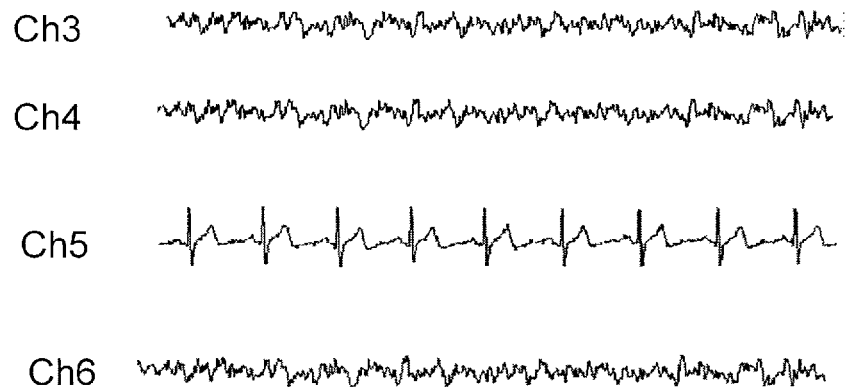
Figure 50B:

FIGS. 50A and 50B are diagrams showing exemplary data according to Embodiment 3.

FIG. 51 is a diagram showing a flow of processing according to Embodiment 3.

Figure 52:
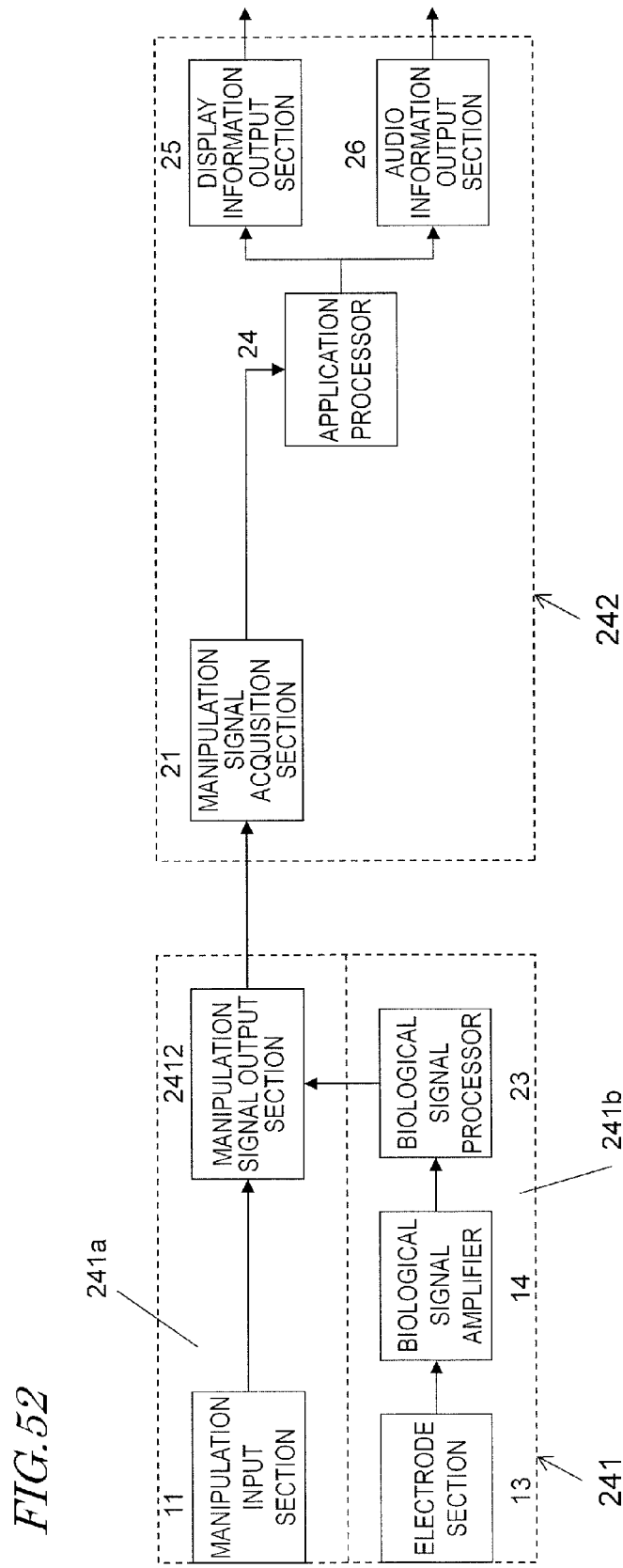

FIG. 52 is a diagram showing a variant of the construction of FIG. 8.

Figure 53:
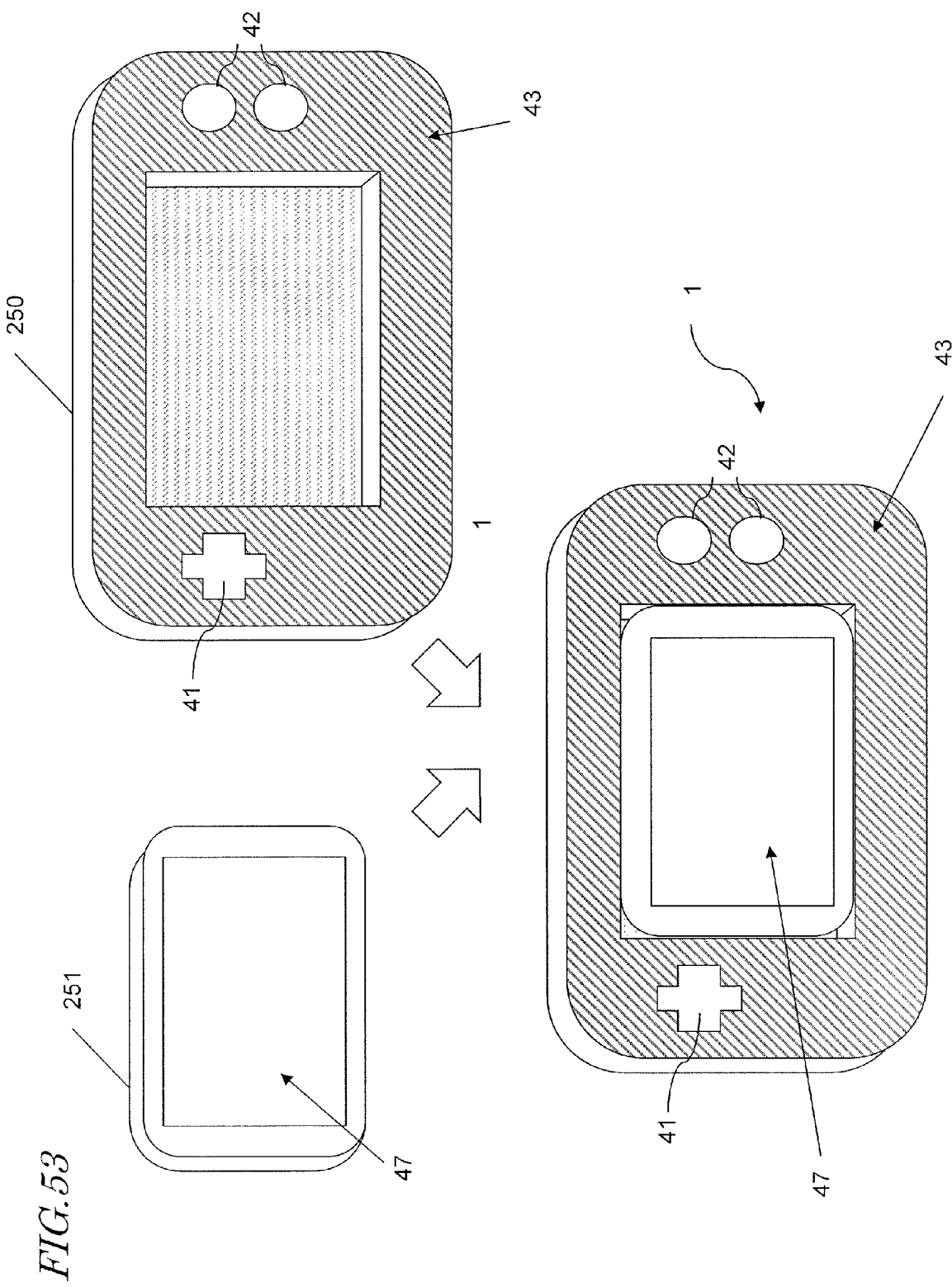

FIG. 53 is a diagram showing an example of a controller 1 which combines an attachment 250 and a smartphone 251.

Figure 54:
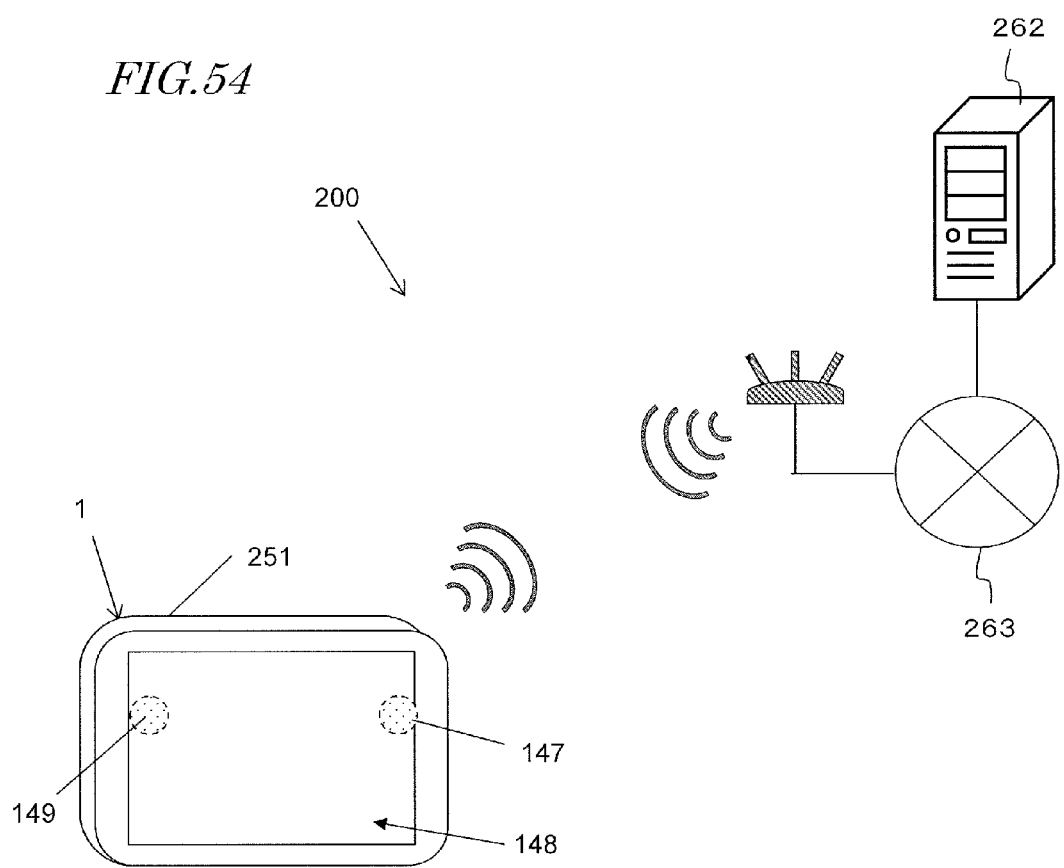

FIG. 54 is a diagram showing a variant of the information processing system according to Embodiment 1 or 2.

DETAILED DESCRIPTION

The findings which provided the basis for the present invention are as follows.

Conventional techniques have not necessarily been easy to handle for users, because the direction(s) of misplacement of a finger(s) to rest on an electrode(s) is/are unclear, thereby hindering stable bioelectric potential measurement.

One implementation of the present invention is as follows, in outline.

An electronic device as one implementation of the present invention is an electronic device in a housing to be gripped by a right hand and a left hand of a user for measuring a potential of a first finger and a potential of a second finger of the user, wherein the first finger is a finger of one of the left or right hand, and the second finger is a finger of the other of the left or right hand, the electronic device comprising: a first electrode group provided in a position to come in contact with the first finger, the first electrode group including a first main electrode and at least one first auxiliary electrode provided at a position away from the first main electrode; a second electrode group provided in a position to come in contact with the second finger, the second electrode group including a second main electrode and at least one second auxiliary electrode provided at a position away from the second main electrode; a biological signal processor for, from a potential value measured at the first electrode group and a potential value measured at the second electrode group, determining respective contact states of the first finger and the second finger; and a transmission circuit for presenting information concerning a finger contact state to the user, based on a result of determination by the biological signal processor.

In one embodiment, the at least one first auxiliary electrode includes a plurality of first auxiliary electrodes; the at least one second auxiliary electrode includes a plurality of second auxiliary electrodes; and the biological signal processor further determines respective degrees of finger misplacement of the first finger and second finger from a potential value measured at the first electrode group including the plurality of first auxiliary electrodes and a potential value measured at the second electrode group including the plurality of second auxiliary electrodes.

In one embodiment, a direction in which misplacement may occur is previously known for each of the first finger and the second finger, and the first electrode group and the second electrode group are disposed along the respective directions in which misplacement may occur; the biological signal processor determines the degree of finger misplacement of each of the first finger and second finger; and when the degree of misplacement exceeds a predetermined value, the transmission circuit further outputs information concerning the degree of finger misplacement.

In one embodiment, the plurality of first auxiliary electrodes are disposed at symmetric positions with respect to the first main electrode; and when the first main electrode and the plurality of first auxiliary electrodes are at a same potential, the biological signal processor determines that the degree of misplacement of the first finger is sufficiently small.

In one embodiment, the plurality of first auxiliary electrodes are disposed consecutively along a predetermined direction from the first main electrode; and when the first main electrode and the plurality of first auxiliary electrodes are at a same potential, the biological signal processor determines that the degree of misplacement of the first finger is relatively large.

In one embodiment, $F \geq X+D+Y$ is satisfied, wherein, the first main electrode is shaped as a first circle with a diameter X; the at least one first auxiliary electrode has a length Y along a normal direction of the first circle; an interspace between the main electrode and the at least one first auxiliary electrode has a minimum value D; and a second circle surrounding a contact range of the first finger has a diameter F.

In one embodiment, $F \leq X+D$ is satisfied, wherein, the first main electrode is shaped as a first circle with a diameter X; an interspace between the first main electrode and the at least one first auxiliary electrode has a minimum value D; and a second circle surrounding a contact range of the first finger has a diameter F.

In one embodiment, according to a change over time in the contact state of the user, the biological signal processor switches between the first main electrode and the at least one first auxiliary electrode as an electrode with which to measure a bioelectric potential.

In one embodiment, the first electrode group and the second electrode group include one reference electrode, such that a potential value measured at the first electrode group and a potential value measured at the second electrode group are potential differences against the reference electrode; and according to a change over time in the contact state of the user, the biological signal processor switches the reference electrode.

In one embodiment, the electrodes included in the first electrode group and the second electrode group are active electrodes.

In one embodiment, the electronic device further comprises: a current source connected to each electrode of the first electrode group and the second electrode group for applying an electric current thereto; and an impedance measurement circuit for, by using the applied electric current, measuring contact impedances between each electrode and the first finger and the second finger, wherein, based on a result of contact impedance measurement, the biological signal processor determines the contact state of each of the first finger and the second finger.

In one embodiment, the at least one first auxiliary electrode includes a plurality of first auxiliary electrodes; the at least one second auxiliary electrode includes a plurality of second auxiliary electrodes; buttons to be manipulated by the user are further provided on the housing; and the plurality of first auxiliary electrodes and the plurality of second auxiliary electrodes are provided on the buttons and on a rear face of the housing opposite from a face on which the buttons are provided.

In one embodiment, the first main electrode and the second main electrode are provided on the rear face, the electronic device further comprising: a manipulation surface electrode signal detector for measuring potentials at the first auxiliary electrode and the second auxiliary electrode provided on the buttons; and a rear face electrode signal detector for measuring potentials at the first main electrode, the second main electrode, the first auxiliary electrode, and the second auxiliary electrode provided on the rear face, wherein, the biological signal processor determines respective contact states of the first finger and the second finger through comparison between each potential measured by the manipulation surface electrode signal detector and each potential measured by the rear face electrode signal detector.

An information processing apparatus as one implementation of the present invention is an information processing apparatus for receiving and processing a manipulation signal and a biological signal from an electronic device having a plurality of manipulable portions, wherein, the biological signal is a potential value measured at a first electrode group provided in a position to come in contact with a first finger of a user gripping a housing of the electronic device and a potential value measured at a second electrode group provided in a position to come in contact with a second finger of the user; the first finger is a finger of one of a left or right hand of the user, and the second finger is a finger of the other of the left or right hand; the first electrode group includes a first main electrode and at least one first auxiliary electrode provided at a position away from the first main electrode; and the second electrode group includes a second main electrode and at least one second auxiliary electrode provided at a position away from the second main electrode, the information processing apparatus comprising: a manipulation signal reception circuit for receiving the manipulation signal transmitted from the electronic device; a biological signal reception circuit for acquiring the biological signal transmitted from the electronic device; a biological signal processor for, from a potential value measured at the first electrode group and a potential value measured at the second electrode group, determining respective contact states of the first finger and the second finger; and a transmission circuit for presenting information concerning a finger contact state to the user, based on a result of determination by the biological signal processor.

An information processing method as one implementation of the present invention is an information processing method to be performed using an electronic device, the electronic device being in a housing to be gripped by a right hand and a left hand of a user and having a first electrode group provided in a position to come in contact with a first finger of the user and a second electrode group provided in a position to come in contact with a second finger of the user, the first electrode group including a first main electrode and at least one first auxiliary electrode provided at a position away from the first main electrode, the second electrode group including a second main electrode and at least one second auxiliary electrode provided at a position away from the second main electrode, the information processing method comprising: measuring a potential of the first finger and a potential of the second finger, the first finger being a finger of one of the left or right hand, and the second finger being a finger of the other of the left or right hand; determining respective contact states of the first finger and the second finger from a potential value measured at the first electrode group and a potential value measured at the second electrode group; and based on a result of the step of determining contact states, presenting information concerning a finger contact state to the user.

A computer program as one implementation of the present invention is a computer program to be executed by a computer provided in an electronic device, the electronic device being in a housing to be gripped by a right hand and a left hand of a user and having a first electrode group provided in a position to come in contact with a first finger of the user and a second electrode group provided in a position to come in contact with a second finger of the user, the first electrode group including a first main electrode and at least one first auxiliary electrode provided at a position away from the first main electrode, the second electrode group including a second main electrode and at least one second auxiliary electrode provided at a position away from the second main electrode, the computer program causing the computer to execute: receiving information of a potential of the first finger and a potential of the second finger measured by the electronic device, the first finger being a finger of one of the left or right hand, and the second finger being a finger of the other of the left or right hand, determining respective contact states of the first finger and the second finger from a potential value measured at the first electrode group and a potential value measured at the second electrode group; and based on a result of the step of determining contact states, presenting information concerning a finger contact state to the user.

Hereinafter, with reference to the attached drawings, embodiments of the "information processing system" according to one implementation of the present disclosure will be described.

(Description of an Information Processing System Including a Controller and an Information Processing Apparatus)

Figure 1:
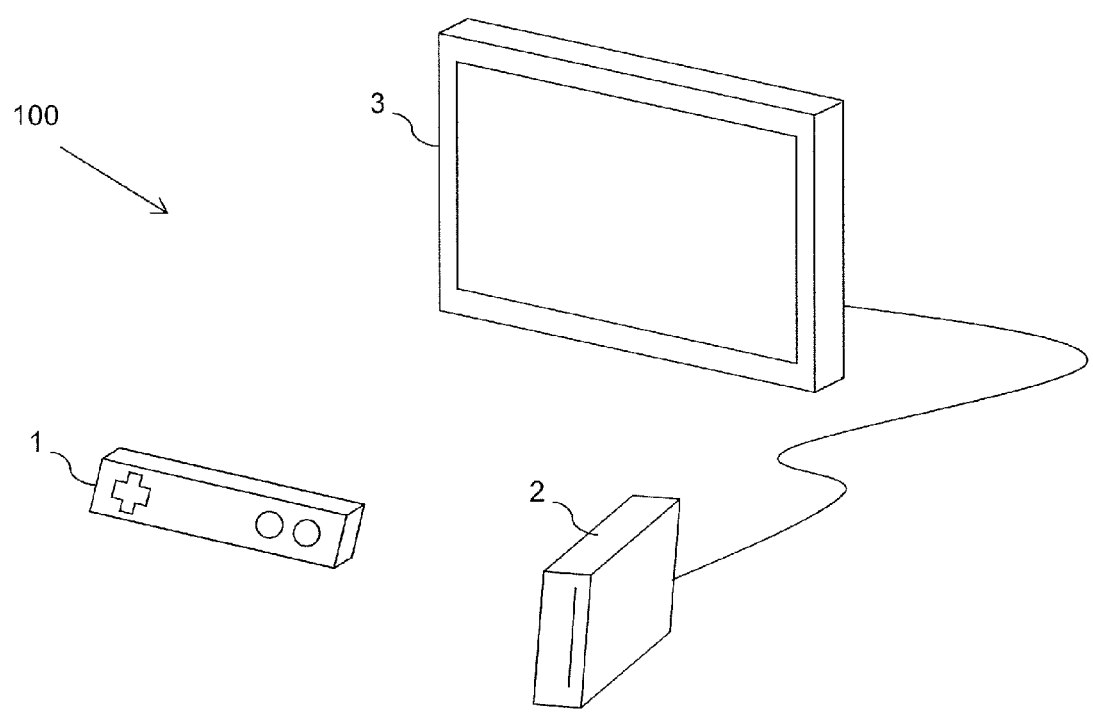
FIG. 1 is a diagram showing a manner in which an information processing system may be used.

FIG. 1 shows a manner in which an information processing system 100 may be used. The information processing system 100 shown in FIG. 1 includes a controller 1, an information processing apparatus 2, and a display device 3. The controller 1, the information processing apparatus 2, and the display device 3 are interconnected in a wired or wireless manner to enable exchange of information.

The controller 1 includes an input device for allowing a user to input manipulation information, with which the user manipulates the information processing system. A manipulation for realizing a desired process may be input to the input device.

The information processing apparatus 2 receives a manipulation input from the controller 1, and performs a predetermined process. In the present specification, the "predetermined process" collectively refers to any application to be executed on a computer for household use, e.g., games, health management, learning, and so on.

The display device 3 displays a processing result by the information processing apparatus 2. The display device displays image information, or presents audio information. As used herein, to "indicate" means outputting a video image on a display, and/or outputting an audio through a loudspeaker. In other words, the display device 3 displays image information, or presents audio information.

(Controller Shape)

Figure 2A:
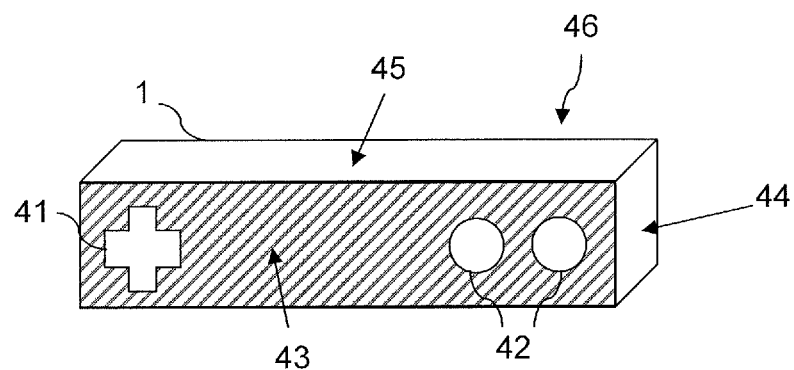
FIGS. 2A and 2B are diagrams showing examples of controller shapes and the names of faces.
Figure 2B:
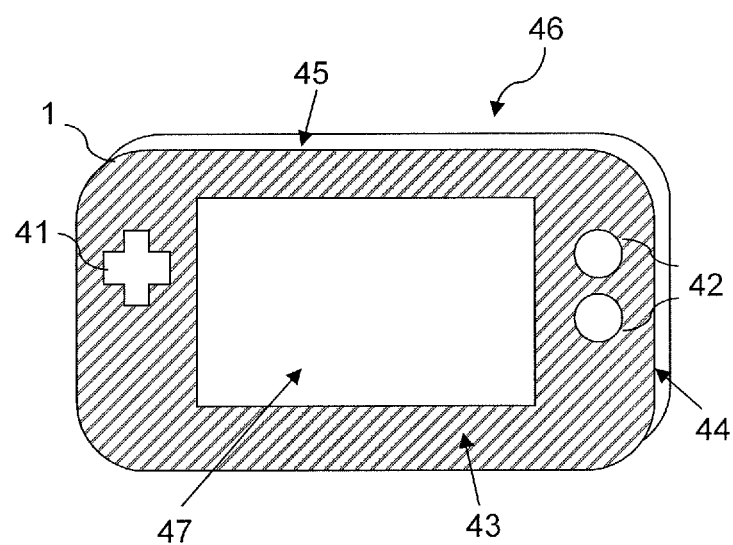

FIGS. 2A and 2B show example shapes of the controller 1. For example, a user may hold the controller 1 in both hands to manipulate it. Examples of the appearance of the controller 1 are the stick type (FIG. 2A) and the pad type (FIG. 2B).

A stick-type controller 1 shown in FIG. 2A has a stick shape of a laterally elongated bar. The user holds it at both ends, so as to manipulate an operation button 41 with the left thumb, and operation buttons 42 with the right thumb. In the illustrated example, the operation button 41 is of a type which enables input in the up/down/right/left directions, and the operation buttons 42 are two buttons for providing twofold control.

The pad-type controller 1 shown in FIG. 2B has a plate-like pad shape. The user holds it at both sides, so as to manipulate an operation button 41 with the left thumb, and operation buttons 42 with the right thumb. A display screen 47 is provided in the central portion of the pad, where the state of manipulation and/or processing results of an application can be displayed.

(Definition of Faces)

With reference to FIGS. 2A and 2B, the names of faces used in the present specification will be defined.

The controller 1 has a manipulation surface 43, a left side face (not shown), a right side face 44, an upper side face 45, a lower side face (not shown), and a rear face 46.

The manipulation surface 43 shown in FIG. 2A and FIG. 2B is a face on which the operation button 41 and the operation buttons 42 are placed.

As one faces the manipulation surface 43 as shown in the figure, the side faces which appear to the right/left/above/below of the manipulation surface 43 are, respectively, the right side face 44, the left side face (not shown), the upper side face 45, and the lower side face (not shown). The opposite face from the manipulation surface 43 is the rear face 46.

The manipulation surface can be similarly defined either for a stick-type controller or a pad-type controller.

In the case where the operation buttons 41 and 42 are those which are displayed on the display screen 47, the face of the controller that contains the display screen 47 defines the manipulation surface 43. Alternatively, only the screen of the display screen 47 on which information is to be displayed may define the manipulation surface 43. In the case where the manipulation surface 43 is composed of a touch panel, the operation buttons 41 and 42 are inclusive of manipulation input indications which are displayed on the manipulation surface 43. A controller whose manipulation surface 43 is composed of a touch panel may typically be a smartphone or a tablet-type computer. By executing application software for manipulating the information processing apparatus 2, such a smartphone or tablet-type computer acquires functions similar to those of the controller 1 having hardware operation buttons 41 and 42. A controller having hardware operation buttons 41 and 42 and a controller having software operation buttons 41 and 42 (manipulation input indications) will collectively be referred to as an "electronic device" in the present specification.

In the case where the manipulation surface 43, the left side face (not shown), the right side face 44, the upper side face 45, the lower side face (not shown), and the rear face 46 are composed of a single surface, it is meant that the left side face (not shown), the right side face 44, the upper side face 45, the lower side face (not shown), and the rear face 46 merely define portions that are based on relative positioning from the manipulation surface 43.

(Electrode Positions)

Figure 3A:
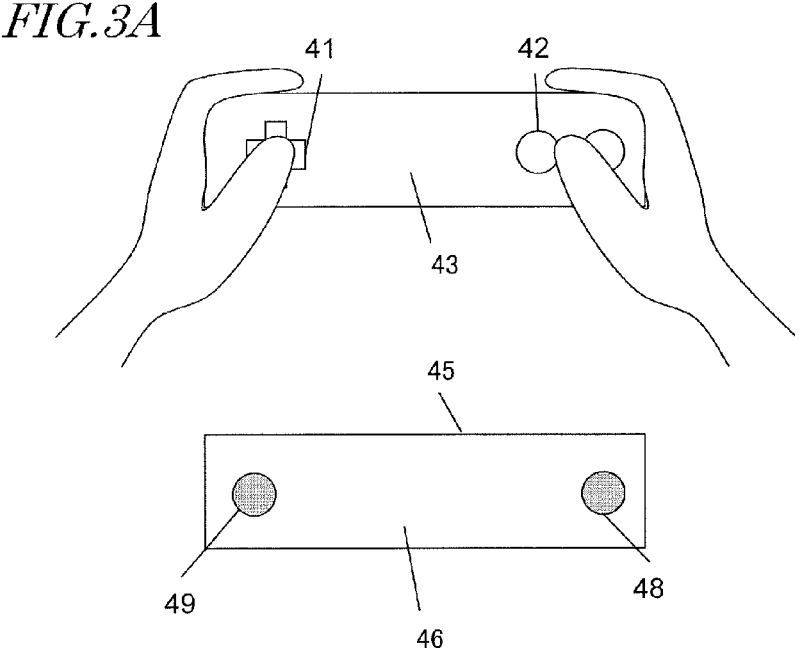
FIGS. 3A and 3B are diagrams showing examples of electrode positions in the case where electrodes are disposed on the rear face.
Figure 3B:
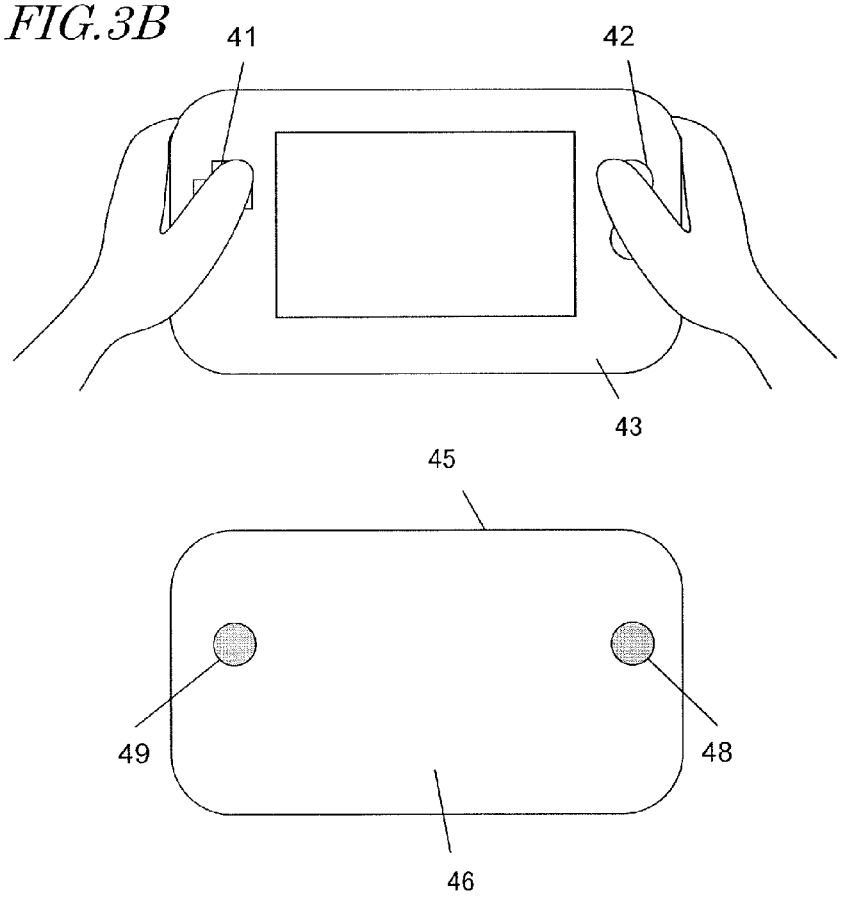

Next, the positions of electrodes for biological signal measurement which are placed on the controller 1 will be described. FIGS. 3A and 3B show examples where electrodes for biological signal measurement are placed on the rear face 46 of the controller 1.

In order to measure a biological signal, at least a plurality of electrodes are placed on the controller 1. A biological signal means a potential difference between a plurality of positions at which a user is in contact with the controller. An example of a biological signal may be a potential difference between a finger of the right hand and a finger of the left hand, and may include a biological signal derived from an electrocardiogram, etc.

The user holds the stick-type controller 1A in both hands to manipulate the operation button(s) 41, 42 with a thumb. In doing so, in order to counteract the force with which the thumb presses the operation button(s) 41, 42, it is necessary to support the rear face 46 with an index finger or a middle finger. In order to support the rear face 46, the index finger or middle finger of the user stays in contact with the rear face 46.

The controller has electrodes at positions where the user's fingers will come in contact the controller when the user grips the controller.

For example, the rear face 46 has a plurality of electrodes each in a predetermined range which contains a position that is opposite from the position of the operation button(s) 41 or 42 on the manipulation surface 43. An example of a predetermined range is a range around the position opposite from the position of the operation button(s) 41 or 42, with a radius which is defined by the movable range of the user's finger.

The controller 1 shown in FIG. 3A includes an electrode 48 for the left hand at a portion where a finger of the left hand is in contact, and an electrode 49 for the right hand at a portion where a finger of the right hand is in contact.

Similarly with the pad-type controller 1B shown in FIG. 3B, the user supports the rear face 46 with fingers in order to counteract the force with which the operation buttons 41 and 42 on the manipulation surface 43 are pressed. The electrode 48 for the left hand and the electrode 49 for the right hand are placed at positions where the user comes in contact with the rear face 46 in order to support the rear face 46. By placing electrodes at these positions, biological signal measurement can be continued even during manipulation.

Figure 4A:
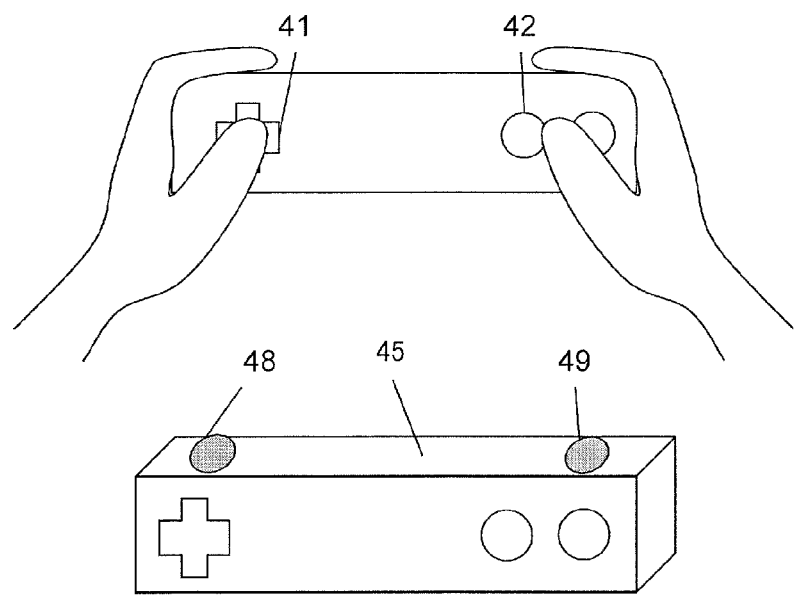
FIGS. 4A and 48 are diagrams showing examples of electrode positions in the case where electrodes are disposed on the upper side face.
Figure 4B:
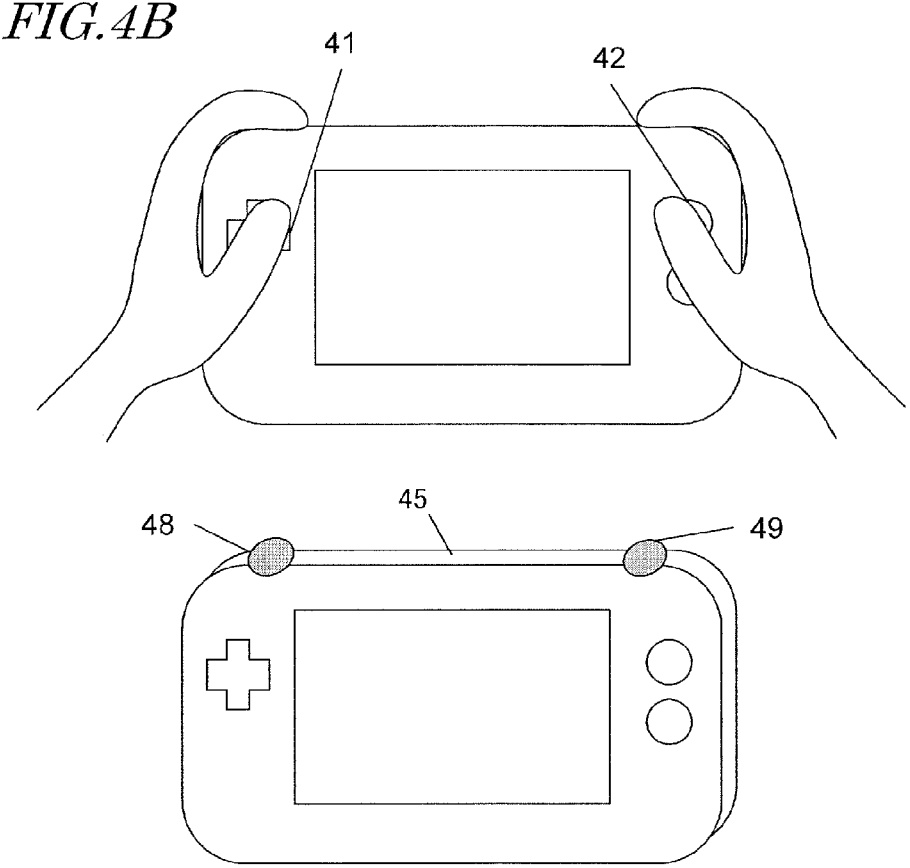

FIGS. 4A and 4B show an example where electrodes for biological signal measurement are placed on the upper side face 45 of the controller 1A. One possible manner in which the user may hold the stick-type controller 1 in both hands is where the index fingers are placed on the upper side face 45, with the middle fingers, ring fingers, and little fingers being placed on the rear face 46.

In this case, the user's index fingers will stay on the upper side face 45 all the time, not just by way of supporting the rear face 46 to counteract the force with which the operation buttons 41 and 42 are pressed. Thus, the controller 1 may have the electrode 48 for the left hand and the electrode 49 for the right hand on the upper side face 45, where the index fingers are rested. Similarly a manner of holding in which the index fingers are rested on the upper side face 45 is also possible with a pad-type controller 1B; therefore, the controller 1B may have the electrode 48 for the left hand and the electrode 49 for the right hand on the upper side face.

(Shapes and Number of Electrodes)

Portions (a) to (d) of FIG. 5 show examples of electrode shapes. The electrode material is composed of an electrically conductive substance. An example of an electrode material is gold or silver. A desirable electrode material is a silver-silver chloride material because a silver-silver chloride material is not very susceptible to polarization when in contact with a living organism.

Other than the round-shaped electrode 51 of FIG. 5(a), which is similar to electrodes that are used for medical purposes, various shapes and numbers of electrodes may be employed depending on the application. For example, the number of electrodes that comes in contact with one hand does not need to be one; it may be two semicircular-shaped electrodes 52a and 52b as shown in FIG. 5(b), two electrodes 53a and 53b in the form of concentric circles as shown in FIG. 5(c), or three electrodes 54a, 54b, and 54c as shown in FIG. 5(d). Allocating two or more electrodes for each hand makes it possible to estimate the state of contact of each finger and the position of the finger, from how a signal is being acquired from each electrode. In particular, allocating a large number of electrodes for each hand makes it possible to estimate the state of contact of each finger and the position of the finger, from how a signal is being acquired from each electrode.

Moreover, the electrode shape is not limited to a round shape, as shown in FIGS. 6A to 6C. For example, as shown in FIG. 6A, electrodes may be placed in broad ranges around portions at which hands may come in contact, in order to ensure that contact will always be maintained. A band-shaped electrode (FIG. 6B) or multiple band-shaped electrodes (FIG. 6C) that expand not only on the rear face 46, but also to the upper side face 45 and the lower side face may be used to enable biological signal measurement against various manners of holding being envisaged.

(System Construction Diagram)

FIG. 7 shows a system construction for the information processing system 100. The controller 1 includes a manipulation input device 1a and a biological signal measurement device 1b.

The controller 1 receives a manipulation input made by the user, and also measures a biological signal of the user during the manipulation. Information including the measured biological signal is sent to the information processing apparatus 2.

Upon receiving inputs from the manipulation input device 1a or the biological signal measurement device 1b, the information processing apparatus 2 performs a predetermined process and outputs a result of the processing to the display screen equipment 3. The controller 1 and the information processing apparatus 2 are interconnected in a wireless or wired manner.

FIG. 8 shows the construction of the controller 1 and the information processing apparatus 2. A case where the controller 1 and the information processing apparatus 2 are wirelessly interconnected will be described.

The manipulation input device 1a in the controller 1 includes a manipulation input section 11 and a manipulation signal output section 12. The manipulation input section 11 is a section which acquires or determines a manipulation signal which has been input from the operation button(s) 41 or 42. The manipulation information having been acquired is sent from the manipulation signal output section 12 to the information processing apparatus 2.

The biological signal measurement device 1b in the controller 1 includes an electrode section 13, a biological signal amplifier 14, and a biological signal output section 15.

The electrode section 13 is composed of a plurality of electrodes. The plurality of electrodes are placed at a position where the user's right hand comes in contact with the controller 1 and a position where the user's left hand comes in contact with the controller 1, for example.

The biological signal amplifier 14 amplifies a biological signal which corresponds to the potential difference between a plurality of electrodes. For example, a potential difference between the right hand and the left hand is amplified by the biological signal amplifier 14. The amplified signal is converted by an A/D converter into a digital signal, and this biological signal information is sent from the biological signal output section 15 to the information processing apparatus 2. Note that, when a biological signal can be measured to a certain potential or greater, the biological signal amplifier 14 does not need to amplify the biological signal, but may only measure the potentials at the plurality of electrodes. For this reason, the biological signal amplifier 14 may also be denoted as a biological signal measurement section in the following description.

In the information processing apparatus 2, the manipulation input information is received at a manipulation signal acquisition section 21, and the biological signal is received at a biological signal acquisition section 22, thus receiving the information from the controller 1.

While as a barely-recorded source signal, the biological signal is often not usable information. Therefore, the biological signal processor 23 performs a process of extracting meaningful information from the source signal. This corresponds to, for example, applying peak detection to chronological changes in a signal representing potential changes between both hands to thereby acquire heart rate information, for example.

The application processor 24 performs central processes of the information processing apparatus 2. Examples of application processing include: game progression in a game application; recording/data management/displaying in a health management application; question-giving/marking/result-displaying in a learning application, and so on. The application processing is realized by performing predetermined processes upon receiving an input from the controller 1.

In order to feed the user back on the result of processing by the application processor 24, the display information output section 25 and the audio information output section 26 output a visual signal and an auditory signal. These output signals are sent to the display screen equipment 3.

The display screen equipment 3 reproduces the signals which have been output from the display information output section 25 and the audio information output section 26. As a result, the signals are presented to the user. Examples of the display screen equipment 3 include television sets, displays, and loudspeakers.

(Hardware Construction)

FIG. 9 shows the hardware construction of the controller 1. The controller 1 includes operation buttons 61, a control signal conversion circuit 62, a measurement electrode 63a, a reference electrode 63b, ground 63c, a biological amplifier 64, an AD conversion circuit 65, a transmission circuit 67, a signal processing unit 66, an antenna 68, and a battery 69.

Among these, the operation buttons 61 and the control signal conversion circuit 62 correspond to the manipulation input section 11 shown in FIG. 8. The measurement electrode 63a, the reference electrode 63b, and the ground 63c correspond to the electrode section 13 shown in FIG. 8, whereas the biological amplifier 64 corresponds to the biological signal amplifier 14 shown in FIG. 8. Note that the AD conversion circuit 65 may be included in the biological signal amplifier 14. The signal processing unit 66 includes a CPU 101, a RAM 102, a program 103, and a ROM 104. The transmission circuit 67 and the antenna 68 function as the biological signal output section 15 and/or the manipulation signal output section 12 show in FIG. 8; these may be referred to as the "output section" or "transmission section". These component elements are interconnected via a bus 105, so that mutual data exchange is possible. Power is supplied from the battery 69 to each circuit.

The press-down information of each of the operation buttons 61 is converted by the control signal conversion circuit 62, and sent to the CPU 101 via the bus.

The measurement electrode 63a, the reference electrode 63b, and the ground 63c are connected to the biological amplifier 64, these electrodes being mounted at predetermined places on the controller 1. The potential difference between the measurement electrode 63a and the reference electrode 63b is amplified by the biological amplifier 64, converted by the AD conversion circuit 65 from an analog biological signal to a digital signal, and, now as a biological signal that is capable of processing and transmission, sent to the CPU 101 via the bus.

The CPU 101 executes the program 103 which is stored in the memory 102. The program 103 describes a processing procedure as indicated by flowcharts which will be described later. In accordance with the program 103, the controller converts the manipulation signal and the biological signal which are sent from the antenna 68 via the transmission circuit 67. In certain cases, the program 103 may be stored in the ROM 104.

Note that the signal processing unit 66, the control signal conversion circuit 62, the transmission circuit 67, the biological amplifier 64, and the AD conversion circuit 65 may be implemented as a piece of hardware (e.g., a DSP) consisting of a semiconductor circuit having a program incorporated therein. Combining these into one semiconductor circuit will also provide the effect of reducing power consumption.

FIG. 10 shows the hardware construction of the information processing apparatus 2. The information processing apparatus 2 includes an antenna 71, a receiver circuit 72, a signal processing unit 73, an image control circuit 74, a display information output circuit 75, an audio control circuit 76, an audio information output circuit 77, and a power supply 78.

Among these, the antenna 71 and the receiver circuit 72 function as the biological signal acquisition section 22 and/or the manipulation signal acquisition section shown in FIG. 8. These may be referred to as the "reception section".

The signal processing unit 73 includes a CPU 111, a RAM 112, a program 113, and a ROM 114. The signal processing unit 73 functions as the biological signal processor 23 and/or the application processor 24 in FIG. 8. The image control circuit 74 and the display information output circuit 75 function as the display information output section 25 in FIG. 8. The audio control circuit 76 and the audio information output circuit 77 function as the audio information output section 26 in FIG. 8. These are interconnected via a bus 115 so that mutual data exchange is possible. Power is supplied from the power supply 78 to each circuit.

The manipulation information and biological information from the controller 1 are received by the receiver circuit 72 via the antenna 71, and sent to the CPU 111 via the bus 115.

The CPU 111 executes a program 113 which is stored in the memory 112. The program 113 describes a processing procedure as indicated by flowcharts which will be described later. In accordance with the program 113, the information processing apparatus converts the manipulation signal and the biological signal, performs a process for executing a predetermined application, and generates signals for providing image/audio feedback to the user. In certain cases, the program 113 may be stored in the ROM 114.

The image feedback signal which has been generated by the signal processing unit 73 is output from the display information output circuit 75 via the image control circuit 74, and the audio feedback signal is output from the audio information output circuit 77 via the audio control circuit 76.

Note that the signal processing unit 73, the receiver circuit 72, the image control circuit 74, and the audio control circuit 76 may be implemented as a piece of hardware (e.g., a DSP) consisting of a semiconductor circuit having a program incorporated therein. Combining these into one semiconductor circuit will also provide the effect of reducing power consumption.

(General Flow of Processes)

FIG. 11 shows a flow of processing by the controller 1 and the information processing apparatus 2. Steps S11 to S14 illustrate internal processing by the controller 1, and steps S21 to S25 illustrate processing by the information processing apparatus 2.

<Step S11>

The manipulation input section 11 accepts a manipulation input. Specifically, at the timing of accepting a manipulation input, the manipulation input section 11 detects whether or not any operation button is being pressed. The timing of acceptance may be when an operation button is pressed down, for example.

<Step S12>

The manipulation signal output section 12 outputs a manipulation signal corresponding to the manipulation input accepted by the manipulation input section 11.

<Step S13>

The biological signal amplifier 14 measures a biological signal which corresponds to the potential difference between a plurality of electrodes 13. For example, a potential difference between the right hand and the left hand being in contact with the controller is measured. Moreover, the biological signal amplifier 14 may amplify the measured biological signal.

<Step S14>

The biological signal output section 15 outputs the biological signal.

Note that steps S11 and S12, and steps S13 and S14, may be conducted as a parallel process each. It is not necessary that the processes of steps S11 to S14 be executed all in this order.

<Step S21>

The manipulation signal acquisition section 21 receives the manipulation signal from the manipulation signal output section 12.

<Step S22>

The biological signal acquisition section 22 receives the biological signal from the biological signal output section 15.

<Step S23>

The biological signal processor 23 extracts biological information from the biological signal received at the biological signal acquisition section 22.

<Step S24>

Upon receiving the manipulation information from the manipulation signal acquisition section 21 and the biological information from the biological signal processor 23, the application processor 24 performs predetermined processes for executing the current application.

<Step S25>

In order to feed the user back on the result of processing by the application processor 24, the display information output section 25 outputs video information, and the audio information output section 26 outputs audio information.

Although not described in the flow of processes shown in FIG. 11, the display screen equipment 3 displays the information which is output from the information processing apparatus 2.

Note that the application processor 24 does not need to process both of the manipulation information from the manipulation signal acquisition section 21 and the biological information from the biological signal processor 23, and may process only the biological signal. In that case, step S21 of receiving the manipulation signal may be omitted.

Embodiment 1

FIG. 8 shows an overall construction of the information processing system 100 according to Embodiment 1. The information processing system of Embodiment 1 at least includes the electrode section 13, the biological signal amplifier 14, and the biological signal processor 23.

The electrode section 13, the biological signal amplifier 14, and the biological signal output section 15 are included in a housing composing the controller 1. In a different example from that shown in FIG. 8, the controller 1 may include the biological signal processor 23, in which case the information processing apparatus 2 lacks the biological signal processor 23 but sends a biological signal which is acquired by the biological signal acquisition section 22 to the application processor 24.

Hereinafter, the construction of the electrode section 13, the biological signal processor 23, and the application processor 24, which are some of the characteristic features of the present embodiment, will be described.

(Electrode Section)

The electrode section 13, which is provided on the housing of the controller 1, includes a main electrode and a plurality of auxiliary electrodes at least partially surrounding the periphery of the main electrode. The plurality of auxiliary electrodes are disposed in a plurality of different directions around the main electrode.

FIG. 12A shows an example deployment of the electrode section 13. A circular main electrode 54a is provided in the center. Auxiliary electrodes 54b and 54c are disposed around the main electrode 54a, which are shapes that are obtained by dividing a concentric circle around the main electrode 54a into right and left. The auxiliary electrodes 54b and 54c are disposed in different directions from the center of the main electrode 54a.

In the case where an adult male allows only the tip of a middle finger to be in contact with the rear face 46, the range in which the user touches the controller 1 spans a diameter of approximately 14 mm. An index finger or a ring finger of an adult male would touch the controller 1 in a generally similar range to that of a middle finger. Adult females or children would require somewhat smaller electrodes than the electrodes for adult males.

The deployment of the auxiliary electrodes 54b and 54c shown in FIG. 12B illustrates an example where finger misplacements are supposed to occur only along the right-left direction. The expected size for the electrode section 13 is indicated by dimensions shown in FIG. 12A, which are determined from the fact that the contact range of the index finger, the middle finger, or the ring finger has a circle shape with a diameter of F=14 mm. The circular main electrode 54a has a diameter X of 10 mm, and the auxiliary electrode 54b has a width (i.e., length along the normal direction of the main electrode 54a) Y of 1 mm. As used herein, the normal is a line extending in a direction which is perpendicular to a tangent on the circular main electrode 54a. Therefore, the normal direction coincides with a direction in which a line passing through the center of the circular main electrode 54a extends.

This relative positioning is such that, when the pad of a finger is placed on the center of the main electrode 54a, the two auxiliary electrodes 54b and 54c will both abut with the finger. In other words, the main electrode 54a and the two auxiliary electrodes 54b and 54c are located within a predetermined range which corresponds to e.g., the contact range of the user's finger. At least the main electrode 54a and each of the auxiliary electrodes 54b and 54c are partly located within the aforementioned predetermined range. The predetermined distance between the main electrode 54a and the auxiliary electrodes 54b and 54c is subject to the size of the main electrode 54a.

Assuming a diameter X of the main electrode 54a, a width Y of the auxiliary electrode 54b, and an interspace D between the main electrode 54a and the auxiliary electrode 54b or 54c, it is desirable that the relationship of eq. 1 below is satisfied.

$$X+2D+2Y \leq F \qquad (\text{eq. 1})$$

It is desirable that the electrodes are sized so as to result in a similar figure to what is defined by the dimensions shown in FIG. 12A, based on the actual contact range of a finger.

As an example, the electrode section 13 may be deployed on the left side face (not shown), the right side face 44, the upper side face 45, the lower side face (not shown), and the rear face 46 of the controller 1.

FIG. 12B shows an example where the electrodes are placed on the rear face 46 of the controller 1. In FIG. 12B, electrodes 48a to 48c which are placed at the right side in the figure are in contact with a finger of the left hand of the user, and electrodes 49a to 49c which are placed at the left side in the figure are in contact with a finger of the right hand of the user. In the present specification and the figures, in order to avoid confusion, the right direction in the figure may be referred to as the +P direction and the left direction in the figure as the −P direction, as indicated in FIG. 12B.

In a state where the controller is gripped by both hands, the electrode section 13 is composed of the main electrode 48a and two auxiliary electrodes 48b and 48c placed at the right side as well as the main electrode 49a and two auxiliary electrodes 49b and 49c placed at the left side. The main electrodes 48a and 49a will be referred to as the main electrode section 13a, whereas the auxiliary electrodes 48b, 48c, 49b, and 49c will be referred to as the auxiliary electrode section 13b. In the example shown in FIG. 12B, where the pads of the middle finger of the user's right hand and the middle finger of the user's left hand rest on the main electrodes 49a and 48a, respectively, there are fingers resting on the electrodes of all main electrode section and auxiliary electrode section. In FIG. 12B, the right main electrode 48a will be referred to as a measurement electrode (Ch1) and the left main electrode 48b as a reference electrode (Ref) in the following description. Furthermore, as shown in FIG. 12B, the auxiliary electrodes 48b, 48c, 49b, and 49c are designated Ch2, Ch3, Ch4, and Ch5, respectively.

FIG. 13 shows connection from the electrode section 13 to the biological signal amplifier 14 in the controller 1. As for the main electrode section, the main electrodes 48a and 49a are connected to Ch1 and Ref of the biological signal amplifier 14, respectively. As for the auxiliary electrode section, the auxiliary electrodes 48b, 48c, 49b, and 49c are connected to Ch2, Ch3, Ch4, and Ch5 of the biological signal amplifier 14, respectively. In the biological signal amplifier 14, signals on Ch1 to Ch5 are each amplified (differential amplification) after a difference thereof from the signal on Ref; the amplified signals are filtered through a low-pass filter, and converted by an A/D converter into digital signals; and the digital data on Ch1 to Ch5 are output to the biological signal output section 15.

(Biological Signal Processor)

FIG. 14 shows the construction of the biological signal processor 23. The biological signal processor 23 shown in FIG. 14 includes a biological signal analyzer 23a and a contact state analyzer 23b. As an example, the controller 1 at least includes the biological signal acquisition section 22 and the contact state analyzer 23b.

The biological signal acquisition section 22 acquires information of biological signals between the main electrode 48a (49a) and the plurality of auxiliary electrodes 48b, 48c, 49b, and 49c. From a biological signal acquired from the biological signal acquisition section 22, the contact state analyzer 23b determines a contact state of the electrode section 23. By referring to prestored information concerning the relationship between contact states and directions of contact misplacement, the contact state analyzer 23b determines a direction of contact misplacement (i.e., the +P direction or the −P direction) between the electrode section 23 and the user. This will be specifically described below.

The data on Ch1 to Ch5 acquired by the biological signal acquisition section 22 is sent to the biological signal analyzer 23a and the contact state analyzer 23b. The biological signal analyzer 23a includes a high-pass filter with a selectable cutoff frequency, a low-pass filter, and the like. By using these filters and the like, the biological signal analyzer 23a performs signal processing, and generates a bioelectric potential waveform to be displayed on the display screen equipment 3, via the display information output section 25. The contact state analyzer 23b includes a signal detector 23c and a finger misplacement degree determiner 23d. Based on the potential waveforms on Ch1 to Ch5, the signal detector 23c determines whether a biological signal is present or not on each Ch. Based on the information concerning the presence or absence of a signal on each Ch as determined by the signal detector 23c, the finger misplacement degree determiner 23d determines whether the position of a finger that is resting on the electrode section is misplaced or not. The specific operations of the signal detector 23c and the finger misplacement degree determiner 23d of the contact state analyzer 23b will be described later.

FIG. 15 shows an example flow of the contact state analysis process by the contact state analyzer 23b. Step S111 is processed by the signal detector 23c. Steps S112 and S113 are processed by the finger misplacement degree determiner 23d.

<Step S111>

The signal detector 23c detects signals on Ch1 to Ch5. For example, an image for asking the user to make preparations before beginning measurement may be displayed on the display device 3, or an audio to the same effect may be output.

<Step S112>

The finger misplacement degree determiner 23d detects the position of contact of an electrode corresponding to each signal from Ch1 to Ch5.

<Step S113>

The finger misplacement degree determiner 23d stores therein a relationship between the electrode positions and electrode contact information of the user and the directions of misplacement of the user. The details thereof will be described later with reference to FIG. 18.

Based on the relationship between the electrode positions and electrode contact information of the user and the directions of misplacement of the user, and on the detected information of electrode positions of contact, the finger misplacement degree determiner 23d determines a direction of finger misplacement. Note that the finger misplacement degree determiner 23d may also be referred to as a finger misplacement direction determination section.

(Example States of Finger Misplacement)

Figure 16A:
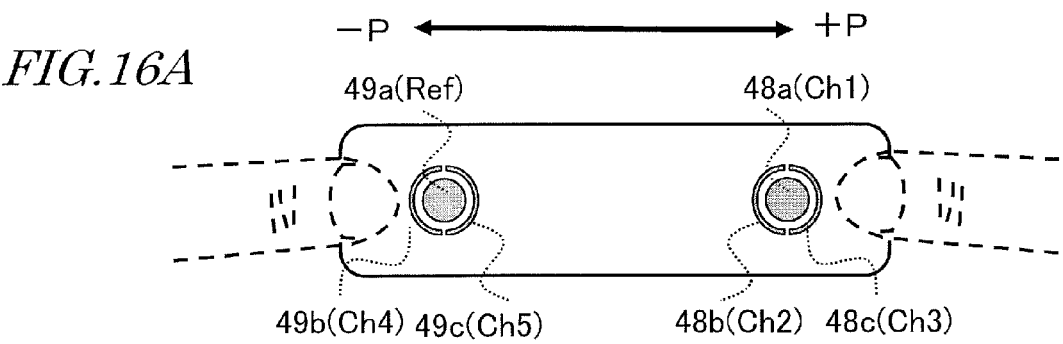
Figure 16B:
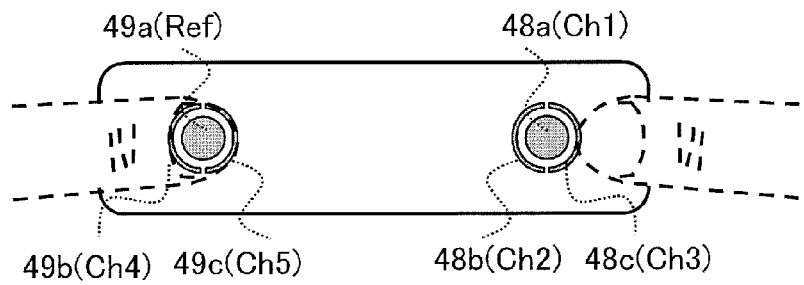
Figure 16C:
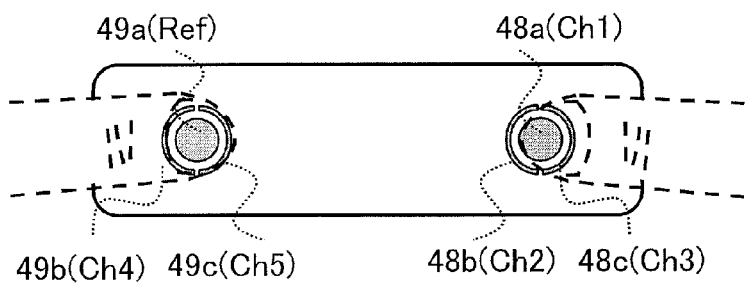
Figure 16D:
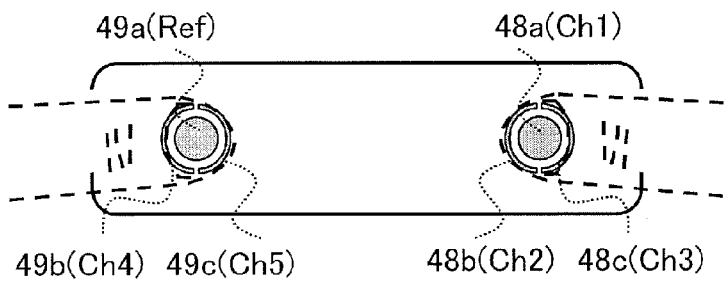

FIGS. 16A to 16D show various states of finger misplacement which may occur when the controller 1 is gripped by both hands, according to the present embodiment. The first state shown in FIG. 16A is a case where the fingers are not rested on either the right or left electrodes. Directions "+P" and "−P" shown in FIG. 16A are referred to with respect to the following FIGS. 16B to 16D. The second state shown in FIG. 16B is a case where a finger of the right hand is rested on all of the main electrode 49b and the auxiliary electrodes 49b and 49c, while a finger of the left hand is misplaced in the +P direction so as to be rested only on the auxiliary electrode 48c. The third state shown in FIG. 16C is a case where a finger of the right hand is rested on all of the main electrode 49b and the auxiliary electrodes 49b and 49c, while a finger of the left hand is somewhat misplaced in the +P direction so as to be rested only on the main electrode 48a and the auxiliary electrode 48c. The fourth state shown in FIG. 16D is a case where fingers are rested on all of the right and left electrodes. The four states can each be distinguished by using the signal detector 23c and the finger misplacement degree determiner 23d in the contact state analyzer 23b of FIG. 14. Note that FIGS. 16B and 16C above illustrate examples where a finger of the left hand of the user is misplaced in the +P direction. It is naturally expectable that a finger of the left hand of the user may be misplaced in the −P direction, or a finger of the right hand of the user may be misplaced in the +P direction or the −P direction.

(Signal Detector)

FIG. 17 shows an example flow of the signal detection process by the signal detector 23c. There are processes from steps S131 to S134.

<Step S131>

The signal detector 23c performs a fast Fourier transform (FFT) for the signal waveform, and determines the frequency characteristics of the signal.

<Step S132>

It is determined whether any component of 10 Hz or less is contained in the signal frequency characteristics. If any frequency component of 10 Hz or less is contained, it is determined that a biological signal is contained.

<Step S133>

Since a component of 10 Hz or less is contained in the signal frequency characteristics, it is determined that there is a signal.

<Step S134>

Since no component of 10 Hz or less is contained in the signal frequency characteristics, it is determined that there is no signal.

In the process of step S132 in FIG. 17 where a determination is made based on whether there exists any component of a predetermined frequency or less, the predetermined frequency is not limited to 10 Hz. Note that the process of step S31 is not limited to FFT calculations. A low-pass filter with a cutoff frequency of 10 Hz may be used.

FIG. 18 shows a relationship of signal detection between Ch1 to Ch5, as determined by the signal detector 23c with respect to example states of finger misplacement given in FIGS. 16A to 16D.

The relationship shown in FIG. 18 is information by which the contact information on the respective electrode positions of Ch1 to Ch5 and the directions of finger misplacement of the user are associated.

In the first to fourth states, for each Ch, "YES" is indicated where a biological signal is found to exist, and "NO" is indicated where no biological signal is found to exist. When a biological signal exists, the following finger misplacement degree determiner 23d determines that the electrode "has contact"; when no biological signal exists, the finger misplacement degree determiner 23d determines that the electrode "has no contact". In the present specification, it is considered that the presence or absence of a biological signal corresponds to information as to whether the user is in contact with an electrode or not.

Based on the presence or absence of a biological signal, the user's direction of finger misplacement is predefined. For example, as shown in FIG. 12A and FIG. 12B, if a main electrode and a plurality of auxiliary electrodes are located in a range which is smaller than the contact range of the user's finger, it is determined that a finger misplacement has occurred in the opposite direction of (i.e. away from) the direction of the electrode which is found to have no biological signal occurring thereon.

The relationship between the finger contact states from the first to fourth states and the directions of finger misplacement of the user will be described by referring to a flow of processes of the contact state analyzer below.

(General Flow of Processing by Contact State Analyzer)

FIG. 19 shows a flow of processing by the contact state analyzer 23b. There are processes from step S141 to step S153.

<Step S141>

Based on the presence or absence of a signal on Ch2, the finger misplacement degree determiner 23d determines whether a finger of the right hand is rested on Ch2, i.e., the auxiliary electrode 48b.

<Step S142>

The finger misplacement degree determiner 23d outputs that "Ch2 has no contact" with a finger.

<Step S143>

Based on the presence or absence of a signal on Ch3, the finger misplacement degree determiner 23d determines whether a finger of the right hand is rested on Ch3, i.e., the auxiliary electrode 48c.

<Step S144>

The finger misplacement degree determiner 23d outputs that "Ch3 has no contact" with a finger.

<Step S145>

Based on the presence or absence of a signal on Ch1, the finger misplacement degree determiner 23d determines whether a finger of the right hand is rested on Ch1, i.e., the main electrode 48a.

<Step S146>

The finger misplacement degree determiner 23d outputs that the finger is "misplaced in the right (+P) direction".

<Step S147>

The finger misplacement degree determiner 23d outputs that "Ch1 has no contact" with a finger.

<Step S148>

Based on the presence or absence of a signal on Ch1, the finger misplacement degree determiner 23d determines whether a finger of the right hand is rested on Ch1, i.e., the main electrode 48a.

<Step S149>

The finger misplacement degree determiner 23d outputs that "Ch1 has no contact" with a finger.

<Step S150>

The finger misplacement degree determiner 23d outputs that the finger is "misplaced in the left (−P) direction".

<Step S151>

Based on the presence or absence of a signal on Ch3, the finger misplacement degree determiner 23d determines whether a finger of the right hand is rested on Ch3, i.e., the auxiliary electrode 48c.

<Step S152>

The finger misplacement degree determiner 23d outputs that the finger is "misplaced in the right (+P) direction".

<Step S153>

The finger misplacement degree determiner 23d outputs that the electrodes have "no contact" with the fingers.

(Example Determination of States of Finger Misplacement)

In the variety of states of finger misplacement shown in FIGS. 16A to 16D, processes based on the flow shown in FIG. 19 will be described with reference to the second and third states of FIGS. 16B and 16C.

In the second state, it is determined at step S141 that there is no signal on Ch2, and then at step S142 it is output that "Ch2 does not have contact". Control then proceeds to step S145, where it is determined that there is no signal on Ch1, and then at step S147 it is output that "Ch1 does not have contact". Control then proceeds to step S151, where it is determined that there is a signal on Ch3, and then at step S53 it is output that the finger is "misplaced in the right (+P) direction" as shown in FIG. 18, and the contact state analysis process is ended.

In the third state, it is determined at step S141 that there is no signal on Ch2, and then at step S142 it is output that "Ch2 does not have contact". Control then proceeds to step S145, where it is determined that there is a signal on Ch1, and it is output that the finger is "misplaced in the right (+P) direction" as shown in FIG. 18, and the contact state analysis process is ended.

FIG. 20A to FIG. 20D show exemplary data of states of finger misplacement (first to fourth states) in FIGS. 16A to 16D.

In the first state shown in FIG. 20A, no finger is rested on any of the main electrode 48a and the auxiliary electrodes 48b, 48c, 49b, and 49c. Therefore, for all of Ch1 to Ch5, a waveform of amplified extrinsic noise is observed, rather than a biological signal waveform.

In the second state shown in FIG. 20B, since no finger is rested on the main electrode 48a, a waveform of amplified extrinsic noise is observed on Ch1, rather than a biological signal waveform. Since no finger is rested on the auxiliary electrode 48b, a waveform of amplified extrinsic noise is observed on Ch2. Since a finger is rested on the auxiliary electrode 48c, an electrocardiographic waveform measurable between Ch3 and Ref is observed on Ch3. Since a finger is rested on each of the auxiliary electrodes 49b and 49c, bioelectric potential waveforms representing potential differences from Ref are observed on Ch4 and Ch5.

The third state shown in FIG. 20C differs from the second state with respect to the contact state of Ch1. Specifically, since a finger is rested on the main electrode 48a, an electrocardiographic waveform measurable between Ch1 and Ref is observed on Ch1. On Ch2 to Ch5, waveforms of similar magnitudes to those in the second state are observed. However, the electrocardiographic waveform observed on Ch3 has a smaller amplitude than does the electrocardiographic waveform on Ch1 because the area of contact for the auxiliary electrode 48c is smaller than the area of contact for the main electrode 48a.

In the fourth state shown in FIG. 20D, since a finger is rested on every one of the main electrode 48a and the auxiliary electrodes 48b, 48c, 49b, and 49c, or the degree of finger misplacement is sufficiently small, biological signals are observed on all of Ch1 to Ch5. The same potential is measured at the main electrode 48a and the auxiliary electrodes 48b and 48c.

From the relationship between the measured waveforms, a contact state determination section, which will be described later, determines degrees of misplacement (contact states) between finger positions and the positions of the main electrode 48a and the auxiliary electrodes 48b, 48c, 49b, and 49c.

(Application Processor)

FIG. 21 shows a flow of biological information processing at the application processor 24. Processes from step S161 to step S177 are performed. The flow of FIG. 21 will be described with reference to a displayed image of FIG. 22. FIG. 22 gives a see-through view of electrode deployment, where the electrodes provided on the rear face of the controller 1 are seen through the front face of the controller 1. Therefore, the state of finger misplacement shown in FIG. 22 indicates that the right hand is misplaced in the −P direction. On the other hand, the third state of finger misplacement shown in FIG. 16C indicates that the left hand is misplaced in the +P direction. The display screen equipment which displays the image of FIG. 22 may be the display screen equipment 3 in FIG. 1 or the display screen 47 in FIG. 2B. Note that FIG. 22 illustrates an example of a display screen. As shown in FIG. 22, in addition to a waveform 47a which is currently being measured, any electrode on the rear face that is in contact with a finger is indicated in color as a corresponding electrode icon 47b on the screen. Any electrode icon 47b corresponding to an electrode that is not in contact with a finger remains white.

<Step S161>

Based on an output result from the biological signal processor 23, it is determined whether contact is missing from all the electrodes corresponding to Ch1 to Ch3.

<Step S162>

Since all the electrodes corresponding to Ch1 to Ch3 lack contact, a message "there is no contact" is displayed on the display screen 47, and the process is ended. This message is displayed by the contact state display 47c in FIG. 22.

<Step S163>
By using the output result from the biological signal processor 23, it is determined whether the electrode corresponding to Ch1 has contact or not.

<Step S164>
Since the electrode corresponding to Ch1 has contact, the electrode icon on the display screen corresponding to Ch1 is highlighted. The highlight is indicated as an electrode icon 47b1 on the contact state display 47c in FIG. 22.

<Step S165>
The signal waveform measured on Ch1 is displayed by the waveform display 47a in FIG. 22.

<Step S166>
By using the output result from the biological signal processor 23, it is determined whether the electrode corresponding to Ch2 has contact or not.

<Step S167>
Since the electrode corresponding to Ch2 has contact, the electrode icon on the display screen corresponding to Ch2 is highlighted. The highlight is indicated as an electrode icon 47b2 on the contact state display screen 47c in FIG. 22.

<Step S168>
It is determined whether the waveform display 47a of the display screen 47 is already displaying a signal waveform on Ch1.

<Step S169>
The signal waveform measured on Ch2 is displayed by the waveform display 47a in FIG. 22.

<Step S170>
By using the output result from the biological signal processor 23, it is determined whether the electrode corresponding to Ch3 has contact or not.

<Step S171>
Since the electrode corresponding to Ch3 has contact, the electrode icon on the display section corresponding to Ch3 is highlighted. The highlight is indicated as an electrode icon 47b3 on the contact state display 47c in FIG. 22.

<Step S172>
It is determined whether the waveform display 47a of the display screen 47 is already displaying a signal waveform on Ch1 or Ch2.

<Step S173>
The signal waveform measured on Ch3 is displayed by the waveform display 47a in FIG. 22.

<Step S174>
By using the output result from the biological signal processor 23, it is determined whether the finger is misplaced to the right or not.

<Step S175>
A message "misplaced in the right (−P) direction" is displayed by the finger misplacement information display 47d of the display screen 47 shown in FIG. 22. Furthermore, the misplacement direction display 47e displays a rightward arrow indicating the direction of misplacement, and the process is ended.

<Step S176>
By using the output result from the biological signal processor 23, it is determined whether the finger is misplaced to the left or not.

<Step S177>
A message "misplaced in the left (+P) direction" is displayed by the finger misplacement information display 47d of the display screen 47 shown in FIG. 22. Furthermore, the misplacement direction display 47e displays a leftward arrow indicating the direction of misplacement, and the process is ended.

(Effects)
Thus, by using bioelectric potential sensors mounted on the controller 1, it is possible to determine a position of finger contact with an electrode and a state of misplacement, from the information of a bioelectric potential acquired with the main electrode section 13a and the auxiliary electrode section 13b.

Other Embodiments

By disposing the auxiliary electrode section 13b in directions in which fingers are likely to be misplaced, the user's attention can be immediately called as soon as a finger misplacement occurs, whereby more stable bioelectric potential measurements are enabled. By disposing the auxiliary electrode section 13b, even when no finger is rested on the main electrode section 13a, the auxiliary electrode on which the finger is rested can now be used as the measurement electrode, so that a bioelectric potential which is measured with the auxiliary electrode can be adopted as an output potential waveform. Since the auxiliary electrode can measure at least a little bit of bioelectric potential, the amplifier in the biological signal amplifier for amplifying the signal for measurement is prevented from saturation, whereby more stable bioelectric potential measurement is enabled.

In the present embodiment, the electrode deployment is defined in such a manner that the left main electrode 49a of the controller 1 is the reference electrode (Ref). However, the reference electrode may be switched to the left main electrode 48a depending on changes in the contact state. Similar processing can be realized by reading the signals picked up from the right and left electrodes in reverse order.

As for the method of switching, a reference electrode selector 14a may be provided before the biological signal amplifier 14 as shown in FIG. 23, and in accordance with the register value of a reference electrode selection signal Ref_CH, whichever electrode that needs to be set as reference electrode is connected to a reference electrode input (Ref) of the biological signal amplifier 14. For example, when the main electrode 48a is to be the reference electrode, the register value of the reference electrode selection signal Ref_CH may be set to a value corresponding to the main electrode 48a. The main electrode 48a is connected to Ref of the biological signal amplifier 14, and instead, the main electrode 49a is connected to Ch1 of the biological signal amplifier 14. Otherwise, the relative connection of Ch2 to Ch4 is similar to the connections in FIG. 13. Herein, in the biological signal amplifier 14, it is now the potential of the main electrode 48a that is the signal from which differences of Ch1 to Ch5 are to be taken. Thus, by providing the reference electrode selector 14a, it becomes possible to switch the reference electrode from Ref to any of the signals on Ch1 to Ch5, whereby more flexible bioelectric potential measurement is enabled depending on changes in the contact state.

As shown in FIG. 24, the electrode section 13 may be composed of an active electrode section 13c. An electrode which is connected to the input of an active electrode amplifier 80 is referred to as an active electrode. In the active electrode section 13c, main electrodes 48a and 49a and auxiliary electrodes 48b, 48c, 49b, and 49c are each connected to the input of an active electrode amplifier 80, and the respective outputs of the active electrode amplifiers are connected to corresponding inputs Ch1 to Ch5 and Reflect of the biological signal amplifier 14. Since the active electrode amplifiers 80 are able to suppress an extrinsic noise component associated with a commercial power of 50 Hz or 60 Hz, called hum noise, it is possible to stably measure a bioelectric potential without amplifying any unwanted signal in the biological signal amplifier 14. Furthermore, even if wiring that interconnects the active electrode section 13c and the biological signal amplifier 14 vibrates due to hand vibration, the active electrode amplifier 80 suppresses potential fluctuations associated with the wiring vibration, thereby enabling more stable bioelectric potential measurement.

Note that, as shown in FIG. 25, if the finger direction is known in advance because of the shape or the like of the controller 1, the electrode section 13 may be composed of the main electrode 54a and a single auxiliary electrode 54b. The example shown in FIG. 25 illustrates the deployment of the electrode section 13 in the case where the finger may only be misplaced in the right direction. This relative positioning is such that, when the pad of a finger is placed on the center of the main electrode 54a, the two auxiliary electrodes 54b and 54c will both abut with the finger. That is, assuming a diameter X of the main electrode 54a, a width Y of the auxiliary electrode 54b, an interspace D between the main electrode 54a and the auxiliary electrodes 54b and 54c, and a diameter F of the contact range of the finger, it is desirable that the relationship of eq. 2 below is satisfied.

$$X+D+Y \leq F \quad \text{(eq. 2)}$$

Instead of the relative positioning between the main electrode section and the auxiliary electrode section shown in FIG. 12, electrode positioning as shown in FIG. 26A may be adopted. When the main electrode 54a abuts with the pad of a finger, the auxiliary electrodes 54b and 54c are located outside the contact range of the finger. FIG. 26B shows ranges in which the fingers may be in contact with the electrodes when the controller is gripped by both hands. Usually, where there is no finger misplacement, the fingers are not rested on any of the auxiliary electrodes 48b, 48c, 49b, and 49c. The auxiliary electrodes 48b, 48c, 49b, and 49c are located at positions which are distant from the center of the main electrode 54a within a predetermined range (e.g., the contact range of the user's finger). For example, the distance from the center of the main electrode 54a to the edge of the auxiliary electrode 48b, 48c, 49b, 49c is smaller than the radius of the contact range of the user's finger. From the size of the main electrode 54a, the predetermined distance between the main electrode 54a and the auxiliary electrode 48b, 48c, 49b, 49c is to be determined.

The user's finger being in contact with any of the auxiliary electrodes 48b, 48c, 49b, and 49c leads to a determination that the user's finger is misplaced.

For example, when a finger of the left hand is misplaced in the right (+P) direction in the figure, the finger becomes rested on the auxiliary electrode 48c as well as on the main electrode 48a, whereby it can be determined that the finger is misplaced to the right. When a finger of the left hand is further misplaced to the right so as to be rested only on the auxiliary electrode 48c, it can also be determined that the finger is excessively misplaced to the right from the main electrode 48a. Furthermore, this electrode positioning, in which the tolerable range for finger misplacement is limited, is useful when a screw hole, a dent, or the like exists near the electrode section disposed on the controller so that any finger being misplaced from the main electrode section may cause a significantly deteriorated contact state.

As shown in FIG. 26B, when the main electrode and auxiliary electrodes are spaced apart by a predetermined distance or longer, the user's finger is misplaced in the direction of an auxiliary electrode that indicates presence of contact information. Herein, in the prestored relationship, the user's contact information is associated with the direction of the auxiliary electrode that has contact information being the direction of misplacement of the user's finger, unlike in the relationship shown in FIG. 18 between the electrode positions and the user's electrode contact information and the user's direction of misplacement.

Figure 27A:
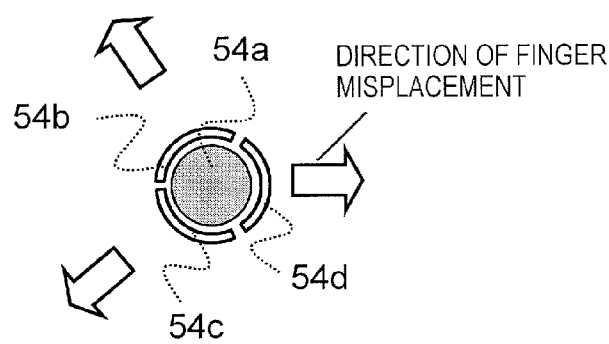
Figure 27B:
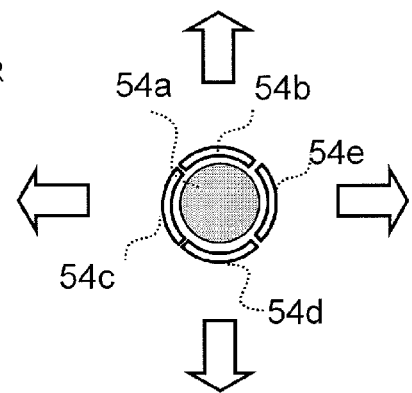
Figure 27C:
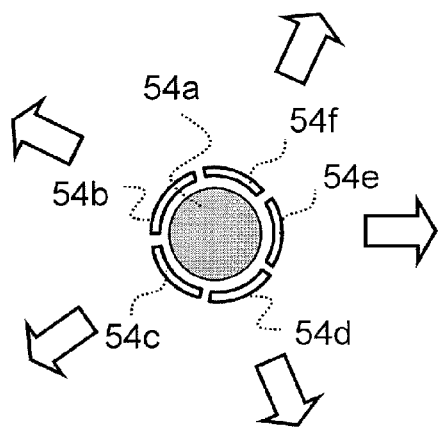
Figure 27D:
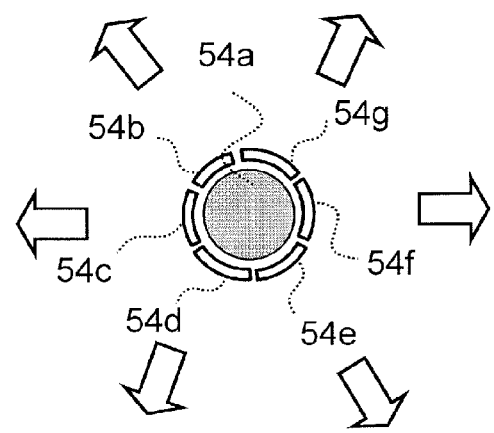
Figure 28A:
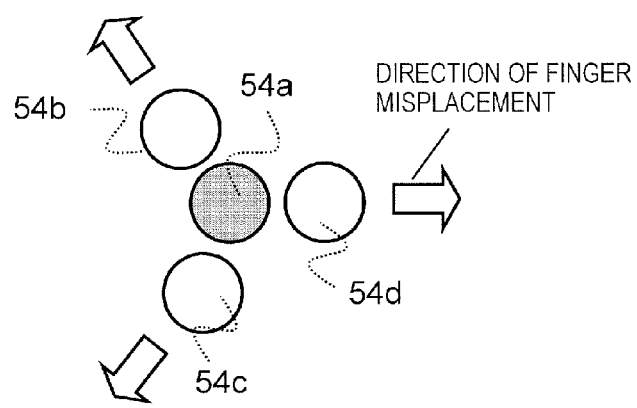
Figure 28B:
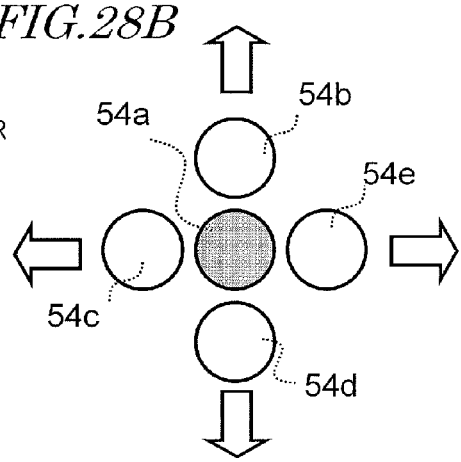
Figure 28C:
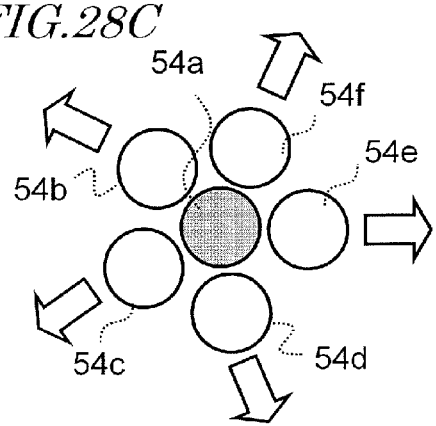
Figure 28D:
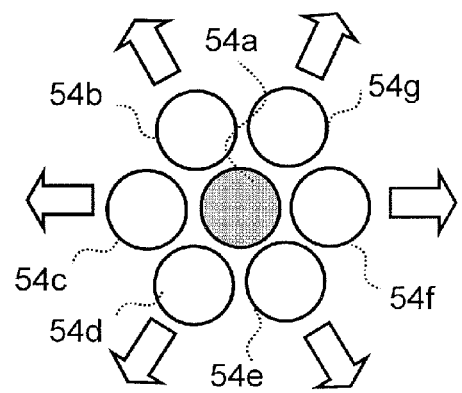
Figure 29A:
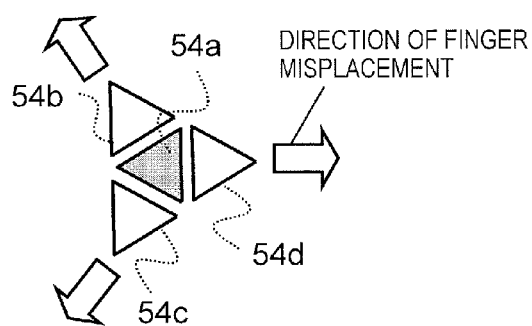
Figure 29B:
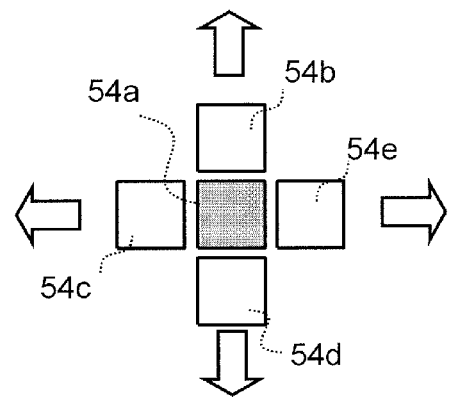
Figure 29C:
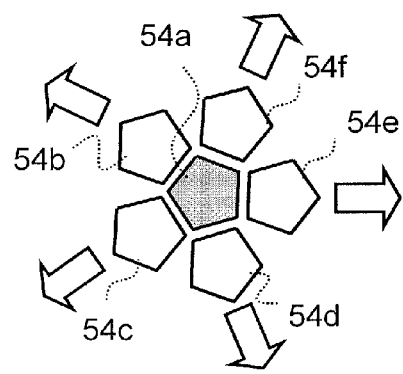
Figure 29D:
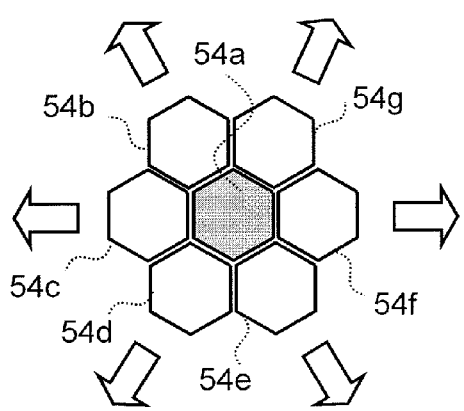

As for the electrode positioning in the electrode section 13, as shown in FIGS. 27A to 27D, FIGS. 28A to 28D, and FIGS. 29A to 29D, the auxiliary electrode section 13b may be placed in a polygonal deployment around the main electrode section 13a disposed in the center. For example, in the case of FIG. 27A, finger misplacement is detectable in three directions. In the case of FIG. 27B, finger misplacement is detectable in four directions of up/down/right/left. In the case of FIG. 27C, finger misplacement is detectable in five directions in a star shape. In the case of FIG. 27D, finger misplacement is detectable in six directions. FIGS. 28A to 28D show the main electrode section 13a and auxiliary electrode section 13b being composed alike of identical circular electrodes, similarly to FIGS. 26A to 26B. FIGS. 29A to 29D shows an example where the main electrode section 13a and the auxiliary electrode section 13b have polygonal electrode shapes. In particular, in FIG. 29D, the main electrode section 13a and the auxiliary electrode section 13b are composed alike of identical hexagonal electrodes, this being optimum in terms of areal efficiency around the central electrode and providing an advantage in that the direction of misplacement can be efficiently identified.

In either case, it can be said that a plurality of auxiliary electrodes are placed in symmetric positions with respect to the main electrode. More specifically, a plurality of auxiliary electrodes are placed in point symmetric positions around the main electrode in the center, or in axisymmetric positions with respect to an axis passing through the main electrode.

Note that, as shown in FIG. 30, a current source 90 which is connected to each of the main electrodes 48a and 49a and auxiliary electrodes 48b, 48c, 49b, and 49c in the electrode section 13 may be additionally provided, thus providing a function of measuring contact impedance between an electrode and a finger. With an AC current (e.g., a rectangular wave with a frequency of 1 kHz) generated by the current source 90, the contact impedance between each electrode and a finger can be measured. A low-frequency biological signal and a potential corresponding to a high-frequency contact impedance are superposed in the potential which is measured with each electrode. Since the biological signal amplifier 14 only amplifies the biological signal whereas the contact impedance measurement circuit 14z only extracts a frequency component near the band (frequency: 1 kHz) of the AC current, the biological signal and the contact impedance, even if simultaneously measured, can be isolated from each other. Signals Ch1z to Ch5z which have been measured by the contact impedance measurement circuit are sent to the biological signal output section 15.

FIG. 31 shows the construction of the biological signal processor 23. From the signals Ch1z to Ch5z acquired by the biological signal acquisition section 22, the contact impedance evaluation section 23e of the contact state analyzer 23b quantitatively calculates contact impedances of the electrodes corresponding to Ch1 to Ch5 in FIG. 25. Based on the contact impedance values, the finger misplacement degree determiner 23d is able to determine positions of contact of the electrodes and states of finger misplacement according to a flowchart similar to that of FIG. 19.

FIG. 32 is a lookup table showing relative largeness/smallness of the contact impedance of each Ch corresponding to the state of finger misplacement in FIG. 16. Generally speaking, there is low contact impedance when an electrode has contact, and there is high contact impedance when an electrode has no contact. This construction provides an advantage in that the specific degree of contact can be known from the relative largeness/smallness of contact impedances.

In the case where the bioelectric potential waveform is an electrocardiographic waveform, an R wave may be extracted, and an instantaneous heart rate per minute may be calculated from the interval between R waves for indication as shown in FIG. 22. This provides an effect of being able to inform the user of an active or rested state, or a health state.

Embodiment 2

The information processing system according to the present embodiment has the same fundamental overall construction as the construction shown in FIG. 7 and FIG. 8. Therefore, differences from the construction in Embodiment 1 i.e., the construction of the electrode section 13, processing by the contact state analyzer 23b of the biological signal processor 23, and processing by the application processor 24, will be described.

(Electrode Section)

FIG. 33A shows the construction of the electrode section 13. A circular main electrode 54a is disposed in the center. Two auxiliary electrodes 54b and 54 are disposed in one direction (i.e., the lower direction in this figure) outside the main electrode 54a. That is, at least a plurality of auxiliary electrodes are disposed in the same direction from the main electrode in the center. For example, no auxiliary electrode may be provided in directions in which it is previously known that finger misplacement is unlikely to occur.

The directions in which the user's finger is likely to be misplaced and the directions in which the user's finger is unlikely to be misplaced are determined from, for example, relative positioning of the operation buttons provided on the manipulation surface 43, the shape of the housing of the controller 1, or the position of the main electrode, etc.

For example, since there is a possibility that the user's finger may be misplaced in the direction of gravity, i.e., away from the position opposing an operation button on the rear face 46 of the controller 1, a plurality of auxiliary electrodes may be provided.

For example, given the manner in which the user will grip the controller 1, finger misplacement is considered unlikely to occur in the central direction of the controller in the case where the main electrodes are located in positions that are close to the center of the rear face 46 of the controller 1. In this case, no auxiliary electrodes may be provided.

The expected size for the electrode section 13 is indicated by dimensions shown in FIG. 33A, which are determined from the fact that a finger contact range has a circle shape with a diameter of F=14 mm. The main electrode 54a has a diameter X of 10 mm, and the auxiliary electrode 54b has a width (i.e., length along the normal direction of the main electrode 54a) Y of 1 mm.

This relative positioning is such that, when the pad of a finger is placed on the center of the main electrode 54a, neither of the two auxiliary electrodes 54b and 54c abuts with the finger. In other words, assuming a diameter X of the main electrode 54a and an interspace D between the main electrode 54a and the auxiliary electrode 54b, it is desirable that the relationship of eq. 3 below is satisfied.

$$X+D \geq F \qquad \text{(eq. 3)}$$

It is desirable that the electrodes are sized so as to result in a similar figure to what is defined by the dimensions shown in FIG. 33A, based on the actual contact range of a finger.

FIG. 33B shows an example where the electrodes are placed on the rear face of the controller 1. In a state where the controller is gripped by both hands, the electrode section 13 is composed of the main electrode 48a and two auxiliary electrodes 48b and 48c placed at the right side in the figure as well as the main electrode 49a and two auxiliary electrodes 49b and 49c placed at the left side in the figure. As described above, the left hand of the user may be in contact with the main electrode 48a and the two auxiliary electrodes 48b and 48c, and the right hand may be in contact with the main electrode 49a and the two auxiliary electrodes 49b and 49c. The auxiliary electrodes 48b and 48c are disposed in a lower obliquely right direction in the figure (+Q direction) of the main electrode 48a, whereas the auxiliary electrodes 49b and 49c are disposed in a lower obliquely left direction (+R direction) of the main electrode 49a.

In the example of FIG. 33B, when the pad of the left middle finger and the pad of the right middle finger of the user are rested respective on the main electrodes 48a and 49a, no fingers are rested on the auxiliary electrodes 48b, 48c, 49b, and 49c. Hereinafter, in FIG. 33B, the right main electrode 48a will be referred to as a measurement electrode (Ch1) and the left main electrode 48b as a reference electrode (Ref) in the following description. Furthermore, as shown in FIG. 33B, auxiliary electrodes 48b, 48c, 49b, and 49c are designated Ch2, Ch3, Ch4, and Ch5, respectively.

(Processing by Contact State Analyzer)

FIG. 34 shows an example flow of the contact state analysis process by the contact state analyzer 23b. One difference from the flow shown in FIG. 15 is the addition of step S114 to the processes form steps S111 to S113. Step S111 is processed by the signal detector 23c. Steps S112 to S114 are processed by the finger misplacement degree determiner 23d.

The finger misplacement degree determiner 23d stores therein a relationship between the electrode positions and electrode contact information of the user, the directions of misplacement of the user, and the degree of finger misplacement.

<Step S111>

The signal detector 23c detects signals on Ch1 to Ch5.

<Step S112>

The finger misplacement degree determiner 23d detects the position of contact of an electrode corresponding to each signal from Ch1 to Ch5.

<Step S113>

The finger misplacement degree determiner 23d refers to a relationship stored therein to detect a direction of finger misplacement based on the information of the position of electrode contact.

<Step S114>

The finger misplacement degree determiner 23d refers to the prestored relationship to detect a degree of finger misplacement based on the information of the position of electrode contact.

(Example States of Finger Misplacement)

FIGS. 35A to 33C show various states of finger misplacement that may occur when the controller 1 is gripped by both hands in the present embodiment. The first state shown in FIG. 35A is a case where a finger of the left hand is rested only on the main electrode 48a, whereas a finger of the right hand is rested only on the main electrode 49b. The second state shown in FIG. 35B is a case where a finger of the right hand is rested only on the main electrode 49a, whereas a finger of the left hand is misplaced in a lower obliquely right direction of the figure indicated by an arrow, so as to be rested on the auxiliary electrodes 48b and 48c. The third state shown in FIG. 35C is a case where a finger of the right hand is rested only on the main electrode 49a, whereas a finger of the left hand is misplaced further in the lower obliquely right direction from the second state, so as to be rested only on the auxiliary electrode 48c. By using the signal detector 23c and the finger misplacement degree determiner 23d in the contact state analyzer 23b of FIG. 14, it is possible to distinguish each of the aforementioned three states.

FIG. 36 shows a lookup table of signal detection for Ch1 to Ch5, as determined with respect to example states of finger misplacement shown in FIGS. 35A to 35C by using the signal detector 23c. In the first to third states, for each Ch, "YES" is indicated where a biological signal is found to exist, and "NO" is indicated where no biological signal is found to exist.

(General Flow of Processing by Contact State Analyzer)

FIG. 37 shows a flow of processing by the contact state analyzer 23b. There are processes from step S241 to step S248.

<Step S241>

Based on the presence or absence of a signal on Ch1, the finger misplacement degree determiner 23d determines whether a finger of the right hand is rested on Ch1, i.e., the main electrode 48a.

<Step S242>

The finger misplacement degree determiner 23d outputs that "Ch1 has no contact" with a finger.

<Step S243>

Based on the presence or absence of a signal on Ch2, the finger misplacement degree determiner 23d determines whether a finger of the right hand is rested on Ch2, i.e., the auxiliary electrode 48b.

<Step S244>

The finger misplacement degree determiner 23d outputs information concerning the direction and degree of misplacement, and the process is ended. Specifically, the finger misplacement degree determiner 23d outputs information indicating that the finger is "misplaced by one electrode in the lower right (+Q) direction".

<Step S245>

The finger misplacement degree determiner 23d outputs that "Ch2 has no contact" with a finger.

<Step S246>

Based on the presence or absence of a signal on Ch3, the finger misplacement degree determiner 23d determines whether a finger of the right hand is rested on Ch3, i.e., the auxiliary electrode 48c.

<Step S247>

The finger misplacement degree determiner 23d outputs information concerning the direction and degree of misplacement, and the process is ended. Specifically, the finger misplacement degree determiner 23d outputs information indicating that the finger is "misplaced by two electrodes in the lower right (+Q) direction".

<Step S248>

The finger misplacement degree determiner 23d outputs that the electrodes have "no contact" with the fingers, and the process is ended.

(Example Determination of States of Finger Misplacement)

In the variety of states of finger misplacement shown in FIGS. 35A to 35C, processes based on the flow shown in FIG. 37 will be described with reference to the second and third states of FIGS. 35B and 35C.

In the second state, it is determined at step S241 that there is no signal on Ch1, and then at step S242, it is output that "Ch1 does not have contact". Control then proceeds to step S243, where it is determined that there is a signal on Ch2, and then at step S244, it is output that a finger is "misplaced by one electrode in the lower right (+Q) direction" as shown in FIG. 36, and the contact state analysis process is ended.

In the third state, it is determined at step S241 that there is no signal on Ch1, and then at step S242, it is output that "Ch1 does not have contact". Control then proceeds to step S243, where it is determined that there is no signal on Ch2, and then at step S245, it is output that "Ch2 does not have contact". Control proceeds to step S246, where it is determined that there is a signal on Ch3, and then at step 247, it is output that a finger is "misplaced by two electrodes in the lower right (+Q) direction" as shown in FIG. 36, and the contact state analysis process is ended.

FIG. 38A to FIG. 38C show exemplary data of states of finger misplacement (first to third states) in FIGS. 35A to 35C.

In the first state shown in FIG. 38A, since a finger is rested on the main electrode 48a, an electrocardiographic waveform measurable between Ch1 and Ref is observed on Ch1. On the other hand, since no fingers are rested on the auxiliary electrodes 48b, 48c, 49b, and 49c, a waveform of amplified extrinsic noise is observed, for all of Ch2 to Ch5, rather than a biological signal waveform.

In the second state, since no finger is rested on the main electrode 48a, a waveform of amplified extrinsic noise is observed on Ch1, rather than a biological signal waveform. Since a finger is rested on the auxiliary electrode 48b, an electrocardiographic waveform measurable between Ch2 and Ref is observed on Ch2. Since a finger is rested on the auxiliary electrode 48c, an electrocardiographic waveform measurable between Ch3 and Ref is observed on Ch3. Since no fingers are rested on auxiliary the electrodes 49b and 49c, waveforms of amplified extrinsic noise are observed on Ch4 and Ch5.

The third state differs from the second state with respect to the contact state of Ch2. Since no finger is rested on the auxiliary electrode 48b a waveform of amplified extrinsic noise is observed on Ch2, rather than a biological signal.

(Application Processor)

FIG. 39 shows a flow of biological information processing by the application processor 24. Processes from step S161 to step S173 and step S181 to step S184 are performed. Differences from FIG. 21 are the processes from step S181 to step S184.

The flow of FIG. 39 will be described with reference to a displayed image of FIG. 40. FIG. 40 gives a see-through view of electrode deployment, where the electrodes provided on the rear face of the controller 1 are seen through the front face of the controller 1. Therefore, the state of finger misplacement shown in FIG. 40 indicates that the right hand is misplaced in the +R direction. On the other hand, the third state of finger misplacement shown in FIG. 35C indicates that the left hand is misplaced in the +Q direction. The display section which displays the image of FIG. 40 may be the display section 3 in FIG. 1 or the display screen 47 in FIG. 2B. Note that FIG. 40 illustrates an example of a display section. As shown in FIG. 40, in addition to a waveform 47a which is currently being measured, any electrode on the rear face that is in contact with a finger is indicated in color as a corresponding electrode icon 47b on the screen. Any electrode icon 47b corresponding to an electrode that is not in contact with a finger remains white.

<Step S161>
Based on an output result from the biological signal processor 23, it is determined whether contact is missing from all the electrodes corresponding to Ch1 to Ch3.

<Step S162>
Since all the electrodes corresponding to Ch1 to Ch3 lack contact, a message "there is no contact" is displayed on the display screen 47, and the process is ended. This message is displayed by the contact state display 47c in FIGS. 35A to 35C.

<Step S163>
By using the output result from the biological signal processor 23, it is determined whether the electrode corresponding to Ch1 has contact or not.

<Step S164>
Since the electrode corresponding to Ch1 has contact, the electrode icon on the display section corresponding to Ch1 is highlighted. The highlight is indicated as an electrode icon 47b1 on the contact state display 47c in FIG. 40.

<Step S165>
The signal waveform measured on Ch1 is displayed by the waveform display 47a in FIG. 40.

<Step S166>
By using the output result from the biological signal processor 23, it is determined whether the electrode corresponding to Ch2 has contact or not.

<Step S167>
Since the electrode corresponding to Ch2 has contact, the electrode icon on the display section corresponding to Ch2 is highlighted. The highlight is indicated as an electrode icon 47b2 on the contact state display 47c in FIG. 40.

<Step S168>
It is determined whether the waveform display 47a of the display screen 47 is already displaying a signal waveform on Ch1.

<Step S169>
The signal waveform measured on Ch2 is displayed by the waveform display 47a in FIG. 40.

<Step S170>
By using the output result from the biological signal processor 23, it is determined whether the electrode corresponding to Ch3 has contact or not.

<Step S171>
Since the electrode corresponding to Ch3 has contact, the electrode icon on the display section corresponding to Ch3 is highlighted. The highlight is indicated as an electrode icon 47b3 on the contact state display 47c in FIG. 40.

<Step S172>
It is determined whether the waveform display 47a of the display screen 47 is already displaying a signal waveform on Ch1 or Ch2.

<Step S173>
The signal waveform measured on Ch3 is displayed by the waveform display 47a in FIG. 40. For example, in the third state of FIG. 30, the electrode only has contact on Ch3 while the electrodes lack contact on Ch1 and Ch2. Therefore, Ch3 is regarded as the electrocardiographic waveform data obtained with the measurement electrode, and the electrocardiographic waveform is displayed on the waveform display 47a.

<Step S181>
By using the output result from the biological signal processor 23, it is determined whether a finger is misplaced by one electrode in the lower right direction or not.

<Step S182>
A message "misplaced by one electrode in the lower right (+R) direction" is displayed by the finger misplacement information display 47d of the display screen 47 shown in FIG. 40. Furthermore, the misplacement direction display 47e displays a rightward arrow indicating the direction of misplacement, and the process is ended.

<Step S183>
By using the output result from the biological signal processor 23, it is determined whether a finger is misplaced by two electrodes in the lower right direction or not.

<Step S184>
A message "misplaced by two electrodes in the lower right (+R) direction" is displayed by the finger misplacement information display 47d of the display screen 47 shown in FIG. 40. Furthermore, the misplacement direction display 47e displays a leftward arrow indicating the direction of misplacement, and the process is ended.

(Effects)

Thus, by using bioelectric potential sensors mounted on the controller 1, it is possible to determine a position of finger contact with an electrode and a state of misplacement, from the information of a bioelectric potential acquired with the main electrode section 13a and the auxiliary electrode section 13b. By placing the plurality of auxiliary electrodes 48b and 48c in directions in which fingers are likely to be misplaced, not only the direction of finger misplacement but also the degree of misplacement can be immediately notified to the user. Moreover, the present embodiment makes it possible to continuously output a biological signal in spite of a certain degree of finger misplacement. Thus, various hand sizes are supported, and various placements of fingers when gripping the controller 1 is supported.

Since the auxiliary electrode section 13b on the rear face 46 of the controller 1 shown in FIG. 33B is placed at both ends along the longitudinal direction of the controller 1, the wiring between the electrode section 13 and the biological signal amplifier 14 does not involve any crossing. This provides an effect in that a biological signal can be stably measured without allowing unwanted extrinsic noise to occur.

Variant of Embodiment 2

In Embodiment 2, by placing a plurality of auxiliary electrodes around a main electrode, the degree of finger misplacement is measured, on which basis of which attention of the user is called. In the present variant, even more auxiliary electrodes are provided in a direction in which finger misplacement is highly likely. For example, as shown in FIG. 41, four auxiliary electrodes 48b (Ch2), 48c (Ch3), 48d (Ch4), and 48e (Ch5) are provided for one main electrode 48a (Ch1). By placing many electrodes, it is possible to take specific measurements of the degree of finger misplacement. Furthermore, by utilizing the information of chronological changes in the degree of finger misplacement, it is possible to take specific measurements of the degree of contact between the user's finger and an electrode.

For example, while the user's finger moves between the main electrodes Ch1 and Ch2 in a short time, there is a presumably small possibility that the user's finger may go off the electrode. However, while the electrode to be touched by the finger moves from Ch1 to Ch2, Ch3, Ch4, or Ch5, there is a large possibility that the finger may go off the electrode. As shown in FIG. 42, a finger misplacement chronological pattern storage 4301 is added to the system construction of Embodiment 2. Otherwise, the construction and operation are similar to those of Embodiment 2, and the descriptions thereof are omitted.

In the finger misplacement chronological pattern storage 4301, states of finger misplacement over lapse of time are stored. For example, the content shown in FIGS. 43A and 43B may be stored. In FIG. 43A, for Ch1 to Ch5, different states are defined based on which electrode a bioelectric potential is being measured on. For example, there are three S1 states: a case where potential is being measured on Ch1; a case where potential is being measured at the two of Ch1 and Ch2; and a case where potential is being measured at the three electrodes of Ch1, Ch2, and Ch3. Thus, states are defined based on the electrode at which measurement is being taken. Furthermore, patterns of change between states in (a) are stored as shown in FIG. 43B, against chronological changes in finger misplacement.

For example, if a movement from S1 to S3, or from S1 to S4, occurs within a predetermined time, it is known that a finger is being misplaced. On the other hand, a movement from S1 to S2 and then back to S1 occurs within a predetermined time, this can be interpreted to mean that the finger is oscillating between the electrodes. Thus, from a chronological pattern of a moving finger from electrode to electrode, a finger state can be detected, and notified to the user.

Embodiment 3

Embodiments 1 and 2 illustrate examples where electrodes are placed on the rear face 46 of the controller 1, such that finger misplacements with respect to the main electrodes are measured. The present embodiment illustrates an example where electrodes are provided also on the manipulation surface 43 of the controller to realize more reliable bioelectric potential measurements. Embodiments 1 and 2 illustrate detection of a finger misplacement during game play. On the other hand, the present embodiment is available for allowing a user to know the feel of being in contact with the electrodes, prior to playing a game.

On the manipulation surface, finger positions will move a lot because manipulation of a game or the like is performed with the buttons. However, unlike on the rear face, the user is able to use the eyes to confirm which places are being pressed. In the case where electrodes are provided on the buttons, the fingers will always be in contact with the electrodes so long as the buttons are being pressed.

Therefore, in the present embodiment, electrodes are provided on buttons which are placed on the manipulation surface of a controller, and as the user is instructed to press down predetermined buttons, it is ensured that there will be fingers in contact with the electrodes. For example, electrodes may be placed as shown in FIGS. 44A and 44B. FIG. 44A illustrates an auxiliary electrode section 13b which is deployed on the buttons on the manipulation surface 43 of a stick-type controller. FIG. 44B illustrates an auxiliary electrode section 13b which is deployed on the buttons of the manipulation surface 43 of a pad-type controller. The system construction of present embodiment, in particular the construction of the biological signal processor 23, is shown in FIG. 45. In FIG. 45, the contact state analyzer 23b additionally includes a manipulation-surface electrode signal detector 4601 for detecting a biological signal from an electrode which is provided on the manipulation surface, and a rear-face electrode signal detector 4602 for detecting a biological signal from an electrode which is provided on the rear face of the controller. As shown in FIG. 46, one of the electrodes provided on the manipulation surface 43 is defined as a Ch1 (Ref) electrode, and the electrodes to be touched with a finger of the other hand are defined as a Ch2 electrode. A potential difference between these electrodes is measured by the manipulation-surface electrode signal detector 4601. On the rear face 46, main electrodes Ch3 and Ch5 and auxiliary electrodes Ch4 and Ch6 are provided. Against Ch1 (Ref) as a reference potential, the potentials of Ch3, Ch4, Ch5, and Ch6 are measured by the rear-face electrode signal detector 4602.

In the present embodiment, a user who is going to play a game or the like while holding the controller is first instructed to touch the electrodes on the manipulation surface, as shown in FIG. 47. Once it is confirmed that the user has pressed the buttons on the manipulation surface, a potential as shown in FIG. 48 is measured by the manipulation-surface electrode signal detector 4601. After such a potential is measured, as shown in FIG. 49, the user is then instructed to place fingers on the electrodes provided on the rear face of the controller. At this time, if fingers are accurately in contact with the electrodes on the rear face of the controller, data as shown in FIGS. 50A and 50B is measured. FIG. 50A illustrates an example waveform under accurate measurement, whereas FIG. 50B shows an example waveform when a finger of the right hand is slightly misplaced. If accurate measurement is taking place, heartbeats will be measured on Ch5. If a finger is in contact with Ch5 and Ch6, heartbeats will be measured on Ch5 and Ch6. When such potentials are measured, it can be confirmed that the user's fingers are in contact with the electrodes.

In this manner, it can be ensured that the user will play a game after it is confirmed that his or her fingers are in contact with the electrodes.

The operation of the above system will be described. FIG. 51 is a flowchart showing the processing by the biological signal processor 23 according to the present embodiment.

<Step S5201>

A screen is presented which instructs that right and left fingers be placed in contact with electrodes provided on the manipulation surface of the controller as shown in FIG. 46.

<Step S5202>

It is determined whether the buttons on the manipulation surface that have the auxiliary electrodes placed thereon are pressed down. If it is not confirmed that the buttons have been pressed, control returns to step S5201. If the buttons are pressed down, control proceeds to the next step.

<Step S5203>

In the manipulation-surface electrode signal detector 4601, a potential difference between Ch1 and Ch2 is measured. For example, it is confirmed that chronological data of potential difference as shown in FIG. 48 is being measured.

<Step S5204>

Furthermore, it is confirmed at the manipulation-surface electrode signal detector 4601 whether heart rate information is being detected or not. If heart rate information is not being detected, control again returns to S5201. If a heartbeat component is being detected, control proceeds to the next step.

<Step S5205>

Next, as shown in FIG. 49, the user is instructed to place fingers in contact with the electrodes that are provided on the rear face of the controller.

<Step S5206>

At the rear-face electrode signal detector 4602, potential data on Ch3, Ch4, Ch5, Ch6 is measured against Ch1.

<Step S5207>

Furthermore, at the rear-face electrode signal detector 4602, it is confirmed whether signals as shown in FIGS. 50A and 50B are being detected or not. If they are not being detected, control returns to S5205. If it is confirmed that a heartbeat component similar to that on Ch2 is being detected on Ch5, it is known that fingers have attained contact on the rear face. The flow is ended here, and the user is instructed to begin manipulation, e.g., a game.

As described above, by providing auxiliary electrodes on the manipulation surface of the controller, it becomes easier for the user to confirm contact. Furthermore, conducting the above flow prior to playing a game by using the controller makes it possible to measure more reliable heartbeats.

The above embodiment (e.g., FIG. 8) illustrates that the information processing apparatus 2 includes the biological signal processor 23, and that the biological signal processor 23 performs the process of determining the contact state of each finger. However, such processes may alternatively be performed in the controller 1.

FIG. 52 shows a variant of the construction of FIG. 8. The information processing system according to this variant includes a controller 241 and an information processing apparatus 242. The controller 241 corresponds to the controller 1 in FIG. 8, and the information processing apparatus 242 corresponds to the information processing apparatus 2 in FIG. 8.

In this variant, the process of determining the finger contact states is performed in the controller 241. Therefore, the biological signal processor 23, which was previously included in the information processing apparatus 2 (FIG. 8), is provided in the controller 241 according to this variant. Moreover, the biological signal output section 15 and the biological signal acquisition section 22 in FIG. 8 do not exist. The specific construction and operation of the biological signal processor 23 provided in the controller 241 are as shown in FIG. 14, and the descriptions thereof are omitted.

The controller 241 includes a manipulation input device 241a and a biological signal measurement device 241b.

A manipulation signal output section 2412 of the manipulation input device 241a receives a manipulation signal from the manipulation input section 11, and a result of determining finger contact states from the biological signal processor 23. Then, the manipulation signal output section 2412 outputs such information to the information processing apparatus 242.

The manipulation signal acquisition section 21 acquires a manipulation signal, and sends it to the application processor 24. The application processor 24 performs processing in accordance with the received manipulation signal. The ensuing processing has already been described.

For convenience of description, any constitution corresponding to the display section 3 (FIG. 1) is omitted from illustration in FIG. 52. The display section may or may not be included.

The above embodiments illustrate a stick type (FIG. 2A), a pad type (FIG. 2B), and a tablet type (FIG. 17B) as examples of the controller 1. However, these are examples. For instance, a controller 1 which is obtained by fitting a smartphone into an attachment is another possible example.

FIG. 53 shows an example controller 1 as a combination of an attachment 250 and a smartphone 251. Operation buttons 41 and 42 are provided on a manipulation surface 43 of the attachment 250, and electrodes (not shown) similar to those in FIGS. 3A and 3B or FIGS. 4A and 4B are provided on its rear face or upper side face. The display of the smartphone 251 corresponds to the aforementioned display screen 47. The attachment 250 and the smartphone 251 are connected in a wired or wireless manner, such that manipulations made with the operation buttons 41 and 42 are sent to the information processing apparatus 2 via a communications function which is provided on the smartphone 251 or the attachment 250. Such a controller 1 allows a user of the smartphone, which lacks the electrodes and the operation buttons 41 and 42, to play a game by utilizing electrodes and operation buttons only when he or she wishes.

FIG. 53 illustrates an attachment 250 which covers the entire side faces and rear face of the smartphone 251. However, this is an example. For instance, the operation buttons 41 and 42 may be displayed on the display screen 47 and an input function based on a touch screen panel may be realized, thereby eliminating the need for the operation buttons 41 and 42 as hardware. Then, a sheet member (not shown) which only partially covers the rear face or the upper side face of the smartphone 251 and which has electrodes provided thereon may compose a controller 1 together with the smartphone 251.

FIG. 54 shows the construction of an information processing system 200 as a variant of the information processing system according to Embodiment 1 or 2. In the information processing system 200, a smartphone 251 having an electrode 149 for the left hand and an electrode 147 for the right hand attached on its rear face functions as the controller 1 in FIG. 1. Moreover, a server device 262 which communicates with the controller 1, via a network 263 such as the Internet, functions as the information processing apparatus 2 in FIG. 1. Note that the display screen equipment 3 in FIG. 1 corresponds to the display screen 148 of the smartphone 251.

In the information processing system 200 as such, manipulations on the smartphone 251 are sent to the server device 262, and the server device 262 processes the user's manipulations and biological signal.

Based on the processing result, the server device 262 sends data for displaying on the display screen 148 of the smartphone 251 to the smartphone 251. The smartphone 251 receives this data, and displays it on the display screen 148. The user's manipulation and biological signal and the content of processing thereof are as described with reference to FIG. 8 and FIG. 11.

Instead of the controller 1 shown in FIG. 54, the controller 241 shown in FIG. 52 may be used. In that case, the biological signal is processed at the controller 241, and the manipulation signal is sent to the server device 262.

An information processing system according to the present disclosure includes a bioelectric potential measurement device, and is useful as health monitoring equipment or the like; it also permits game or other applications.

While the present invention has been described with respect to preferred embodiments thereof, it will be apparent to those skilled in the art that the disclosed invention may be modified in numerous ways and may assume many embodiments other than those specifically described above. Accordingly, it is intended by the appended claims to cover all modifications of the invention that fall within the true spirit and scope of the invention.

What is claimed is:

1. An electronic device in a housing to be gripped by a right hand and a left hand of a user for measuring a potential of a first finger and a potential of a second finger of the user, wherein the first finger is a finger of one of the left or right hand, and the second finger is a finger of the other of the left or right hand, the electronic device comprising:
a first electrode group provided in a position to come in contact with the first finger, the first electrode group including a first main electrode and at least one first auxiliary electrode provided at a position away from the first main electrode;
a second electrode group provided in a position to come in contact with the second finger, the second electrode group including a second main electrode and at least one second auxiliary electrode provided at a position away from the second main electrode;
a biological signal processor for, from a potential value measured at the first electrode group and a potential value measured at the second electrode group, determining respective contact states of the first finger and the second finger; and
a transmission circuit for presenting information concerning a finger contact state to the user, based on a result of determination by the biological signal processor.

2. The electronic device of claim 1, wherein,
the at least one first auxiliary electrode includes a plurality of first auxiliary electrodes;
the at least one second auxiliary electrode includes a plurality of second auxiliary electrodes; and
the biological signal processor further determines respective degrees of finger misplacement of the first finger and second finger from a potential value measured at the first electrode group including the plurality of first auxiliary electrodes and a potential value measured at the second electrode group including the plurality of second auxiliary electrodes.

3. The electronic device of claim 2, wherein,
a direction in which misplacement may occur is previously known for each of the first finger and the second finger, and the first electrode group and the second electrode group are disposed along the respective directions in which misplacement may occur;
the biological signal processor determines the degree of finger misplacement of each of the first finger and second finger; and
when the degree of misplacement exceeds a predetermined value, the transmission circuit further outputs information concerning the degree of finger misplacement.

4. The electronic device of claim 2, wherein,
the plurality of first auxiliary electrodes are disposed at symmetric positions with respect to the first main electrode; and
when the first main electrode and the plurality of first auxiliary electrodes are at a same potential, the biological signal processor determines that the degree of misplacement of the first finger is sufficiently small.

5. The electronic device of claim 2, wherein,
the plurality of first auxiliary electrodes are disposed consecutively along a predetermined direction from the first main electrode; and
when the first main electrode and the plurality of first auxiliary electrodes are at a same potential, the biological signal processor determines that the degree of misplacement of the first finger is relatively large.

6. The electronic device of claim 1 satisfying $F \geq X+D+Y$, wherein,
the first main electrode is shaped as a first circle with a diameter X;
the at least one first auxiliary electrode has a length Y along a normal direction of the first circle;
an interspace between the main electrode and the at least one first auxiliary electrode has a minimum value D; and
a second circle surrounding a contact range of the first finger has a diameter F.

7. The electronic device of claim 1 satisfying $F \leq X+D$, wherein,
the first main electrode is shaped as a first circle with a diameter X;
an interspace between the first main electrode and the at least one first auxiliary electrode has a minimum value D; and
a second circle surrounding a contact range of the first finger has a diameter F.

8. The electronic device of claim 1, wherein, according to a change over time in the contact state of the user, the biological signal processor switches between the first main electrode and the at least one first auxiliary electrode as an electrode with which to measure a bioelectric potential.

9. The electronic device of claim 1, wherein,
the first electrode group and the second electrode group include one reference electrode, such that a potential value measured at the first electrode group and a potential value measured at the second electrode group are potential differences against the reference electrode; and
according to a change over time in the contact state of the user, the biological signal processor switches the reference electrode.

10. The electronic device of claim 1, wherein the electrodes included in the first electrode group and the second electrode group are active electrodes.

11. The electronic device of claim 1, further comprising:
a current source connected to each electrode of the first electrode group and the second electrode group for applying an electric current thereto; and
an impedance measurement circuit for, by using the applied electric current, measuring contact impedances between each electrode and the first finger and the second finger,
wherein,
based on a result of contact impedance measurement, the biological signal processor determines the contact state of each of the first finger and the second finger.

12. The electronic device of claim 1, wherein,
the at least one first auxiliary electrode includes a plurality of first auxiliary electrodes;
the at least one second auxiliary electrode includes a plurality of second auxiliary electrodes;
buttons to be manipulated by the user are further provided on the housing; and
the plurality of first auxiliary electrodes and the plurality of second auxiliary electrodes are provided on the buttons and on a rear face of the housing opposite from a face on which the buttons are provided.

13. The electronic device of claim 12, wherein,
the first main electrode and the second main electrode are provided on the rear face,
the electronic device further comprising:
a manipulation surface electrode signal detector for measuring potentials at the first auxiliary electrode and the second auxiliary electrode provided on the buttons; and
a rear face electrode signal detector for measuring potentials at the first main electrode, the second main electrode, the first auxiliary electrode, and the second auxiliary electrode provided on the rear face, wherein,
the biological signal processor determines respective contact states of the first finger and the second finger through comparison between each potential measured by the manipulation surface electrode signal detector and each potential measured by the rear face electrode signal detector.

14. An information processing apparatus for receiving and processing a manipulation signal and a biological signal from an electronic device having a plurality of manipulable portions, wherein,
the biological signal is a potential value measured at a first electrode group provided in a position to come in contact with a first finger of a user gripping a housing of the electronic device and a potential value measured at a second electrode group provided in a position to come in contact with a second finger of the user;
the first finger is a finger of one of a left or right hand of the user, and the second finger is a finger of the other of the left or right hand;
the first electrode group includes a first main electrode and at least one first auxiliary electrode provided at a position away from the first main electrode; and
the second electrode group includes a second main electrode and at least one second auxiliary electrode provided at a position away from the second main electrode,
the information processing apparatus comprising:
a manipulation signal reception circuit for receiving the manipulation signal transmitted from the electronic device;
a biological signal reception circuit for acquiring the biological signal transmitted from the electronic device;
a biological signal processor for, from a potential value measured at the first electrode group and a potential value measured at the second electrode group, determining respective contact states of the first finger and the second finger; and
a transmission circuit for presenting information concerning a finger contact state to the user, based on a result of determination by the biological signal processor.

15. An information processing method to be performed using an electronic device,
the electronic device being in a housing to be gripped by a right hand and a left hand of a user and having a first electrode group provided in a position to come in contact with a first finger of the user and a second electrode group provided in a position to come in contact with a second finger of the user,
the first electrode group including a first main electrode and at least one first auxiliary electrode provided at a position away from the first main electrode, the second electrode group including a second main electrode and at least one second auxiliary electrode provided at a position away from the second main electrode,
the information processing method comprising:
measuring a potential of the first finger and a potential of the second finger, the first finger being a finger of one of the left or right hand, and the second finger being a finger of the other of the left or right hand;
determining respective contact states of the first finger and the second finger from a potential value measured at the first electrode group and a potential value measured at the second electrode group; and
based on a result of the step of determining contact states, presenting information concerning a finger contact state to the user.

16. A computer program, stored on a non-transitory computer-readable medium, to be executed by a computer provided in an electronic device,
the electronic device being in a housing to be gripped by a right hand and a left hand of a user and having a first electrode group provided in a position to come in contact with a first finger of the user and a second electrode group provided in a position to come in contact with a second finger of the user,
the first electrode group including a first main electrode and at least one first auxiliary electrode provided at a position away from the first main electrode, the second electrode group including a second main electrode and at least one second auxiliary electrode provided at a position away from the second main electrode,
the computer program causing the computer to execute:
receiving information of a potential of the first finger and a potential of the second finger measured by the electronic device, the first finger being a finger of one of the left or right hand, and the second finger being a finger of the other of the left or right hand,
determining respective contact states of the first finger and the second finger from a potential value measured at the first electrode group and a potential value measured at the second electrode group; and
based on a result of the step of determining contact states, presenting information concerning a finger contact state to the user.

* * * * *